US012767951B2

(12) United States Patent
Gilbert et al.

(10) Patent No.: US 12,767,951 B2
(45) Date of Patent: *Oct. 20, 2026

(54) COMPOSITIONS AND METHODS FOR TREATMENT OF BLEEDING DISORDERS

(71) Applicant: Band Therapeutics, LLC, Belmont, MA (US)

(72) Inventors: James C. Gilbert, Bethlehem, CT (US); Shuhao Zhu, Concord, MA (US)

(73) Assignee: Band Therapeutics, LLC

( * ) Notice: Subject to any disclaimer, the term of this patent is extended or adjusted under 35 U.S.C. 154(b) by 0 days.

This patent is subject to a terminal disclaimer.

(21) Appl. No.: 18/812,463

(22) Filed: Aug. 22, 2024

(65) Prior Publication Data

US 2024/0417739 A1 Dec. 19, 2024

Related U.S. Application Data

(62) Division of application No. 18/253,975, filed as application No. PCT/US2021/060678 on Nov. 24, 2021.

(60) Provisional application No. 63/216,601, filed on Jun. 30, 2021, provisional application No. 63/155,012, filed on Mar. 1, 2021, provisional application No. 63/117,545, filed on Nov. 24, 2020.

(51) Int. Cl.
*C12N 15/115* (2010.01)
*A61P 7/00* (2006.01)

(52) U.S. Cl.
CPC .............. *C12N 15/115* (2013.01); *A61P 7/00* (2018.01); *C12N 2310/16* (2013.01)

(58) Field of Classification Search
CPC ..... C12N 15/115; C12N 2310/16; A61P 7/02; A61K 48/00
See application file for complete search history.

(56) References Cited

U.S. PATENT DOCUMENTS

| | | | |
|---|---|---|---|
| 7,566,701 | B2 | 7/2009 | Diener et al. |
| 11,060,094 | B2 * | 7/2021 | Zhu ........................... A61P 7/02 |
| 2005/0130156 | A1 | 6/2005 | Frey et al. |
| 2009/0170793 | A1 | 7/2009 | Gaur |
| 2009/0203766 | A1 | 8/2009 | Gilbert et al. |
| 2011/0118187 | A1 | 5/2011 | Sullenger et al. |
| 2012/0035110 | A1 | 2/2012 | Grillberger et al. |
| 2012/0316116 | A1 * | 12/2012 | Scheiflinger ............ A61P 43/00 514/14.1 |
| 2017/0044545 | A1 | 2/2017 | Ikeda |
| 2018/0043012 | A1 | 2/2018 | Moses et al. |
| 2018/0305695 | A1 | 10/2018 | Hirao et al. |
| 2018/0346912 | A1 | 12/2018 | Hirao et al. |
| 2021/0292763 | A1 | 9/2021 | Zhu et al. |
| 2023/0038761 | A1 | 2/2023 | Zhu et al. |
| 2024/0002861 | A1 | 1/2024 | Gilbert et al. |
| 2024/0247274 | A1 | 7/2024 | Zhu |

FOREIGN PATENT DOCUMENTS

| | | | |
|---|---|---|---|
| CN | 101300361 | A | 11/2008 |
| CN | 109982707 | A | 7/2019 |
| CN | 110520128 | A | 11/2019 |
| EP | 3624801 | A1 | 3/2020 |
| JP | 2008512098 | A | 4/2008 |
| KR | 20160147884 | A | 12/2016 |
| RU | 2524129 | C2 | 7/2014 |
| RU | 2563236 | C2 | 9/2015 |
| WO | 2006033854 | A2 | 3/2006 |
| WO | 2008150495 | A2 | 12/2008 |
| WO | 2008150496 | A2 | 12/2008 |
| WO | 2010003687 | A | 1/2010 |
| WO | 2010091396 | A3 | 9/2010 |
| WO | 2015163458 | A1 | 10/2015 |
| WO | 2016143700 | A1 | 9/2016 |
| WO | 2017073536 | A1 | 5/2017 |
| WO | 2018213697 | A1 | 11/2018 |

OTHER PUBLICATIONS

International Search Report for PCT/2018/033376 dated Oct. 2, 2018 (5 pages).

Rattus norvegicus clone CH230-214G17, Working Draft Sequence, 4 unordered pieces, GenBank: AC106539, retrieved from URL: https://www.ncbi.nlm.nih.gov/nuccore/AC106539 (51 pages).

Banerjee, Amiya A., "5'-Terminal Cap Structure in Eucaryotic Messenger Ribonucleic Acids", Microbiol. Rev., vol. 44, No. 2, Jun. 1980, pp. 175-205 (31 pages).

Gilbert, James C. et al., "First-in-Human Evaluation of Anti-von Willebrand Factor Therapeutic Aptamer ARC1779 in Health Volunteers", Circulation (2007) vol. 116 (23):2678-2686, doi: 10.1161/CIRCULATIONAHA.107.724864 (9 pages).

Jilma-Stohlawetz Petra, et al., "The anti-von Willebrand factor aptamer ARC1779 increases von Willebrand factor levels and platelet counts in patients with type 2B von Willebrand disease", Blood Coagulation, Fibrinolysis and Cellular Haemostasis, Thrombosis and Haemostasis 108.2/2012 (7 pages).

Matsunaga, Ken-Ichiro et al., "High-Affinity DNA Aptamer Generation Targeting von Willebrand Factor A1-Domain by Genetic Alphabet Expansion for Systematic Evolution of Ligands by Exponential Enrichment Using two Types of Libraries Composed of Five Different Bases", Journal of the American Cancer Society, vol. 139, No. 1, Jan. 11, 2017, pp. 324-334 (11 pages).

Mishra, Prajna et al., "PEGylation in anti-cancer therapy: An overview", Asian Journal of Pharmaceutical Sciences II (2016) pp. 337-348 (12 pages).

Reinstein, Oren et al., "Engineering a Structure Switching Mechanism into a Steroid-Binding Aptamer and Hydrodynamic Analysis of the Ligand Binding Mechanism", Biochemistry, 50/43, Sep. 26, 2011, pp. 9368-9376 (9 pages).

(Continued)

*Primary Examiner* — J. E. Angell
(74) *Attorney, Agent, or Firm* — Proskauer Rose LLP

(57) ABSTRACT

The present disclosure relates to treatment of bleeding disorders, in particular, hemophilia A (mild, moderate or severe hemophilia) and von Willebrand disease (VWD), Type 1 or Type 2 or Type 3, using VWF targeting agents such as a PEGylated anti-VWF aptamer, BT200.

28 Claims, 5 Drawing Sheets

Specification includes a Sequence Listing.

(56) References Cited

OTHER PUBLICATIONS

Siller-Matula, Jolanta M. et al., "ARC15105 Is a Potent Antagonist of Von Willebrand Factor Mediated Platelet Activation and Adhesion", Arterioscler Thromb Vasc Biol 2012, 32:902-909 (12 pages).
Zhu, Shuhao et al., "The development and characterization of a long acting anti-thrombotic von Willebrand factor (VWF) aptamer", J Thromb Haemost. wileyonlinelibrary.com/journal/jth, DOI:10.1111/jth.14755 (2020) pp. 1113-1123 (11 pages).
International Search Report for PCT/US2021/060678 dated Apr. 11, 2022 (5 pages).
Bannow, Bethany Samuelson, et al., "Factor VIII: Long-established role in haemophilia A and emerging evidence beyond haemostasis", Blood Reviews 35 (2019) pp. 43-50 (8 pages).
Ay, Cihan et al., "The VWF binding aptamer rondoraptivon pegol increases platelet counts and VWF/FVIII in type 2B von Willebrand disease," Blood advances, Sep. 27, 2022, vol. 6, No. 18, pp. 5467-5476 (10 pages).
Chion, Alain et al., "The aptamer BT200 blocks interaction of K1405-K1408 in the VWF-A1 domain with macrophage LRP1," Blood, Sep. 26, 2024, vol. 144, No. 13, pp. 1445-1456 (12 pages).
Kovacevic, K.D. et al., "The von Willebrand factor A-1 domain binding aptamer BT200 elevates plasma levels of von Willebrand factor and factor VIII: a first-in-human trial," Haematologica, 107, Sep. 2022, pp. 2121-2132 (12 pages).
Mojzisch, Angelika et al., "The Manifold Cellular Functions of von Willebrand Factor," Cells (2021), 10, 2351, https://doi.org/10.3390/cells10092351 (25 pages).
Bae, Ok-Nam, "Targeting von Willebrand Factor as a Novel Anti-platelet Therapy; Application of ARC1779, an Anti-vWF Aptamer, against Thrombotic Risk", Arch Pharm Res, vol. 35, No. 10. 2012. pp. 1693-1699. DOI 10.1007/s12272-012-1000-3 (7 pages).
Blackshear, Joseph L., et al., "Indices of von Willebrand Factor as Biomarkers of Aortic Stenosis Severity: (From the Biomarkers of Aortic Stenosis Severity [BASS] Study)", Am J Cardiol. Feb. 1, 2013; 111(3): 374-381. DOI: 10.1016/j.amjcard.2012.10.015 (16 pages).
Capoccia, Massimo, et al., "Recurrent Early Thrombus Formation in HeartMate II Left Ventricular Assist Device", Journal of Investigative Medicine High Impact Case Reports, 2013, pp. 1-3, DOI: 10.1177/2324709613490676, (3 pages).
Chen, Junmei, et al., "The rate of hemolysis in sickle cell disease correlates with the quantity of active von Willebrand factor in the plasma", Blood, vol. 117, No. 13. Mar. 31, 2011; DOI 10.1182/blood-2010-08-302539. pp. 3680-3683 (4 pages).
Couffinhal, Thierry, "Mouse Model of Angiogenesis", Am J Pathol, vol. 152, No. 6. pp. 1667-1679 (13 pages). Jun. 1998.
Couffinhal, Thierry, et al., "Mouse models to study angiogenesis in the context of cardiovascular diseases", Frontiers in Bioscience vol. 14, pp. 3310-3325 (16 pages), Jan. 1, 2009.
De Maistre, Emmanuel, et al., "Performance of two new automated assays for measuring von Willebrand activity: HemosIL AcuStar and Innovance", Thrombosis and Haemostasis, vol. 112, No. 4. DOI: 10.1160/TH14-02-0108. pp. 1-6 (7 pages).
De Mast, Quirijn, et al., "ADAMTS13 Deficiency with Elevated Levels of Ultra-Large and Active von Willebrand Factor in P. falciparum and P. vivax Malaria", Am. J. Trop. Med. Hyg., vol. 80, No. 3, 2009, pp. 492-498 (7 pages).
Diener, J. L., et al., "Inhibition of von Willebrand factor-mediated platelet activation and thrombosis by the anti-von Willebrand factor A1-domain aptamer ARC1779", Journal of Thrombosis and Haemostasis, vol. 7. Apr. 15, 2009. DOI: 10.1111/j.1538-7836.2009.03459.x. pp. 1155-1162 (8 pages).
Firbas, Christa, et al., "Targeting von Willebrand factor and platelet glycoprotein lb receptor", Expert Rev. Cardiovasc. Ther. vol. 8, No. 12, DOI: 10.1586/ERC.10.154. pp. 1689-1701 (14 pages).
Flannery, Conor James, et al., "Thrombus Formation Under High Shear in Arterial Stenotic Flow", Georgia Institute of Technology, May 2005 pp. i-164 (176 pages).
Fraser, Katharine H., et al., "Computational Fluid Dynamics Analysis of Thrombosis Potential in Left Ventricular Assist Device Drainage Cannulae", ASA/OJ 2010; vol. 56 No. 3: 157-163. DOI:10.1097/:t,., 1ATOb013e3181d861fl. (19 pages).
Fu, Hongxia, et al., "Flow-induced elongation of von Willebrand factor precedes tension-dependent activation", Nature Communications, vol. 8, No. 324, 2017, pp. 1-12, DOI: 10.1038/s41467-017-00230-2, (12 pages).
Gragnano, Felice, et al., "Von Willebrand factor as a novel player in valvular heart disease: from bench to valve replacement", Angiology, 2017. pp. 1-25 (26 pages).
Heilmann, Claudia, et al., "Haemolysis in patients with ventricular assist devices: major differences between systems", European Journal of Cardio-thoracic Surgery, vol. 36. Apr. 6, 2009. DOI: 10.1016/j.ejcts.2009 .04.015 pp. 580-584 (5 pages).
Hemker, H. Coenraad, et al., "Thrombin generation, a function test of the haemostaticthrombotic system", Thromb Haemost, vol. 96. Aug. 1, 2006. DOI: 10.1160/TH06-07-0408. pp. 553-561 (9 pages).
Hollestelle, Martine J., et al., "von Willebrand factor propeptide in malaria: evidence of acute endothelial cell activation", British Journal of Haematology, vol. 133. 2006. DOI: 10.1114/j.1365-2141.2006.06067.x. pp. 562-569 (8 pages).
Huang, Ren-Huai, et al., "A Structural Explanation for the Antithrombotic Activity of ARC1172, a DNA Aptamer that Binds von Willebrand Factor Domain A1", Structure, vol. 17, pp. 1476-1484, Nov. 11, 2009. DOI 10.1016tj.str.2009.09.011. (9 pages).
Ingram, David A., et al., "Identification of a novel hierarchy of endothelial progenitor cells using human peripheral and umbilical cord blood", Blood, vol. 104. Jun. 29, 2004. pp. 2752-2760 DOI:10.1182/b!ood-2004-04-1396 (10 pages).
Islam, Sameer, et al., "Left Ventricular Assist Devices and Gastrointestinal Bleeding: A Narrative Review of Case Reports and Case Series", Clin. Cardiol. vol. 36, No. 4. Jan. 2, 2013. pp. 190-200. DOI: 10.1002/dc.22096. (11 pages).
Jilma-Stohlawetz, Petra, et al., "A dose ranging phase I/II trial of the von Willebrand factor inhibiting aptamer ARC1779 in patients with congenital thrombotic thrombo-cytopenic purpura", Thrombosis and Haemostasis, vol. 106, No. 3. Aug. 11, 2011. pp. 539-547. DOI: 10.1160/TH11-02-0069. (9 pages).
Jilma-Stohlawetz, Petra, et al., "Inhibition of von Willebrand factor by ARC1779 in patients with acute thrombotic thrombocytopenia purpura", Thrombosis and Haemostasis, vol. 105, No. 3. 2011. pp. 545-552. DOI: 10.1160/TH10-08-0520. (8 pages).
Lawrie, A. S., "A comparative evaluation of a new automated assay for von Willebrand factor activity", Haemophilia, vol. 19. 2013. pp. 338-342 DOI: 10.1111/hae.12064 (5 pages).
Le Behot, Audrey, et al., "Gplba-VWF blockade restores vessel patency by dissolving platelet aggregates formed under very high shear rate in mice", Blood, vol. 123, No. 21, Feb. 16, 2014, pp. 3354-3363, DOI: 10.1182/blood-2013-12-543074, (10 pages).
Levin, Tobias, "Design of a High Shear Stress Experiment", Studienarbeit, Mar. 2010. pp. i-96 (105 pages).
Maeda, Masashi, et al., "FK419, a nonpeptide platelet glycoprotein IIb/IIIa antagonist, ameliorates brain infarction associated with thrombotic focal cerebral ischemia in monkeys: comparison with tissue plasminogen activator", Journal of Cerebral Blood Flow & Metabolism, vol. 25. (2005) pp. 108-118 DOI: 10.1038/sj.jcbfm.9600013. (11 pages).
Meyer, Anna Lassia, et al., "Thrombus formation in a HeartMate II left ventricular assist device", J Thorac Cardiovasc Surg, vol. 135, No. 1, 2008, pp. 203-204, DOI: 10.1016/j.jtcvs.2007.08.048, (2 pages).
Montgomery, Robert R., "The heads and tails of malaria and VWF", Blood, vol. 127. Mar. 3, 2016. pp. 1081-1083 DOI: 10.1182/blood-2015-11-679878 (3 pages).
Nishio, Kenji, et al., "Binding of platelet glycoprotein Iba to von Willebrand factor domain A1 stimulates the cleavage of the adjacent domain A2 by ADAMTS13", PNAS, vol. 101, No. 29. Jul. 20, 2004. pp. 10578-10583. DOI: 10.1073/pnas.0402041101. (6 pages).
Randi, Anna M., et al., "Von Willebrand Factor, Angiodysplasia and Angiogenesis", Mediterr J Hematol Infect Dis 2013, 5(1): Sep. 2, 2013 (9 pages) e2013060, DOI: 10.4084/MJHID.2013.060.
Rothenburger, Markus, et al., "Treatment of Thrombus Formation Associated with the MicroMed DeBakey VAD Using Recombinant

(56) References Cited

OTHER PUBLICATIONS

Tissue Plasminogen Activator", Circulation, vol. 106. pp. I-189-I192. DOI: 10.1161/01.cir.0000032913.33237.f5. (5 pages).

Schneider, S. W., et al., "Shear-induced unfolding triggers adhesion of von Willebrand factor fibers", PNAS, vol. 104, No. 19. May 8, 2007. pp. 7899-7903 DOI: 10.1073/pnas.0608422104 (5 pages).

Schoergenhofer, Christian, et al., "The use of frozen plasma samples in thromboelastometry", Clin Exp Med, 2017. DOI: 10.1007/s10238-017-0454-5 (9 pages).

Shim, Kyuhwan, et al., "Platelet-VWF complexes are preferred substrates of ADAMTS13 under fluid shear stress", Blood, vol. 111, No. 2. Sep. 27, 2007. pp. 651-657. DOI: 10.1182/blood-2007-05-093021 (8 pages).

Siediecki, C. A., et al., "Shear-dependent changes in the three-dimensional structure of human von Willebrand factor", Blood, vol. 88, No. 8. Oct. 15, 1996. pp. 2939-2950 (13 pages).

Starke, Richard D., et al., "Endothelial von Willebrand factor regulates angiogenesis", Blood, vol. 117, No. 3. 2011. pp. 1071-1080. DOI: 10.1182/blood-2010-01-264507. (11 pages).

Starling, R. C., et al., "Supplement to: Starling RC, Moazami N, Silvestry SC, et al. Unexpected abrupt increase in left ventricular assist device thrombosis", N Engl J Med, vol. 370. 2013/2014. pp. 1-50 (51 pages).

Starling, Randall C., et al., "Unexpected Abrupt Increase in Left Ventricular Assist Device Thrombosis", N Engl J Med. Jan. 2, 2014; vol. 370, No. 1. DOI: 10.1056/NEJMoa1313385. pp. 33-40 (8 pages).

Suarez, Jorge, et al., "Mechanisms of Bleeding and Approach to Patients With Axial-Flow Left Ventricular Assist Devices", Circ Heart Fail, vol. 4, Sep. 15, 2011, pp. 779-784 (6 pages) DOI: 10.1161/CIRCHEARTFAILURE.111.962613.

Treetharnmathurot, Benjaporn, et al., "Effect of PEG molecular weight and linking chemistry on the biological activity and thermal stability of PEGylated trypsin", International Journal of Pharmaceutics, vol. 357. 2008. pp. 252-259 DOI: 10.1016/j.ijphann.2008.01.016 (8 pages).

Turecek, Peter L., et al., "PEGylation of Biopharmaceuticals: A Review of Chemistry and Nonclinical Safety Information of Approved Drugs", Journal of Pharmaceutical Sciences, vol. 105. 2016. pp. 460-475 DOI: 10.1016/j.xphs.2015.11.015 (16 pages).

Varga-Szabo, David, et al., "Cell Adhesion Mechanisms in Platelets", Arterioscler Thromb Vasc Biol, vol. 28. 2008. pp. 403-412. DOI: 10.1161/ATVBAHA.107.150474. (11 pages).

Vaz, Alexandra, et al., "Sindrome de Heyde—.Associacao entre estenose aortica e hemorragia gastrointestinal", Rev Port Cardiol, vol. 29, No. 2. Feb. 10, 2010. pp. 309-314. (6 pages).

Vincentelli, Andre, et al., "Acquired von Willebrand Syndrome in Aortic Stenosis", N Engl J Med, vol. 349, No. 4. Jul. 24, 2003. pp. 343-349 (7 pages).

Zheng, Ying, et al., "Flow-driven assembly of VWF fibres and webs in in vitro microvessels", Nature Communications, vol. 6, No. 7858. Jul. 30, 2015. pp. 1-11. DOI:10.1038/ncomms8858. (11 pages).

Zheng, Ying, et al., "In vitro microvessels for the study of angiogenesis and thrombosis", PNAS, vol. 109, No. 24. Jun. 12, 2012. pp. 9342-9347 DOI: 10.1073/pnas.1201240109. (6 pages).

* cited by examiner

SEQUENCE LISTING

```
Sequence total quantity: 8
SEQ ID NO: 1            moltype = AA  length = 2813
FEATURE                 Location/Qualifiers
source                  1..2813
                        mol_type = protein
                        organism = Homo sapiens
SEQUENCE: 1
MIPARFAGVL LALALILPGT LCAEGTRGRS STARCSLFGS DFVNTFDGSM YSFAGYCSYL  60
LAGGCQKRSF SIIGDFQNGK RVSLSVYLGE FFDIHLFVNG TVTQGDQRVS MPYASKGLYL  120
ETEAGYYKLS GEAYGFVARI DGSGNFQVLL SDRYFNKTCG LCGNFNIFAE DDFMTQEGTL  180
TSDPYDFANS WALSSGEQWC ERASPPSSSC NISSGEMQKG LWEQCQLLKS TSVFARCHPL  240
VDPEPFVALC EKTLCECAGG LECACPALLE YARTCAQEGM VLYGWTDHSA CSPVCPAGME  300
YRQCVSPCAR TCQSLHINEM CQERCVDGCS CPEGQLLDEG LCVESTECPC VHSGKRYPPG  360
TSLSRDCNTC ICRNSQWICS NEECPGECLV TGQSHFKSFD NRYFTFSGIC QYLLARDCQD  420
HSFSIVIETV QCADDRDAVC TRSVTVRLPG LHNSLVKLKH GAGVAMDGQD VQLPLLKGDL  480
RIQHTVTASV RLSYGEDLQM DWDGRGRLLV KLSPVYAGKT CGLCGNYNGN QGDDFLTPSG  540
LAEPRVEDFG NAWKLHGDCQ DLQKQHSDPC ALNPRMTRFS EEACAVLTSP TFEACHRAVS  600
PLPYLRNCRY DVCSCSDGRE CLCGALASYA AACAGRGVRV AWREPGRCEL NCPKGQVYLQ  660
CGTPCNLTCR SLSYPDEECN EACLEGCFCP PGLYMDERGD CVPKAQCPCY YDGEIFQPED  720
IFSDHHTMCY CEDGFMHCTM SGVPGSLLPD AVLSSPLSHR SKRSLSCRPP MVKLVCPADN  780
LRAEGLECTK TCQNYDLECM SMGCVSGCLC PPGMVRHENR CVALERCPCF HQGKEYAPGE  840
TVKIGCNTCV CRDRKWNCTD HVCDATCSTI GMAHYLTFDG LKYLFPGECQ YVLVQDYCGS  900
NPGTFRILVG NKGCSHPSVK CKKRVTILVE GGEIELFDGE VNVKRPMKDE THFEVVESGR  960
YIILLLGKAL SVVWDRHLSI SVVLKQTYQE KVCGLCGNFD GIQNNDLTSS NLQVEEDPVD  1020
FGNSWKVSSQ CADTRKVPLD SSPATCHNNI MKQTMVDSSC RILTSDVFQD CNKLVDPEPY  1080
LDVCIYDTCS CESIGDCACF CDTIAAYAHV CAQHGKVVTW RTATLCPQSC EERNLRENGY  1140
ECEWRYNSCA PACQVTCQHP EPLACPVQCV EGCHAHCPPG KILDELLQTC VDPEDCPVCE  1200
VAGRRFASGK KVTLNPSDPE HCQICHCDVV NLTCEACQEP GGLVVPPTDA PVSPTTLYVE  1260
DISEPPLHDF YCSRLLDLVF LLDGSSRLSE AEFEVLKAFV VDMMERLRIS QKWVRVAVVE  1320
YHDGSHAYIG LKDRKRPSEL RRIASQVKYA GSQVASTSEV LKYTLFQIFS KIDRPEASRI  1380
TLLLMASQEP QRMSRNFVRY VQGLKKKKVI VIPVGIGPHA NLKQIRLIEK QAPENKAFVL  1440
SSVDELEQQR DEIVSYLCDL APEAPPPTLP PDMAQVTVGP GLLGVSTLGP KRNSMVLDVA  1500
FVLEGSDKIG EADFNRSKEF MEEVIQRMDV GQDSIHVTVL QYSYMVTVEY PFSEAQSKGD  1560
ILQRVREIRY QGGNRTNTGL ALRYLSDHSF LVSQGDREQA PNLVYMVTGN PASDEIKRLP  1620
GDIQVVPIGV GPNANVQELE RIGWPNAPIL IQDFETLPRE APDLVLQRCC SGEGLQIPTL  1680
SPAPDCSQPL DVILLLDGSS SFPASYFDEM KSFAKAFISK ANIGPRLTQV SVLQYGSITT  1740
IDVPWNVVPE KAHLLSLVDV MQREGGPSQI GDALGFAVRY LTSEMHGARP GASKAVVILV  1800
TDVSVDSVDA AADAARSNRV TVFPIGIGDR YDAAQLRILA GPAGDSNVVK LQRIEDLPTM  1860
VTLGNSFLHK LCSGFVRICM DEDGNEKRPG DVWTLPDQCH TVTCQPDGQT LLKSHRVNCD  1920
RGLRPSCPNS QSPVKVEETC GCRWTCPCVC TGSSTRHIVT FDGQNFKLTG SCSYVLFQNK  1980
EQDLEVILHN GACSPGARQG CMKSIEVKHS ALSVELHSDM EVTVNGRLVS VPYVGGNMEV  2040
NVYGAIMHEV RFNHLGHIFT FTPQNNEFQL QLSPKTFASK TYGLCGICDE NGANDFMLRD  2100
GTVTTDWKTL VQEWTVQRPG QTCQPILEEQ CLVPDSSHCQ VLLLPLFAEC HKVLAPATFY  2160
AICQQDSCHQ EQVCEVIASY AHLCRTNGVC VDWRTPDFCA MSCPPSLVYN HCEHGCPRHC  2220
DGNVSSCGDH PSEGCFCPPD KVMLEGSCVP EEACTQCIGE DGVQHQFLEA WVPDHQPCQI  2280
CTCLSGRKVN CTTQPCPTAK APTCGLCEVA RLRQNADQCC PEYECVCDPV SCDLPPVPHC  2340
ERGLQPTLTN PGECRPNFTC ACRKEECKRV SPPSCPPHRL PTLRKTQCCD EYECACNCVN  2400
STVSCPLGYL ASTATNDCGC TTTTCLPDKV CVHRSTIYPV GQFWEEGCDV CTCTDMEDAV  2460
MGLRVAQCSQ KPCEDSCRSG FTYVLHEGEC CGRCLPSACE VVTGSPRGDS QSSWKSVGSQ  2520
WASPENPCLI NECVRVKEEV FIQQRNVSCP QLEVPVCPSG FQLSCKTSAC CPSCRCERME  2580
ACMLNGTVIG PGKTVMIDVC TTCRCMVQVG VISGFKLECR KTTCNPCPLG YKEENNTGEC  2640
```

-continued

```
CGRCLPTACT IQLRGGQIMT LKRDETLQDG CDTHFCKVNE RGEYFWEKRV TGCPPFDEHK  2700
CLAEGGKIMK IPGTCCDTCE EPECNDITAR LQYVKVGSCK SEVEVDIHYC QGKCASKAMY  2760
SIDINDVQDQ CSCCSPTRTE PMQVALHCTN GSVVYHEVLN AMECKCSPRK CSK         2813

SEQ ID NO: 2           moltype = DNA  length = 8833
FEATURE                Location/Qualifiers
source                 1..8833
                       mol_type = other DNA
                       organism = Homo sapiens
SEQUENCE: 2
agctcacagc tattgtggtg ggaaagggag ggtggttggt ggatgtcaca gcttgggctt  60
tatctccccc agcagtgggg actccacagc ccctgggcta cataacagca agacagtccg  120
gagctgtagc agacctgatt gagcctttgc agcagctgag agcatggcct agggtgggcg  180
gcaccattgt ccagcagctg agtttcccag ggaccttgga gatagccgca gccctcattt  240
gcaggggaag atgattcctg ccagatttgc cggggtgctg cttgctctgg ccctcatttt  300
gccagggacc ctttgtgcag aaggaactcg cggcaggtca tccacggccc gatgcagcct  360
tttcggaagt gacttcgtca acacctttga tgggagcatg tacagctttg cgggatactg  420
cagttacctc ctggcagggg gctgccagaa acgctccttc tcgattattg ggggacttcca  480
gaatggcaag agagtgagcc tctccgtgta tcttggggaa tttttgaca tccatttgtt  540
tgtcaatggt accgtgacac agggggacca aagagtctcc atgccctatg cctccaaagg  600
gctgtatcta gaaactgagg ctgggtacta caagctgtcc ggtgaggcct atggctttgt  660
ggccaggatc gatggcagcg gcaactttca agtcctgctg tcagacagat acttcaacaa  720
gacctgcggg ctgtgtggca actttaacat ctttgctgaa gatgacttta tgacccaaga  780
agggaccttg acctcggacc cttatgactt tgccaactca tgggctctga gcagtggaga  840
acagtggtgt gaacgggcat ctcctcccag cagctcatgc aacatctcct ctggggaaat  900
gcagaagggc ctgtgggagc agtgccagct tctgaagagc acctcggtgt ttgcccgctg  960
ccaccctctg gtggaccccg agccttttgt ggccctgtgt gagaagactt tgtgtgagtg  1020
tgctgggggg ctggagtgcg cctgccctgc cctcctggag tacgcccgga cctgtgccca  1080
ggagggaatg gtgctgtacg gctggaccga ccacagcgcg tgcagcccag tgtgccctgc  1140
tggtatggag tataggcagt gtgtgtcccc ttgcgccagg acctgccaga gcctgcacat  1200
caatgaaatg tgtcaggagc gatgcgtgga tggctgcagc tgccctgagg gacagctcct  1260
ggatgaaggc ctctgcgtgg agagcaccga gtgtccctgc gtgcattccg gaaagcgcta  1320
ccctcccggc acctccctct ctcgagactg caacacctgc atttgccgaa acagccagtg  1380
gatctgcagc aatgaagaat gtccagggga gtgccttgtc acaggtcaat cacacttcaa  1440
gagctttgac aacagatact tcaccttcag tgggatctgc cagtacctgc tggcccggga  1500
ttgccaggac cactccttct ccattgtcat tgagactgtc cagtgtgctg atgaccgcga  1560
cgctgtgtgc acccgctccg tcaccgtccg gctgcctggc ctgcacaaca gccttgtgaa  1620
actgaagcat ggggcaggag ttgccatgga tggccaggac gtccagctcc ccctcctgaa  1680
aggtgacctc cgcatccagc atacagtgac ggcctccgtg cgcctcagct acggggagga  1740
cctgcagatg gactgggatg gccgcgggag gctgctggtg aagctgtccc ccgtctatgc  1800
cgggaagacc tgcggcctgt gtgggaatta caatggcaac cagggcgacg acttccttac  1860
cccctctggg ctggcggagc cccgggtgga ggacttcggg aacgcctgga agctgcacgg  1920
ggactgccag gacctgcaga agcagcacag cgatccctgc gccctcaacc cgcgcatgac  1980
caggttctcc gaggaggcgt gcgcggtcct gacgtccccc acattcgagg cctgccatcg  2040
tgccgtcagc ccgctgccct acctgcggaa ctgccgctac gacgtgtgct cctgctcgga  2100
cggccgcgag tgcctgtgcg gcgccctggc cagctatgcc gcggcctgcg cggggagagg  2160
cgtgcgcgtc gcgtggcgcg agccaggccg ctgtgagctg aactgcccga aaggccaggt  2220
gtacctgcag tgcgggaccc cctgcaacct gacctgccgc tctctctctt acccggatga  2280
ggaatgcaat gaggcctgcc tggagggctg cttctgcccc ccagggctct acatggatga  2340
gaggggggac tgcgtgccca aggcccagtg cccctgttac tatgacggtg agatcttcca  2400
gccagaagac atcttctcag accatcacac catgtgctac tgtgaggatg gcttcatgca  2460
ctgtaccatg agtggagtcc ccggaagctt gctgcctgac gctgtcctca gcagtcccct  2520
gtctcatcgc agcaaaagga gcctatcctg tcggcccccc atggtcaagc tggtgtgtcc  2580
cgctgacaac ctgcgggctg aagggctcga gtgtaccaaa acgtgccaga actatgacct  2640
ggagtgcatg agcatgggct gtgtctctgg ctgcctctgc cccccgggca tggtccggca  2700
tgagaacaga tgtgtggccc tggaaaggtg tccctgcttc catcagggca aggagtatgc  2760
ccctggagaa acagtgaaga ttggctgcaa cacttgtgtc tgtcgggacc ggaagtggaa  2820
ctgcacagac catgtgtgtg atgccacgtg ctccacgatc ggcatggccc actacctcac  2880
cttcgacggg ctcaaatacc tgttccccgg ggagtgccag tacgttctgg tgcaggatta  2940
ctgcggcagt aaccctggga cctttcggat cctagtgggg aataagggat gcagccaccc  3000
ctcagtgaaa tgcaagaaac gggtcaccat cctggtggag ggaggagaga ttgagctgtt  3060
tgacggggag gtgaatgtga agaggcccat gaaggatgag actcactttg aggtggtgga  3120
gtctggccgg tacatcattc tgctgctggg caaagccctc tccgtggtct gggaccgcca  3180
cctgagcatc tccgtggtcc tgaagcagac ataccaggag aaagtgtgtg gcctgtgtgg  3240
gaattttgat ggcatccaga acaatgacct caccagcagc aacctccaag tggaggaaga  3300
ccctgtggac tttgggaact cctggaaagt gagctcgcag tgtgctgaca ccagaaaagt  3360
gcctctggac tcatcccctg ccacctgcca taacaacatc atgaagcaga cgatggtgga  3420
ttcctcctgt agaatcctta ccagtgacgt cttccaggac tgcaacaagc tggtggaccc  3480
cgagccatat ctggatgtct gcatttacga cacctgctcc tgtgagtcca ttggggactg  3540
cgcctgcttc tgcgacacca ttgctgccta tgcccacgtg tgtgcccagc atggcaaggt  3600
ggtgacctgg aggacggcca cattgtgccc ccagagctgc gaggagagga atctccggga  3660
gaacgggtat gagtgtgagt ggcgctataa cagctgtgca cctgcctgtc aagtcacgtg  3720
tcagcaccct gagccactgg cctgccctgt gcagtgtgtg gagggctgcc atgcccactg  3780
ccctccaggg aaaatcctgg atgagctttt gcagacctgc gttgaccctg aagactgtcc  3840
agtgtgtgag gtggctggcc ggcgttttgc ctcaggaaag aaagtcacct tgaatcccag  3900
tgaccctgag cactgccaga tttgccactg tgatgttgtc aacctcacct gtgaagcctg  3960
ccaggagccg ggaggcctgg tggtgcctcc cacagatgcc ccggtgagcc ccaccactct  4020
gtatgtggag gacatctcgg aaccgccgtt gcacgatttc tactgcagca ggctactgga  4080
cctggtcttc ctgctggatg gctcctccag gctgtccgag gctgagtttg aagtgctgaa  4140
```

-continued

```
ggcctttgtg gtggacatga tggagcggct gcgcatctcc cagaagtggg tccgcgtggc  4200
cgtggtggag taccacgacg gctcccacgc ctacatcggg ctcaaggacc ggaagcgacc  4260
gtcagagctg cggcgcattg ccagccaggt gaagtatgcg ggcagccagg tggcctccac  4320
cagcgaggtc ttgaaataca cactgttcca aatcttcagc aagatcgacc gccctgaagc  4380
ctcccgcatc accctgctcc tgatggccag ccaggagccc caacggatgt cccggaactt  4440
tgtccgctac gtccagggcc tgaagaagaa gaaggtcatt gtgatcccgg tgggcattgg  4500
gccccatgcc aacctcaagc agatccgcct catcgagaag caggcccctg agaacaaggc  4560
cttcgtgctg agcagtgtgg atgagctgga gcagcaaagg gacgagatcg ttagctacct  4620
ctgtgacctt gcccctgaag cccctcctcc tactctgccc cccgacatgg cacaagtcac  4680
tgtgggcccg gggctcttgg gggtttcgac cctggggccc aagaggaact ccatggttct  4740
ggatgtggcg ttcgtcctgg aaggatcgga caaaattggt gaagccgact tcaacaggag  4800
caaggagttc atggaggagg tgattcagcg gatggatgtg ggccaggaca gcatccacgt  4860
cacggtgctg cagtactcct acatggtgac tgtggagtac cccttcagcg aggcacagtc  4920
caaaggggac atcctgcagc gggtgcgaga gatccgctac cagggcggca acaggaccaa  4980
cactgggctg gccctgcggt acctctctga ccacagcttc ttggtcagcc agggtgaccg  5040
ggagcaggcg cccaacctgg tctacatggt caccggaaat cctgcctctg atgagatcaa  5100
gaggctgcct ggagacatcc aggtggtgcc cattggagtg ggccctaatg ccaacgtgca  5160
ggagctggag aggattggct ggcccaatgc ccctatcctc atccaggact ttgagacgct  5220
cccccgagag gctcctgacc tggtgctgca gaggtgctgc tccggagagg ggctgcagat  5280
ccccaccctc tcccctgcac ctgactgcag ccagcccctg gacgtgatcc ttctcctgga  5340
tggctcctcc agtttcccag cttcttattt tgatgaaatg aagagtttcg ccaaggcttt  5400
catttcaaaa gccaatatag ggcctcgtct cactcaggtg tcagtgctgc agtatggaag  5460
catcaccacc attgacgtgc catggaacgt ggtcccggag aaagcccatt tgctgagcct  5520
tgtggacgtc atgcagcggg agggaggccc cagccaaatc ggggatgcct tgggctttgc  5580
tgtgcgatac ttgacttcag aaatgcatgg tgccaggccg ggagcctcaa aggcggtggt  5640
catcctggtc acggacgtct ctgtggattc agtggatgca gcagctgatg ccgccaggtc  5700
caacagagtg acagtgttcc ctattggaat tggagatcgc tacgatgcag cccagctacg  5760
gatcttggca ggcccagcag gcgactccaa cgtggtgaag ctccagcgaa tcgaagacct  5820
ccctaccatg gtcaccttgg gcaattcctt cctccacaaa ctgtgctctg gatttgttag  5880
gatttgcatg gatgaggatg ggaatgagaa gaggcccggg gacgtctgga ccttgccaga  5940
ccagtgccac accgtgactt gccagccaga tggccagacc ttgctgaaga gtcatcgggt  6000
caactgtgac cgggggctga ggccttcgtg ccctaacagc cagtcccctg ttaaagtgga  6060
agagacctgt ggctgccgct ggacctgccc ctgcgtgtgc acaggcagct ccactcggca  6120
catcgtgacc tttgatgggc agaatttcaa gctgactggc agctgttctt atgtcctatt  6180
tcaaaacaag gagcaggacc tggaggtgat tctccataat ggtgcctgca gccctggagc  6240
aaggcagggc tgcatgaaat ccatcgaggt gaagcacagt gccctctccg tcgagctgca  6300
cagtgacatg gaggtgacgg tgaatgggag actggtctct gttccttacg tgggtgggaa  6360
catggaagtc aacgtttatg gtgccatcat gcatgaggtc agattcaatc accttggtca  6420
catcttcaca ttcactccac aaaacaatga gttccaactg cagctcagcc ccaagacttt  6480
tgcttcaaag acgtatggtc tgtgtgggat ctgtgatgag aacggagcca atgacttcat  6540
gctgagggat ggcacagtca ccacagactg gaaaacactt gttcaggaat ggactgtgca  6600
gcggccaggg cagacgtgcc agcccatcct ggaggagcag tgtcttgtcc ccgacagctc  6660
ccactgccag gtcctcctct taccactgtt tgctgaatgc cacaaggtcc tggctccagc  6720
cacattctat gccatctgcc agcaggacag ttgccaccag gagcaagtgt gtgaggtgat  6780
cgcctcttat gcccacctct gtcggaccaa cggggtctgc gttgactgga ggacacctga  6840
tttctgtgct atgtcatgcc caccatctct ggtctacaac cactgtgagc atggctgtcc  6900
ccggcactgt gatggcaacg tgagctcctg tggggaccat ccctccgaag gctgtttctg  6960
ccctccagat aaagtcatgt tggaaggcag ctgtgtccct gaagaggcct gcactcagtg  7020
cattggtgag gatggagtcc agcaccagtt cctggaagcc tgggtcccgg accaccagcc  7080
ctgtcagatc tgcacatgcc tcagcgggcg gaaggtcaac tgcacaacgc agccctgccc  7140
cacggccaaa gctcccacgt gtggcctgtg tgaagtagcc cgcctccgcc agaatgcaga  7200
ccagtgctgc cccgagtatg agtgtgtgtg tgacccagtg agctgtgacc tgcccccagt  7260
gcctcactgt gaacgtggcc tccagcccac actgaccaac cctggcgagt gcagacccaa  7320
cttcacctgc gcctgcagga aggaggagtg caaaagagtg tccccaccct cctgcccccc  7380
gcaccgtttg cccacccttc ggaagaccca gtgctgtgat gagtatgagt gtgcctgcaa  7440
ctgtgtcaac tccacagtga gctgtcccct tgggtacttg gcctcaactg ccaccaatga  7500
ctgtggctgt accacaacca cctgccttcc cgacaaggtg tgtgtccacc gaagcaccat  7560
ctaccctgtg ggccagttct gggaggaggg ctgcgatgtg tgcacctgca ccgacatgga  7620
ggatgccgtg atgggcctcc gcgtggccca gtgctcccag aagccctgtg aggacagctg  7680
tcggtcgggc ttcacttacg ttctgcatga aggcgagtgc tgtggaaggt gcctgccatc  7740
tgcctgtgag gtggtgactg gctcaccgcg gggggactcc cagtcttcct ggaagagtgt  7800
cggctcccag tgggcctccc cggagaaccc ctgcctcatc aatgagtgtg tccgagtgaa  7860
ggaggaggtc tttatacaac aaaggaacgt ctcctgcccc cagctggagg tccctgtctg  7920
cccctcgggc tttcagctga gctgtaagac ctcagcgtgc tgcccaagct gtcgctgtga  7980
gcgcatggag gcctgcatgc tcaatggcac tgtcattggg cccgggaaga ctgtgatgat  8040
cgatgtgtgc acgacctgcc gctgcatggt gcaggtgggg gtcatctctg gattcaagct  8100
ggagtgcagg aagaccacct gcaacccctg cccccctgggt tacaaggaag aaaataacac  8160
aggtgaatgt tgtgggagat gtttgcctac ggcttgcacc attcagctaa gaggaggaca  8220
gatcatgaca ctgaagcgtg atgagacgct ccaggatggc tgtgatactc acttctgcaa  8280
ggtcaatgag agaggagagt acttctggga gaagagggtc acaggctgcc cacccctttga  8340
tgaacacaag tgtctggctg agggaggtaa aattatgaaa attccaggca cctgctgtga  8400
cacatgtgag gagcctgagt gcaacgacat cactgccagg ctgcagtatg tcaaggtggg  8460
aagctgtaag tctgaagtag aggtggatat ccactactgc cagggcaaat gtgccagcaa  8520
agccatgtac tccattgaca tcaacgatgt gcaggaccag tgctcctgct gctctccgac  8580
acggacggag cccatgcagg tggccctgca ctgcaccaat ggctctgttg tgtaccatga  8640
ggttctcaat gccatggagt gcaaatgctc ccccaggaag tgcagcaagt gaggctgctg  8700
cagctgcatg ggtgcctgct gctgcctgcc ttggcctgat ggccaggcca gagtgctgcc  8760
agtcctctgc atgttctgct cttgtgccct tctgagccca caataaaggc tgagctctta  8820
tcttgcaaaa ggc                                                    8833
```

```
SEQ ID NO: 3            moltype = RNA  length = 29
FEATURE                 Location/Qualifiers
source                  1..29
                        mol_type = other RNA
                        organism = synthetic construct
SEQUENCE: 3
gccagggacc taagacacat gtccctggc                                    29

SEQ ID NO: 4            moltype = RNA  length = 30
FEATURE                 Location/Qualifiers
source                  1..30
                        mol_type = other RNA
                        organism = synthetic construct
modified_base           30
                        mod_base = OTHER
                        note = Inverted nucleotide
modified_base           1
                        mod_base = gm
modified_base           2..3
                        mod_base = cm
modified_base           4
                        mod_base = OTHER
                        note = 2'-O-methyladenosine
modified_base           5..7
                        mod_base = gm
modified_base           8
                        mod_base = OTHER
                        note = 2'-O-methyladenosine
modified_base           9..10
                        mod_base = cm
modified_base           11
                        mod_base = um
modified_base           12..13
                        mod_base = OTHER
                        note = 2'-O-methyladenosine
modified_base           14
                        mod_base = gm
modified_base           15
                        mod_base = OTHER
                        note = 2'-O-methyladenosine
modified_base           16
                        mod_base = cm
modified_base           17
                        mod_base = OTHER
                        note = 2'-O-methyladenosine
modified_base           18
                        mod_base = cm
modified_base           19
                        mod_base = OTHER
                        note = 2'-O-methyladenosine
modified_base           20
                        mod_base = um
modified_base           21
                        mod_base = gm
modified_base           22
                        mod_base = um
modified_base           23..25
                        mod_base = cm
modified_base           26
                        mod_base = um
modified_base           27..28
                        mod_base = gm
modified_base           29
                        mod_base = cm
SEQUENCE: 4
gccagggacc taagacacat gtccctggct                                   30

SEQ ID NO: 5            moltype = RNA  length = 30
FEATURE                 Location/Qualifiers
source                  1..30
                        mol_type = other RNA
                        organism = synthetic construct
modified_base           30
                        mod_base = OTHER
                        note = Inverted nucleotide
modified_base           1
                        mod_base = gm
modified_base           2..3
```

```
                        mod_base = cm
modified_base           4
                        mod_base = OTHER
                        note = 2'-O-methyladenosine
modified_base           5..7
                        mod_base = gm
modified_base           8
                        mod_base = OTHER
                        note = 2'-O-methyladenosine
modified_base           9..10
                        mod_base = cm
modified_base           11
                        mod_base = um
modified_base           12..13
                        mod_base = OTHER
                        note = 2'-O-methyladenosine
modified_base           14
                        mod_base = gm
modified_base           15
                        mod_base = OTHER
                        note = 2'-O-methyladenosine
modified_base           16
                        mod_base = cm
modified_base           17
                        mod_base = OTHER
                        note = 2'-O-methyladenosine
modified_base           18
                        mod_base = cm
modified_base           19
                        mod_base = OTHER
                        note = 2'-O-methyladenosine
modified_base           20
                        mod_base = um
modified_base           21
                        mod_base = gm
modified_base           22
                        mod_base = um
modified_base           23..25
                        mod_base = cm
modified_base           26
                        mod_base = um
modified_base           27..28
                        mod_base = gm
modified_base           29
                        mod_base = cm
SEQUENCE: 5
gccagggacc taagacacat gtccctggct                                    30

SEQ ID NO: 6            moltype = RNA  length = 30
FEATURE                 Location/Qualifiers
source                  1..30
                        mol_type = other RNA
                        organism = synthetic construct
modified_base           30
                        mod_base = OTHER
                        note = Inverted nucleotide
modified_base           1
                        mod_base = gm
modified_base           2..3
                        mod_base = cm
modified_base           4
                        mod_base = OTHER
                        note = 2'-O-methyladenosine
modified_base           5..7
                        mod_base = gm
modified_base           8
                        mod_base = OTHER
                        note = 2'-O-methyladenosine
modified_base           9..10
                        mod_base = cm
modified_base           11
                        mod_base = um
modified_base           12..13
                        mod_base = OTHER
                        note = 2'-O-methyladenosine
modified_base           14
                        mod_base = gm
modified_base           15
                        mod_base = OTHER
```

```
                          note = 2'-O-methyladenosine
modified_base             16
                          mod_base = cm
modified_base             17
                          mod_base = OTHER
                          note = 2'-O-methyladenosine
modified_base             18
                          mod_base = cm
modified_base             19
                          mod_base = OTHER
                          note = 2'-O-methyladenosine
modified_base             20
                          mod_base = um
modified_base             21
                          mod_base = gm
modified_base             22
                          mod_base = um
modified_base             23..25
                          mod_base = cm
modified_base             26
                          mod_base = um
modified_base             27..28
                          mod_base = gm
modified_base             29
                          mod_base = cm
SEQUENCE: 6
gccagggacc taagacacat gtccctggct                                  30

SEQ ID NO: 7              moltype = RNA  length = 22
FEATURE                   Location/Qualifiers
source                    1..22
                          mol_type = other RNA
                          organism = synthetic construct
modified_base             22
                          mod_base = OTHER
                          note = inverted nucleotide
modified_base             1..3
                          mod_base = gm
modified_base             4
                          mod_base = OTHER
                          note = 2'-O-Methyladenosine
modified_base             5..6
                          mod_base = cm
modified_base             7
                          mod_base = um
modified_base             8..9
                          mod_base = OTHER
                          note = 2'-O-Methyladenosine
modified_base             10
                          mod_base = gm
modified_base             11
                          mod_base = OTHER
                          note = 2'-O-Methyladenosine
modified_base             12
                          mod_base = cm
modified_base             13
                          mod_base = OTHER
                          note = 2'-O-Methyladenosine
modified_base             14
                          mod_base = cm
modified_base             15
                          mod_base = OTHER
                          note = 2'-O-Methyladenosine
modified_base             16
                          mod_base = um
modified_base             17
                          mod_base = gm
modified_base             18
                          mod_base = um
modified_base             19..21
                          mod_base = cm
SEQUENCE: 7
gggacctaag acacatgtcc ct                                          22

SEQ ID NO: 8              moltype = RNA  length = 40
FEATURE                   Location/Qualifiers
source                    1..40
                          mol_type = other RNA
                          organism = synthetic construct
```

-continued

```
modified_base           1
                        mod_base = gm
modified_base           8
                        mod_base = gm
modified_base           20
                        mod_base = gm
misc_feature            20..21
modified_base           22
                        mod_base = gm
modified_base           27
                        mod_base = gm
modified_base           30
                        mod_base = um
modified_base           33
                        mod_base = gm
modified_base           36
                        mod_base = OTHER
                        note = 2'-o-methyladenosine
modified_base           40
                        mod_base = OTHER
                        note = Inverted nucleotide
modified_base           28
                        mod_base = cm
modified_base           34
                        mod_base = um
modified_base           37
                        mod_base = cm
modified_base           38
                        mod_base = gm
modified_base           39
                        mod_base = cm
modified_base           2
                        mod_base = cm
modified_base           3
                        mod_base = gm
modified_base           4
                        mod_base = um
modified_base           9
                        mod_base = um
modified_base           10
                        mod_base = gm
modified_base           11
                        mod_base = cm
modified_base           12
                        mod_base = cm
modified_base           13..14
                        mod_base = um
modified_base           15
                        mod_base = cm
modified_base           16..17
                        mod_base = gm
modified_base           18
                        mod_base = cm
SEQUENCE: 8
gcgtgcagtg ccttcggccg tgcggtgcct ccgtcacgct                 40
```

COMPOSITIONS AND METHODS FOR TREATMENT OF BLEEDING DISORDERS

CROSS REFERENCE TO RELATED APPLICATIONS

This application is a Divisional Application of U.S. patent application Ser. No. 18/253,975, filed on May 23, 2023, which is a 35 U.S.C. § 371 National Stage Application of International Application No. PCT/US2021/060678, filed on Nov. 24, 2021, which claims the benefit and priority to U.S. Provisional Patent Application No. 63/117,545, filed on Nov. 24, 2020; 63/155,012, filed on Mar. 1, 2021; and 63/216,601, filed on Jun. 30, 2021; the contents of each of which are incorporated herein by reference in their entirety.

REFERENCE TO THE SEQUENCE LISTING

The present application is being filed along with a Sequence Listing submitted electronically in XML format. The Sequence Listing entitled GBT-006US2_SL, is created on Aug. 21, 2024, and is 63,804 bytes in size. The content of the electronically submitted sequence listing is incorporated herein by reference in its entirety.

FIELD OF THE DISCLOSURE

The present disclosure relates to agents, compositions and methods for treatment of bleeding disorders such as hereditary bleeding disorders (e.g., hemophilia A and von Willebrand disease (VWD)). The methods use agents binding to VWF and pharmaceutical compositions and formulations thereof.

BACKGROUND OF THE DISCLOSURE

Bleeding disorders are a heterogeneous group of conditions in which the blood cannot properly coagulate. As a result, patients with bleeding disorders will experience extensive bleeding after injury, trauma or surgery, etc. Some patients could develop severe, and spontaneous bleeding. Bleeding disorders can be inherited or acquired. Inherited bleeding disorders are often caused by deficiencies in factors involved on blood coagulation (i.e., coagulation factors; also known as clotting factors), and abnormalities of blood vessels and platelets. Hereditary bleeding disorders caused by deficient coagulation proteins include hemophilia A and B, von Willebrand Disease (VWD) Type 1, Type 2 (including subtypes 2a, 2b, 2m and 2n), and Type 3 and other rare bleeding disorders. Platelet-caused bleeding disorders include the inherited thrombocytopenia with less platelet counts Bernard-Soulier syndrome and Glanzmann's thrombasthenia.

Blood coagulation is a complex process including the sequential interaction of a series of components, in particular of fibrinogen, Factor II (FII), Factor V (FV), Factor VII (FVII), Factor VIII (FVIII), Factor IX (FIX), Factor X (FX), Factor XI (FXI), Factor XII (FXII) and von Willebrand Factor (VWF). The clotting components interact with platelet in the blood to maintain normal hemostasis.

Deficiencies in any of the clotting components and/or disruptions of the regulation between clotting components and platelet could result in bleeding disorders. Genetic defects in clotting factors, e.g., mutations in the genes encoding these factors cause rare hereditary bleeding, e.g., hemophilia. Hemophilia is an X-linked inherited bleeding disorder with a frequency of about one in 10,000 births.

Hemophilia is caused by a deficiency of coagulation factor VIII (FVIII) (hemophilia A) or factor IX (FIX) (hemophilia B) (e.g., reviewed by Samuelson et al., *Blood Rev.,* 2019, 35:43-50). Mutations in the gene coding FVIII can result in hemophilia A. The clinical presentation for hemophilia A is usually characterized by episodes of spontaneous and prolonged bleedings, ranging from mild, moderate to severe.

Von Willebrand factor (VWF), a large plasma glycoprotein, circulates in plasma and plays essential roles in normal hemostasis. VWF mediates platelet adhesion to exposed sub-endothelial collagen at sites of vascular injury to facilitate platelet mediated plug formation. VWF also performs its hemostatic functions through binding to Factor VIII (FVIII) and to platelets surface glycoproteins, and to localize FVIII to sites of platelet plug and subsequent clot formation. VWF complexed with FVIII also stabilizes the FVIII protein in plasma and protects it from proteolytic degradation by activated protein C in the circulation. The FVIII-VWF complex therefore extends the circulatory life of FVIII.

Deficiencies and/or defects of VWF can result in von Willebrand disease (VWD). The most common symptoms of VWD include mucocutaneous bleeding, hematomas, and bleeding after trauma or surgery, similar to hemophilia A due to the rapid degradation FVIII caused by lacking VWF cofactor. VWD is the most common inherited bleeding disorder with an estimated prevalence of ~1%. Clinically relevant bleeding symptoms are present in approximately 1:10,000 individuals. VWD can be caused by a quantitative and/or qualitative defect in VWF. Quantitative deficiencies of VWF are often associated with severe VWD Type 1 and Type 3. VWD Type 2 is usually caused by qualitative defects in VWF (i.e., functional defects in VWF). For example, VWD Type 2b is characterised by an increased binding affinity of VWF to platelet glycoprotein Ib, which leads to consumption of VWF and thrombocytopenia in some VWD patients with a resulting severe bleeding phenotype.

Currently hemophilia A is treated with protein replacement therapy using either plasma derived or recombinant FVIII. Although FVIII replacement/substitute could markedly improve the life of patients suffering from hemophilia, hemophilia patients are still at risk for severe bleeding episodes and chronic joint damage, since prophylactic treatment is restricted by the short half-life, the limited availability, and the high cost of purified FVIII proteins. Treatment and prevention of bleedings in VWD patients focus on increasing plasma VWF and FVIII levels to adequate hemostatic levels. Current treatments include stimulation of the release of endogenous VWF by administration of desmopressin (DDAVP) and infusion of VWF-containing factor concentrates (e.g., VWF/FVIII concentrates) or recombinant VWF preparations. Choice of treatment is dependent on the type of disease and the severity of the bleeding.

The present disclosure provides VWF targeting agents to treat bleeding disorders, in particular hemophilia A, including mild, moderate and severe hemophilia, and von Willebrand disease (VWD) Type 1, Type 2 (e.g., Type 2a, Type 2b, Type 2m and Type 2n) and Type 3. The VWF targeting agents include VWF binding aptamers and variants thereof.

SUMMARY OF THE DISCLOSURE

In one aspect of the present disclosure, methods for treating a bleeding disorder in a patient are provided. The methods comprise administering to the patient a pharmaceutically efficient amount of a composition comprising a VWF targeting agent.

In accordance with the present disclosure, the patient is diagnosed with a bleeding disorder. The bleeding disorder is a hereditary bleeding disorder, including hemophilia A (e.g., mild, moderate or severe hemophilia), and VWD (e.g., VWD Type 1, VWD Type 2a, Type 2b, Type 2m and Type 2n, and VWD Type 3), inherited thrombocytopenia and a rare bleeding disorder. The bleeding disorder may also be acquired, e.g., inhibitor induced thrombocytopenia. In one embodiment, the patient is diagnosed with hemophilia A. The patient may have mild hemophilia, moderate hemophilia, or severe hemophilia. In another embodiment, the patient is diagnosed with VWD Type 1, Type 2 such as Type 2a, Type 2b and Type 2n, or Type 3.

In some embodiments, the VWF targeting agent is a VWF binding agent that binds to VWF. The VWF targeting agent is an antibody, a nanobody, a peptide, an oligonucleotide, an RNA (e.g., siRNA, microRNA), a synthetic polynucleotide (e.g., an aptamer), or a small molecule.

In some embodiments, the VWF binding agent is a synthetic polynucleotide selected from SEQ ID No.: 3, BT99 (SEQ ID No.: 4), BT100 (SEQ ID No.: 5), BT200 (SEQ ID No.: 6), ARC15105 (SEQ ID No.: 7), ARC1779 (SEQ ID No.: 8) or a variant thereof.

In some embodiments, the patient having a bleeding disorder may receive a single dose, or multiple doses of the VWF targeting agent. In one embodiment, the patient receives multiple doses of the VWF binding agent.

In one preferred embodiment, the VWF targeting agent is BT200, a PEGylated aptamer that specifically binds to the A1 domain of human VWF. In one embodiment, BT200 is administered at a dose ranging from 1.0 mg to 10.0 mg, or from 1.0 mg to 6.0 mg.

In another aspect, the present disclosure provides methods for increasing the circulatory level of VWF in a blood system of a subject. The method comprises administering to the subject a composition comprising a VWF targeting agent. The VWF targeting agent binds to VWF and increase the VWF levels in the circulation. In some embodiments, the VWF targeting agent is a VWF binding agent that binds to VWF. As non-limiting examples, the VWF binding agent is a synthetic polynucleotide selected from SEQ ID No.: 3, BT99 (SEQ ID No.: 4), BT100 (SEQ ID No.: 5), BT200 (SEQ ID No.: 6), ARC15105 (SEQ ID No.: 7), ARC1779 (SEQ ID No.: 8) or a variant thereof. In one preferred embodiment, the VWF target agent is BT200, a PEGylated aptamer that specifically binds to the A1 domain of human VWF. BT200 is administered at a dose ranging from 1.0 mg to 10.0 mg, or from 1.0 mg to 6.0 mg. In some embodiments, the subject is diagnosed with VWD, e.g., VWD Type 1, VWD Type 2 including Type 2a, Type 2b and Type 2n, and VWD Type 3. In other embodiments, the subject is diagnosed with VWD including Type 1, Type 2 and Type 3 and receives a factor replacement treatment.

In yet another aspect, the present disclosure provides methods for extending the circulatory life of FVIII in a blood system of a subject. The method comprises administering to the subject a composition comprising a VWF targeting agent. The VWF targeting agent binds to VWF and increases the FVIII levels in the circulation. In some embodiments, the VWF targeting agent is a VWF binding agent that binds to VWF. As non-limiting examples, the VWF binding agent is a synthetic polynucleotide selected from SEQ ID No.: 3, BT99 (SEQ ID No.: 4), BT100 (SEQ ID No.: 5), BT200 (SEQ ID No.: 6), ARC15105 (SEQ ID No.: 7), ARC1779 (SEQ ID No.: 8) or a variant thereof. In one preferred embodiment, the VWF target agent is BT200, a PEGylated aptamer that specifically binds to the A1 domain of human VWF. BT200 is administered at a dose ranging from 1.0 mg to 10.0 mg, or from 1.0 mg to 6.0 mg. In some embodiments, the subject is diagnosed with hemophilia A, e.g., mild, moderate or severe hemophilia. In some examples, the subject is diagnosed with hemophilia A and receives a factor replacement treatment. In other embodiments, the subject is diagnosed with VWD Type 1, or VWD Type 2 (including Type 2a, Type 2b and Type 2n), or VWD Type 3. In some examples, the subject is diagnosed with VWD and receives a VWF replacement treatment.

DETAILED DESCRIPTION OF THE DISCLOSURE

Figure 1:
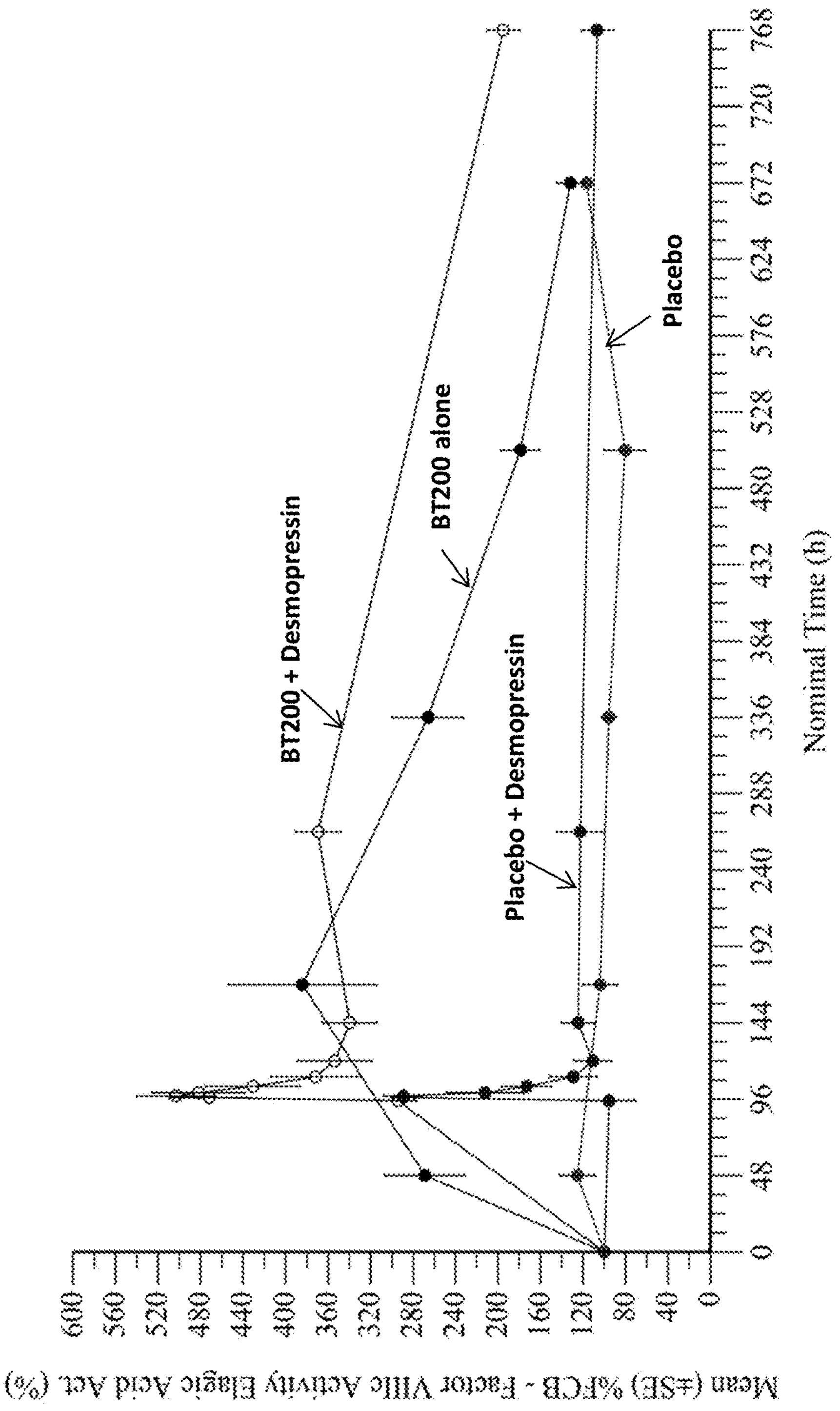
FIG. 1 displays additive effects on the levels of VWF and FVIII by coadministration of BT200 and desmopressin in healthy volunteers.

The details of one or more embodiments of the disclosure are set forth in the accompanying description below. Although any materials and methods similar or equivalent to those described herein can be used in the practice or testing of the present disclosure, the preferred materials and methods are now described. Other features, objects and advantages of the disclosure will be apparent from the description. In the description, the singular forms also include the plural unless the context clearly dictates otherwise. Unless defined otherwise, all technical and scientific terms used herein have the same meaning as commonly understood by one of ordinary skill in the art to which this disclosure belongs. In the case of conflict, the present description will control.

The present disclosure relates to methods, agents, and pharmaceutical compositions and formulations thereof, for treating a bleeding disorder such as an inherited bleeding disorder (e.g., hemophilia A and VWD). A method for treating a bleeding disorder in a patient comprises administering to the patient a therapeutically effective amount of a pharmaceutical composition comprising an agent targeting to von Willebrand factor (VWF).

Particularly the agents herein relate to any molecules that can target to VWF in the blood. The VWF targeting agents can bind to VWF to mediate VWF hemostatic function. A VWF targeting agent may be an antibody, a nanobody, a peptide, an oligonucleotide, an RNA (e.g., siRNA, microRNA), an aptamer and a variant thereof, or a small molecule. In accordance with the present disclosure, the VWF targeting agent is a synthetic polynucleotide derived from an aptamer that specifically binds to VWF. The targeting agent may be further modified with one or more chemical modifications and conjugates. The agent and VWF complexes protect circulating VWF from clearance, thereby increasing the levels of VWF and FVIII in the blood to increase clotting.

Definitions

To more clearly and concisely describe the subject matter of the claimed disclosure, the following definitions are provided for specific terms, which are used in the following description and the appended claims. Throughout the specification, exemplification of specific terms should be considered as non-limiting examples.

Pharmaceutical composition: As used herein, the term "pharmaceutical composition" is sometimes used interchangeably with the term "pharmaceutical formulation". It refers to the combination of an active compound with a pharmaceutically acceptable carrier or excipient, inert or active, making the composition suitable for diagnostic or therapeutic use in vitro, in vivo or ex vivo. In the context of the present disclosure, the active compound may be one or more compound that can be used to treat a bleeding disorder.

Pharmaceutically acceptable excipient: As used herein, the term "pharmaceutically acceptable excipient" means a carrier or excipient that is useful in preparing a pharmaceutical composition that is generally safe, non-toxic and neither biologically nor otherwise undesirable, and includes a carrier or excipient that is acceptable for veterinary use as well as human pharmaceutical use. A "pharmaceutically acceptable carrier or excipient" as used in the specification and claims includes both one and more than one such carrier or excipient. As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. In some examples, the compositions and formulations also can include stabilizers and preservatives. The term "pharmaceutically acceptable" refers to molecular entities and compositions that are physiologically tolerable and do not typically produce untoward reactions when administered to a human. Preferably, as used herein, the term "pharmaceutically acceptable" means approved by a regulatory agency of the Federal or a state government or listed in the U.S. Pharmacopeia or other generally recognized pharmacopcia for use in animals, and more particularly in humans, or generally recognized as safe for use in parenteral products.

Therapeutically effective amount: As used herein, the term "therapeutically effective amount" refers to the amount of the compound that is sufficient to result in a therapeutic response. In connection with the present disclosure, the term "therapeutically effective amount" may refer to the amount of an anti-VWF aptamer that is sufficient to result in a therapeutic response. A therapeutic response may be any response that a user (e.g., a clinician) will recognize as an effective response to the therapy. The exact amount required will vary from subject to subject, depending on the species, age, and general condition of the subject, the particular therapeutic agent, its mode and/or route of administration, and the like. It will be understood, however, that the total daily usage of the compounds and compositions of the present disclosure can be decided by an attending physician within the scope of sound medical judgment.

Preventing, prevention or prevent: As used herein, the terms "prevent," "preventing," and "prevention" and grammatical variations thereof are used interchangeably. These terms refer to a method of partially or completely delaying or precluding the onset or recurrence of a disorder or conditions and/or one or more of its attendant symptoms or barring a subject from acquiring or reacquiring a disorder or condition or reducing a subject's risk of acquiring or reacquiring a disorder or condition or one or more of its attendant symptoms.

Treating, treatment or treat: As used herein, the terms "treating," "treatment" and "to treat" and grammatical variations thereof, refer to administering to a subject an effective amount of a pharmaceutical composition, such that at least one symptom of a disease is reversed, cured, alleviated, improved, reduced, decreased, or reaches beneficial or desired clinical results such as diminishment of extent of disease, stabilized (e.g., not worsening) state of disease, delay or slowing of disease progression, amelioration or palliation of the disease state, and remission (partial or total; and detectable or undetectable).

Subject: As used herein, the term "subject" is used interchangeably with the terms "individual" and "patient", and refers to a vertebrate, preferably a mammal, more preferably a human.

Injection: As used herein, the terms "injection" or "injectable formulation" refer to a composition that can be drawn into a syringe and injected subcutaneously, intraperitoneally, or intramuscularly into a subject (e.g., human).

Parenteral administration: As used herein, the term "parenteral administration" of a pharmaceutical formulation means administration to a subject by a route other than topical or oral (i.e., a non-topical and non-oral route). Examples of parenteral routes include subcutaneous, intramuscular, intravascular (including intraarterial or intravenous), intraperitoneal, intraorbital, retrobulbar, peribulbar, intranasal, intrapulmonary, intrathecal, intraventricular, intraspinal, intracisternal, intracapsular, intrasternal or intralesional administration. Parenteral administration may be, e.g., by bolus injection or continuous infusion, either constant or intermittent and/or pulsatile, and may be via a needle or via a catheter or other tubing.

Subcutaneous administration: As used herein, the term "subcutaneous administration" refers to a common route of administration of a pharmaceutical composition, including but not limited to subcutaneous injection and infusion. The infusion may be continuous or in spurts using infusion pumps or any other commercially available devices.

Hemostasis and Clotting Components

Blood coagulation is a complex and dynamic biological process involving the sequential interactions of clotting components including coagulation factors: Factor II (FII), Factor V (FV), Factor VII (FVII), Factor VIII (FVIII), Factor IX (FIX), Factor X (FX), Factor XI (FXI), Factor XII (FXII) and cofactor, von Willebrand Factor (VWF).

Factor VIII (FVIII) (also known as anti-hemophilic factor A), a large, plasma glycoprotein, is a key component of the fluid phase blood coagulation cascade. FVIII is primarily produced by hepatocytes and vascular endothelial cells. Human FVIII is one of the largest coagulation factors including three A-domains, a unique B-domain, and two C-domains and activated via proteolytic cleavage by FXa and thrombin to generate the activated FVIII heterotrimer (FVIIIa). FVIIIa acts as a non-enzymatic cofactor for the prothrombinase and tenase complex in the coagulation cascade that accelerates FX activation in the presence of FIXa, phospholipids and calcium ions (Fay et al., *Blood Reviews,* 2004, 18:1-15). The half-life of FVIII is about 12 hours. To avoid excessive coagulation, FVIIIa must be inactivated soon after activation, by Protein C (APC) mediated cleavage. The inactivation of FVIIIa is a rapid process, which explains the short half-life of FVIIIa in the blood. As used herein, the terms "Factor VIII(a)" and "FVIII(a)" include both FVIII and FVIIIa. Similarly, the term "Factor VIII" and "FVIII" may include both FVIII and FVIIIa.

FVIII present in plasma is in association with von Willebrand factor (VWF), forming a noncovalent FVIII-VWF complex. Von Willebrand factor (VWF) is a large, multimeric glycoprotein and plays a key role in hemostasis and thrombosis. Human VWF preproprotein (GeneBank Ref. No. NP_000543.2; SEQ ID No.: 1) (encoded by cDNA: GeneBank Ref. No. NM_000552.3; SEQ ID No.: 2) is processed to be a mature polypeptide comprising multiple subdomains with different functions (Hassan and Saxena, *Blood Coagul. Fibrinolysis,* 2012, 23(1):11-22). VWF is the carrier protein for FVIII, binding FVIII to platelets surface glycoproteins and localizing FVIII to sites of platelet plug and subsequent clot formation. VWF also acts as a stabilizer of FVIII in the circulation by the formation of the non-covalently bound VWF-FVIII complex that protects FVIII from degradation by activated protein C (APC), thereby preventing FVIII from premature proteolysis (Koppelman et al., Blood. 1996; 87:2292-2300). In addition, VWF blocks the interaction of FVIII with lipoprotein-related receptors and thereby increases the half-life of FVIII in the circulation.

Furthermore, the interaction between VWF and FVIII plays a crucial role in FVIII function, immunogenicity, and clearance, with VWF essentially serving as a chaperone for FVIII. VWF has an important protective role for FVIII both under normal physiological conditions and in patients with hemophilia. In hemophilia patents who have developed FVIII inhibitors (e.g., antibodies to FVIII substitute) after treatment with FVIIII replacement therapy, VWF may protect exogenous FVIII from the binding of inhibitory antibodies (Gensana et al., Hemophilia. 2001; 7:369-374).

Plasma levels of VWF can affect risk of bleeding (lower level of VWF) or thrombosis (higher level of VWF). Quantitative deficiencies (low levels) of plasma VWF (e.g., <50%) are associated with an increased risk for bleeding, while high plasma levels of VWF (e.g., >150%) increase the risk for thrombosis (e.g., higher risk for venous thromboembolic disease, ischemic stroke, coronary artery disease, myocardial infarction and peripheral vascular disease).

Bleeding and Bleeding Disorders

A deficiency in the coagulation process may increase the risk of bleeding, For example, coagulation factor deficiencies and defects in platelet number or function cause bleeding disorders. Bleeding can occur inside the body (internal bleeding) or underneath the skin or from the surface of the skin (external bleeding).

As used herein, the term "bleeding disorders" refer to a heterogeneous group of conditions that result when the blood cannot clot properly. In normal clotting, platelets stick together and form a plug at the site of an injured blood vessel. Coagulation factors in the blood interact to form a fibrin clot, essentially a gel plug, which holds the platelets in place and allows healing to occur at the site of the injury while preventing blood from escaping the blood vessel. The inability to form clots can be very dangerous, resulting in excessive bleeding. Bleeding can result from either too few or abnormal platelets, abnormal or low amounts of coagulation factors, dysfunctional coagulation factors (e.g., mutations in the genes encoding coagulation factors), or abnormal blood vessels. The bleeding severity can be assessed according to guidelines such as the assessment tool reviewed by Rodeghiero et al., ISTH/SSC bleeding assessment tool: a standardized questionnaire and a proposal for a new bleeding score for inherited bleeding disorders. *J Thromb Haemost. September* 2010; 8(9):2063-5. doi:10.1111/j.1538-7836.2010.03975.x). A person with a bleeding disorder can have both internal and external bleeds. Common symptoms of a bleeding disorder include but not limited to, extended bleeding after injury, surgery, trauma, or menstruation; excessive bruising; bleeding into joints, muscles and soft tissues; gastrointestinal bleeding; spontaneous bleeding without a known or identifiable cause.

Bleeding disorders can be hereditary or acquired. As used herein, the term "hereditary bleeding disorders" (also called "congenital bleeding disorders") refers to a group of rare disorders caused by genetic deficiency of clotting components. The most common bleeding disorders include hemophilia (e.g., hemophilia A and B) and VWD (e.g., Types 1, 2 and 3). Hemophilia A or Hemophilia B is a rare, hereditary bleeding disorder that can range from mild, moderate to severe, depending on how much the residual factor activity is present in in a patient's plasma. The incidence of hemophilia A is ~1 in 5000 live male births and that of hemophilia B is 1 in 25 000 live male births. Collectively, they are among the most common inherited bleeding disorders in the world. Von Willebrand disease (VWD) is the most common inherited bleeding disorder in America affecting up to 1% of the US population.

Bleeding may also result from a low platelet (thrombocyte) count in the blood, a condition called thrombocytopenia. A normal platelet count in adults ranges from 150,000 to 450,000 platelets per microliter of blood. A platelet count of less than 150,000 platelets per microliter is lower than normal (thrombocytopenia). The risk for serious bleeding does not occur until the count becomes very low—less than 10,000 or 20,000 platelets per microliter. When the count is less than 50,000 platelets per microliter, mild bleeding sometimes occurs. If the count is very low, less than 10,000 or 20,000 platelets per microliter, the risk for serious bleeding may occur. In rare cases, the number of platelets can be so low that dangerous internal bleeding occurs. Thrombocytopenia may occur in various conditions, such as the inherited bleeding disorders and acquired conditions (e.g., a side effect from medications). A low platelet count (thrombocytopenia) occurs may be due to not enough platelets made by bone marrow, deficiency in maintaining enough platelets in the blood, and/or abnormality in spleen which holds on too many platelets.

Conditions that cause a low platelet count (thrombocytopenia) include, for example, thrombotic thrombocytopenia purpura (TTP); disseminated intravascular coagulation (DIC); immune thrombocytopenia (ITP); an autoimmune disease; an enlarged spleen condition caused by cancer, severe liver disease, and a bone marrow deficiency; a viral or bacterial infection; and a side reaction to medicine.

Hemophilia A

Classic hemophilia or hemophilia A (also known as Factor FVIII deficiency) is an inherited bleeding disorder caused by a chromosome X-linked deficiency of FVIII and affects almost exclusively males. A mutation in the gene coding FVIII (i.e., the F8 gene) results in hemophilia A. The genetic mutations could cause absence or decreased synthesis of FVIII or abnormal protein synthesis (Hong et al., *Thrombosis Res.,* 2007, 119:1-13). The X-chromosome defect is transmitted by female carriers who are not themselves hemophiliacs. Due to random chromosome activation, some women carriers may range from asymptomatic to symptomatic depending on how much of their FVIII is inactivated.

Because blood does not clot properly without enough FVIII, the clinical manifestation of hemophilia A is an increased bleeding tendency, e. g., a small cut or injury carrying the risk of excessive bleeding. In addition, people with hemophilia may suffer from internal bleeding that can damage joints (including the knee, ankle, elbow and hip joints), muscles, organs, and tissues (e.g., soft tissue under the skin) over time. Hemophilia bleeding intensity depends on the level of FVIII deficiency. There are three forms of hemophilia A: mild, moderate or severe in individual patients (Table 1), which are determined based on deficient plasma FVIII (IU) (Bolton-Maggs and Pasi, *Lancet,* 2003, 361:1801-1809).

TABLE 1

Three forms of hemophilia

| Form of hemophilia | FVIII activity (IU/ml) | Main symptoms |
|---|---|---|
| mild | >0.05 but <0.50 (>5-50% of normal range) | Excessive bleeding after injuries, trauma, accidents, tooth extractions, surgeries |
| moderate | 0.01-0.05 (1-5% of normal range) | Joint and muscle bleedings following mild trauma; excessive bleeding after injuries, trauma, accidents, tooth extractions, surgeries |
| severe | <0.01 (<1% of normal range) | Spontaneous joint and muscle bleedings; excessive bleeding after injuries, trauma, accidents, tooth extractions, surgeries |

*IU: international unit

With regard to mild inherited bleeding disorders, bleeding symptoms also occur in otherwise healthy individuals. Although patients with mild bleeding disorders may not often suffer from bleeding in daily life, problems may occur after a hemostatic challenge, including but not limited to trauma, dental extractions and surgery.

The treatment of hemophilia A mainly focuses on increasing blood activity of deficient coagulation factor VIII with factor substitute, in order to inhibit and/or prevent active bleedings in patients. Current available therapeutics include human plasma derived lyophilized FVIII concentrates and recombinant coagulation factors produced by genetically engineered cells. FVIII concentrates have a short half-life in plasma, with an average of about 12 hours in adults, ranging in individual patients with hemophilia A between 6 hours and 29 hours, and even shorter in younger children. FVIII substitute treatment for hemophilia often requires frequent intravenous injections of therapeutics.

For patients with severe hemophilia A, an increased amount and dosing intervals are required for prophylactic treatment.

Several technologies are developing to extend the half-life of FVIII in the blood. As the vast majority of plasma FVIII circulates in a high-affinity complex with VWF, FVIII is mostly cleared while not coupled to VWF. It has been supported by studies showing that FVIII in hemophilia patients is significantly influenced by plasma VWF levels. For example, Valentino has shown that the FVIII half-life is significantly longer in patients with elevated VWF levels (Valentino et al., *Haemophilia,* 2014, 20:607-615). Targeting VWF chaperon to increase plasma FVIII-VWF complex levels may provide alternative strategies to extend half-life of FVIII in plasma.

In accordance with the present disclosure, VWF targeting agents can bind to VWF and extend the half-life of VWF, thereby extending the half-life of FVIII.

Von Willebrand's Disease (VWD)

Although deficiencies of Factor VIII (hemophilia A) and Factor IX (hemophilia B) are well recognized, von Willebrand disease (VWD) is much more common. Deficiencies in VWF (e.g., quantitatively reduced, functional defect, or completely missing) lead to different types of VWD. VWD can affect both males and females. Conversely, abnormally elevated VWF concentrations or function can also cause severe medical disorders like venous thromboembolic disease (VTE). VWD is classified into three different types (Types 1, 2, and 3), based on the levels of VWF and FVIII activity in the blood.

VWD Type 3 is the most severe and least common form with complete deficiency of VWF. Patients with Type 3 VWD have little or no VWF in their blood. The amount of FVIII in the blood also drops to low levels without VWF to act as a carrier. Type 3 VWD patients have trouble making both a platelet plug and a fibrin clot. VWD Type 3 patients have spontaneous bleedings into their joints and muscles, frequent bleeding from their noses and mouths. Women with Type 3 VWD may have long menstrual periods with very heavy bleeding.

VWD Type 2 relates to qualitative defects of VWF and can be as severe as VWD Type 3 in some patients, which include four subtypes: Types 2a, 2b, 2m and 2n. Type 2a is caused by defects in VWF multimerization due to the wrong size of the VWF protein. The abnormal VWF multimers stop the platelets from making a good platelet plug. In Type 2b, the VWF protein is abnormally active with variants of spontaneous platelet binding. The attachment of VWF causes the body to quickly get rid of the platelets, which causes a shortage of both platelets and VWF in the blood. Type 2m is caused by VWF defects in ligand binding with intact multimers. In Type 2n, VWF has defects in FVIII binding, failing to act as the carrier and protector of FVIII. The level of FVIII in the blood is low because of lacking enough VWF to keep it from being degradation. A Type 2n VWD patient can appear to have mild hemophilia with some of the same symptoms. VWD Type 2b in particular results from a mutation in the A1 domain of VWF causing constitutive activation of A1 domain binding to the GPIb receptor on platelets, leading to a consumptive deficiency of VWF, FVIII, and platelets.

VWD Type 1 is the mildest and most common form accounting for up to 85% pf VWD (reviewed by Robertson et al., *Pediatr Clin North Am.,* 2008, 55(2): 377-392), which relates to a quantitative loss of VWF but with qualitatively normal VWF. Because there is not enough VWF in the blood, a lower level of FVIII may be seen in Type 1. A small number of patients with Type 1 VWD can have severe bleedings. VWD Type 1 is a very heterogeneous family of genetic defects representing 85 unique SNPs at last count and has only partial deficiency of VWF. For example, type Vicenza variant of VWD Type 1 is characterized by a low plasma VWF level and supranormal VWF multimers, caused by increased rate of VWF clearance (Alessandra et al., Blood 2002, 99(1): 180-184).

Other Rare Bleeding Disorders

Deficiencies in other coagulation factors could cause rare bleeding disorders, e.g., rare factor deficiencies including Factor I, II, V, VII, X, XI, XII and XIII deficiency. In additional hereditary disorders, other bleeding disorders may be acquired, e.g., platelet disorders which are the most common cause of acquired bleeding disorder.

Currently, the standard treatment of Hemophilia A and VWD involves frequent intravenous infusions of FVIII and VWF preparations or concentrates comprising a complex of FVIII and VWF derived from the plasmas of human donors, recombinant FVIII preparations, or recombinant VWF preparations. In severe hemophilia A patients, FVIII injection is used for prophylactic treatment. Because of the short plasma half-life of FVIII, patients have to be administered intravenously about 3 times per week. VWD can be treated by replacement therapy with concentrates containing VWF of plasmatic or recombinant origin. One approach to increase functional half-life of VWF is by PEGylation of VWF, which pegylated VWF by having an increased half-life would indirectly also enhance the half-life of FVIII present in plasma (PCT Application Publication No.: WO2006/071801; the contents of which are incorporated by reference in their entirety.) PEGylation of VWF antigen at specific sites can protect VWF from macrophage-mediated clearance in plasma (Fazavaza et al., *J. Thromb. Haemost.,* 2020; 18:1278-1290; the contents of which are incorporated herein by reference in their entirety).

It is highly desirable to create new treatments that can increase functional half-life of FVIII and VWF in patients with bleeding disorders (e.g., hemophilia and VWD), while drugs can be administered less frequently or by other less cumbersome and less painful means of administration.

The inventors of the present disclosure surprisingly found that a VWF targeting aptamer that is modified with PEG conjugation can increase the VWF and FVIII levels in the blood after a single dose treatment. The VWF targeting nucleic acid does not interfere the functionality of FVIII in plasma at any concentration, and at relatively low concentrations does not interfere with the function of VWF in plasma.

In accordance with the present disclosure, a VWF targeting agent is provided to bind to VWF in plasma and block its clearance, thereby increasing half-life of the VWF-FVIII complex in the plasma. The VWF targeting agent can be used to treat a hereditary bleeding disease, in particular, hemophilia A and VWD (e.g., Type 1, Vicenza subtype, Type 2 including subtypes 2a, 2b, 2m and 2n, and Type 3).

VWF Targeting Agents

As used herein, the term "targeting agent" refers to an agent that specifically binds to and interacts with a molecule of interest. A VWF targeting agent is an agent that binds to VWF, directly or indirectly through another agent, to regulate VWF biologic activities (also referred to as "VWF binding agent), e.g., interaction of VWF with FVIII and half-life of VWF and FVIII-VWF complex. In general. the targeting agent may be an antibody, a nanobody, a peptide, an oligonucleotide, an RNA (e.g., siRNA, microRNA), a synthetic polynucleotide (e.g., an aptamer), or a small molecule that can bind to VWF. The VWF targeting agent also includes an agent that binds to VWF, thereby blocking the clearance mechanism. In some embodiments, the VWF targeting agent can be used for treatment of bleeding disorders, particularly hemophilia A and VWD. The VWF targeting agent may also be used for blocking VWF clearance in the blood.

In some embodiments, the VWF targeting agents may be nucleic acid based, particularly aptamers that bind to VWF, and variants thereof. In some examples, a VWF binding agent is an aptamer or salt thereof. Aptamers are short (i.e., typically 12-80 nucleotides in length) single-stranded nucleic acid polymers that bind with high affinity and specificity to VWF. The aptamer is a synthetic polynucleotide that can be isolated using the Systematic Evolution of Ligands by Exponential Enrichment (SELEX) process.

Aptamers

An aptamer is a biomolecule that binds to a specific target molecule and modulates the target's activity, structure, or function. Aptamers often are referred to as "chemical antibodies," having similar characteristics as antibodies. An aptamer can be nucleic acid or amino acid based, i.e., either a nucleic acid aptamer or peptide aptamer. Nucleic acid aptamers have specific binding affinity to target molecules through interactions other than classic Watson-Crick base pairing. Nucleic acid aptamers are capable of specifically binding to selected targets and, through binding, block their targets' ability to function. Aptamers of the present disclosure are synthetic oligonucleotides. A typical nucleic acid aptamer is approximately 10-15 kDa in size, binds its target with sub-nanomolar affinity, and discriminates against closely related targets. A target of a nucleic acid aptamer may be but is not limited to, a protein, a nucleic acid molecule, a peptide, a small molecule and a whole cell.

Nucleic acid aptamers may be ribonucleic acid (RNA), deoxyribonucleic acid (DNA), or mixed ribonucleic acid and deoxyribonucleic acid (DNA/RNA hybrid). Aptamers may be single stranded. A suitable nucleotide length for an aptamer ranges from about 15 to about 150 nucleotide (nt), and in various other preferred embodiments, 15-30 nt, 20-25 nt, 20-45 nt, 30-100 nt, 30-60 nt, 25-70 nt, 25-60 nt, 40-60 nt, 25-40 nt, 30-40 nt, any of 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 nt, or 30-50 nt, 40-70 nt, or 50-100 nt in length. However, the sequence can be designed with sufficient flexibility such that it can accommodate interactions of aptamers with targets.

As used herein, the terms "nucleic acid," "polynucleotide," "oligonucleotide" are used interchangeably. A nucleic acid molecule is a polymer of nucleotides consisting of at least two nucleotides covalently linked together. A nucleic acid molecule is a DNA (deoxyribonucleotide), an RNA (ribonucleotide), as well as a recombinant RNA and DNA molecule or an analogue of DNA or RNA generated using nucleotide analogues. The nucleic acids may be single stranded or double stranded, linear or circular. The term also comprises fragments of nucleic acids, such as naturally occurring RNA or DNA which may be recovered using the extraction methods disclosed, or artificial DNA or RNA molecules that are artificially synthesized in vitro (i.e., synthetic polynucleotides). Molecular weights of nucleic acids are also not limited, may be optional in a range from several base pairs (bp) to several hundred base pairs, for example from about 2 nucleotides to about 1,0000 nucleotides, or from about 10 nucleotides to 5,000 nucleotides, or from about 10 nucleotides to about 1,000 nucleotides.

The term "nucleotide (nt)" refers to the monomer of nucleic acids, a chemical compound comprised of a heterocyclic base, a sugar and one or more phosphate groups. The base is a derivative of purine and pyrimidine and the sugar is a pentose, either deoxyribose or ribose.

As used herein, the term "modification" refers to the technique of chemically reacting a nucleic acid, e.g., an oligonucleotide, with chemical reagents. A nucleic acid may be modified in the base moiety, sugar moiety or phosphate backbone. The modifications include, but are not limited to, 2'-position sugar modifications, 5-position pyrimidine, modifications, 8-position purine modifications, modifications at exocyclic amines, substitution of 4-thiouridine, substitution of 5-bromo or 5-iodo-uracil, backbone modifications, phosphorothioate or alkyl phosphate modifications, methylations, unusual base-pairing combinations such as the isobases isocytidine and isoguanidine and the like. Modifications can also include 3' and 5' modifications such as capping. The nucleic acid molecule may also be modified by conjugation to a moiety having desired biological properties. Such moiety may include, but is not limited to, compounds, peptides and proteins, carbohydrates, antibodies, enzymes, polymers, drugs and fluorophores. In some examples, the polynucleotide is conjugated to a lipophilic compound such as cholesterol, dialkyl glycerol, diacyl glycerol, or a nonimmunogenic, high molecular weight compound or polymer such as PEG (polyethylene glycol) or other water soluble pharmaceutically acceptable polymers including, but not limited to, polyaminoamines (PAMAM) and polysaccharides such as dextran, or polyoxazolines (POZ). The modifications may be intended, for example, to increase the in vivo stability of nucleic acid molecules or to enhance or to mediate delivery of the molecules.

Aptamers may be either monovalent or multivalent. Aptamers may be monomeric, dimeric, trimeric, tetrameric or other higher multimeric. Individual aptamer monomers may be linked to form multimeric aptamer fusion molecules. As a non-limiting example, a linking oligonucleotide (i.e., linker) may be designed to contain sequences complementary to both 5'-arm and 3'-arm regions of random aptamers to form dimeric aptamers. For trimeric or tetrameric aptamers, a small trimeric or tetrameric (i.e., a Holliday junction-like) DNA nanostructure will be engineered to include sequences complementary to the 3'-arm regions of the random aptamers, therefore creating multimeric aptamer fusion through hybridization. In addition, 3 to 5 or 5 to 10 dT rich nucleotides can be engineered into the linker polynucleotides as a single stranded region between the aptamer-binding motifs, which offers flexibility and freedom of multiple aptamers to coordinate and synergize multivalent interactions with cellular ligands or receptors. Alternatively, multimeric aptamers can also be formed by mixing biotinylated aptamers with streptavidin.

As used herein, the term "multimeric aptamer" or "multivalent aptamer" refers to an aptamer that comprises multiple monomeric units, wherein each of the monomeric units can be an aptamer on its own. Multivalent aptamers have multivalent binding characteristics. A multimeric aptamer can be a homomultimer or a heteromultimer. The term "homomultimer" refers to a multimeric aptamer that comprises multiple binding units of the same kind, i.e., each unit binds to the same binding site of the same target molecule. The term "heteromultimer" refers to a multimeric aptamer that comprises multiple binding units of different kinds, i.e., each binding unit binds to a different binding site of the same target molecule, or each binding unit binds to a binding site on different target molecule. Thus, a heteromultimer can refer to a multimeric aptamer that binds to one target molecule at different binding sites or a multimeric aptamer that binds to different target molecules. A heteromultimer that binds to different target molecules can also be referred to as a multi-specific multimer.

Aptamers can be generated against a target molecule (e.g., VWF) using a process called either in vitro selection (Ellington and Szostak, Nature, 1990; 346:818-822) or SELEX (Tuerk and Gold, Science, 1990, 249:505-510). This method allows the in vitro evolution of nucleic acid molecules with highly specific binding to target molecules. The SELEX method is described in, for example, U.S. Pat. Nos. 7,087,735, 5,475,096 and 5,270,163; the contents of each of which are incorporated herein by reference in their entirety. Nucleic acid aptamers can be synthesized using methods well-known in the art. For example, the disclosed aptamers may be synthesized using standard oligonucleotide synthesis technology known in the art.

VWF Aptamers

In accordance with the present disclosure, VWF targeting agents are polynucleotides, salts thereof, or derivatives thereof, that target VWF to, e.g., regulate the interaction between VWF and FVIII in plasma. In some embodiments, VWF targeting agents are aptamers specifically binding to VWF. Accordingly, anti-VWF aptamers are also referred to as "VWF binding agents".

The synthetic polynucleotide, when binding to VWF, can block the clearance mechanism in the blood, thereby increasing the levels of VWF antigen in the blood. The blockage could increase the level of Factor VIII in the blood as the FVIII-VWF complex is protected from protein degradation.

In some embodiments, the synthetic polynucleotide binding to VWF may be 15 to 50 nucleotides in length, or 20 to 30 nucleotides in length (e.g., 20 nucleotides, 21 nucleotides, 22 nucleotides, 23 nucleotides, 24 nucleotides, 25 nucleotides, 26 nucleotides, 27 nucleotides, 28 nucleotides, 29 nucleotides, and 30 nucleotides in length). Said synthetic polynucleotide may further comprise a double stranded region. The double stranded region may be from about 6 to about 9 nucleotides. The double stranded region is formed by 6 nucleotides, or 7 nucleotides, or 8 nucleotides, or 9 nucleotides. Furthermore, the double stranded region is formed by 6 or more of the 3' and 5' nucleotides at or near the termini of the sequence.

In some embodiments, the synthetic polynucleotides may be chemically modified. Each nucleotide may contain at least one chemical modification. Such chemical modification may be at the sugar, nucleobase or inter-nucleoside linker of the synthetic polynucleotide. Modifications to the sugar may comprise but are not limited to 2'-amino, 2'-O-alkyl, 2'-fluoro, and 2'-O-methyl modification. As a non-limiting example, the synthetic polynucleotide targeting to VWF comprises 2'-O-methyl modification. In some embodiments, a terminal cap structure may be incorporated to the 3' and/or 5' termini of the synthetic polynucleotide. The cap structure includes 5'-5' inverted nucleotide cap at the 5' terminus of the synthetic polynucleotide and a 3'-3' inverted nucleotide cap at the 3' terminus of the synthetic polynucleotide. The cap structure may be an inverted deoxythymidine or amino group (NH2).

The synthetic polynucleotide may be further modified to comprise one or more conjugates such as a PEG (polyethylene glycol) moiety at the 5' or 3' termini of the synthetic polynucleotides. The PEG moiety may be of any size or branch configuration. PEGs can range in size from about 5 kD to about 200 kD. PEGs may be linear chain PEGs or branched PEGs with multiple PEG chains attached together. The 3'- and 5'-short PEG conjugates do not interfere with the binding specificity and they do not influence the target affinity of the synthetic polynucleotides.

In one embodiment, the VWF binding agent is a synthetic polynucleotide comprising at least 21 contiguous nucleotides of SEQ ID No.: 3 (5'GCCAGGGACCUAAGACA-CAUGUCCCUGGC-3'); the sequence is derived from an aptamer that binds specifically to VWF. In one embodiment, the VWF binding agent may be a synthetic polynucleotide comprising at least 21 contiguous nucleotides of SEQ ID No.: 3. Additionally, the synthetic polynucleotide may exhibit a double stranded region having at least 6 nucleotides, or at least 7 nucleotides, or at least 8 nucleotides, or at least 9 nucleotides. In one embodiment, the double stranded region of 6 or more nucleotides is at or near (e.g., within 1-10 nucleotides) the termini of the synthetic polynucleotide.

In some embodiments, the synthetic polynucleotide comprises an inverted deoxythymidine at the 3' terminus of the sequence. As a non-limiting example, the VWF targeting agent is a synthetic polynucleotide comprising the structure: mGmCmCmAmGmGmGmAmCmCmUmAmAmGmAm- CmAmCmAmUmGmUmCmCmCmU mGmGmC-idT (SEQ ID No.: 4) (BT99), where "NH" is a 5'-hexylamine linker phosphoramidite, "idT" is an inverted deoxythymidine, "mN" is a 2'-O-Methyl containing residue.

In some embodiments, the synthetic polynucleotide comprises an inverted deoxythymidine at the 3' terminus of the sequence and an amino group (NH2) at the 5' terminus of the sequence. As a non-limiting example, the VWF targeting agent is a synthetic polynucleotide comprising the structure: NH2-mGmCmCmAmGmGmGmAmCmCmUmAmAmG-mAmCmAmCmAmUmGmUmCmCmCmU mGmGmC-idT (SEQ ID No.: 5) (BT100), where "NH" is a 5'-hexylamine linker phosphoramidite, "idT" is an inverted deoxythymidine, "mN" is a 2'-O-Methyl containing residue.

In some embodiments, the synthetic polynucleotide binding to VWF further comprises a PEG moiety conjugated at the 5' terminus of the sequence. As a non-limiting example, the VWF targeting agent is a synthetic polynucleotide comprising the structure: PEG40K-NH-mGmCmC-mAmGmGmGmAmCmCmUmAmAmGmAmCmAmC-mAmUmGmUmCmCmCmU mGmGmC-idT (SEQ ID No.: 6) (BT200), where "NH" is a 5'-hexylamine linker phosphoramidite, "idT" is an inverted deoxythymidine, "mN" is a 2'-O-Methyl containing residue and "PEG" is a polyethylene glycol and PEG40K is a PEGylation moiety having a molecular weight of approximately 40 KDa.

The PEGylated BT200 specifically binds to the A1 domain of VWF in plasma, interfering its regulation and functionality (Zhu et al., J Thromb Haemost. 2020 May; 18(5):1113-1123; the contents of which are incorporated herein by reference in their entirety). One mechanism is that the binding of BT200 to VWF may protect the nucleic acid-protein complex from clearance by inhibiting the interaction of VWF with the macrophage low density lipoprotein receptor related protein-1 (LRP1) (Fazavana et al., *J Thromb Haemost.,* 2020, 1278-1290). In this regard, BT200 can be used as an anti-bleeding agent. The inventors of the present disclosure have found that at low doses, BT200 blocks the clearance of VWF Antigen from the circulation and leads to a sustained increase in concentrations of both VWF antigen (VWF Ag) and FVIII but has a negligible effect on the activity of either. At higher doses, BT200 blocks clearance of VWF and inhibits the activity of VWF but does not inhibit FVIII activity. Therefore, BT200 may be used to correct deficiency of VWF and/or FVIII in patients with hereditary bleeding disorders (e.g., VWD Type 1, Type 2b and Type 3).

BT200 by subcutaneous injections demonstrates an extended half-life, lasting 7-12 days in the circulation that provides good subcutaneous bioavailability (Zhu et al., *J Thromb Haemost,* 2020, 1113-1123).

In other embodiments, the VWF binding agents are aptamers comprising the sequence: PEG40K-NH-mGmGmGmAmCmCmUmAmAmGmAmCmAmCmA-mUmGmUmCmCmC-idT (ARC15105) (SEQ ID No.: 7), or the sequence: PEG20K-NH-mGmCmGmUdGdCdAmG-mUmGmCmCmU-mUmCmGmGmCdCmGsdTmGdCdGdGdTmGm CdCmUdCdCmGmUdCmAmCmGmCidT (ARC1779) (SEQ ID No.: 8), where "NH" is a 5'-hexylamine linker phosphoramidite, "idT" is an inverted deoxythymidine, "mN" is a 2'-O-Methyl containing residue, "dN" is a deoxynucleotide residue, "sdT" is a phosphorothioate deoxythymidine residue and "PEG" is a polyethylene glycol and PEG20K is a PEGylation moiety having a molecular weight of approximately 20 Kda.

In some embodiments, the VWF binding agent may include a synthetic polynucleotide having at least 50%, 55%, 60%, 65%, 70%, 75%, 80%, 90%, 95%, 96%, 97%, 98%, 99% or 100% sequence identity to SEQ ID No.: 3.

TABLE 2

VWF aptamers and variants

| Agent | Sequence (5'-3') and modifications | SEQ ID NO.: |
|---|---|---|
| VWF aptamer | GCCAGGGACCUAAGACACAUGUCCCUGGC | 3 |
| BT99 | mGmCmCmAmGmGmGmAmCmCmUmAmAmGmAmCm AmCmAmUmGmUmCmCmCmUmGmGmC-idT | 4 |
| BT100 | $NH_2$-mGmCmCmAmGmGmGmAmCmCmUmAmAmGm AmCmAmCmAmUmGmUmCmCmCmUmGmGmC-idT | 5 |
| BT200 | PEG40K-NH- mGmCmCmAmGmGmGmAmCmCmUmAmAmGmAmCm AmCmAmUmGmUmCmCmCmUmGmGmC-idT | 6 |
| ARC15105 | PEG40K-NH- mGmGmGmAmCmCmUmAmAmGmAmCmAmCmAmUm GmUmCmCmC-idT | 7 |
| ARC1779 | PEG20K-NH- mGmCmGmUdGdCdAmGmUmGmCmCmUmUmCmGm GmCdCmGsdTmGdCdGdGdTmGmCdCmUdCdCm GmUdCmAmCmGmCidT | 8 |

Pharmaceutical Compositions

In another aspect of the present disclosure, pharmaceutical compositions and formulations including any one of anti-VWF aptamers of the present disclosure are provided. The VWF binding agents are formulated in formulations suitable for administration to a subject in need. Formulations which are suitable for the pharmaceutical compositions of the present disclosure, particularly the nucleic acid-based compositions, are taught in International Patent Publication No. WO2013/090648 (Application PCT/US2012/069610), the contents of which are incorporated herein by reference in their entirety. Methods of making formulations are well known in the art, for example, in Remington: The Science and Practice of Pharmacy (20th ed., ed. A. R. Gennaro A R.), Lippincott Williams & Wilkins, 2000; the contents of which are incorporated herein by reference in their entirety.

Pharmaceutical compositions of the present disclosure may comprise at least one VWF targeting agent as active ingredient, e.g., BT200.

The compositions further include at least one pharmaceutically acceptable carrier, diluent or excipient, e.g., saline or distilled water. Optionally, the compositions may include excipients that stabilize the aptamer agent, thereby maintaining therapeutic activity of the agent. In some embodiments, the compositions may comprise excipients such as salts, sugars and alcohols that facilitate diffusion of the aptamer agent.

As non-limiting examples, excipients may include saccharides such as sucrose, trehalose, fructose, galactose, mannitol, dextran and glucose; poly-alcohols such as glycerol and sorbitol; proteins such as albumin; hydrophobic molecules such as oils; hydrophilic polymers such as polyethylene glycol; isomers such as diastereomers and enantiomers, mixtures of isomers, including racemic mixtures, salts, solvates, and polymorphs thereof.

In some embodiments, the composition may be in the form of liquid solutions or suspensions. In some cases, the composition is sterile for injection.

In some embodiments, the VWF targeting agents of the present disclosure are formulated for oral administration. Formulations may be in the form of tablets or capsules. In some embodiments, the VWF agents of the present disclosure are formulated for intranasal administration. Intranasal formulations may be in the form of powders, nasal drops, or aerosols. In some embodiments, the VWF agents of the present disclosure are formulated for parenteral administration. The formulations include only pharmaceutically acceptable excipients, diluents, carriers and adjuvants that are safe for parenteral administration to humans at the concentrations used, under the same or similar standards as for excipients, diluents, carriers and adjuvants deemed safe by the Federal Drug Administration or other foreign national authorities. The pharmaceutical formulation may be in a ready-to-use solution form, concentrated form, or a lyophilized preparation that may be reconstituted with a directed amount of diluent suitable for parenteral injection such as water, salt solution, or buffer solution. In some examples, the formulation is a stable aqueous pharmaceutical formulation that remains within its physical, chemical, microbiological, therapeutic and toxicological specifications throughout its shelf life. In some embodiments, the VWF targeting agents of the present disclosure are formulated for inhalation.

In some embodiments, the VWF targeting agents of the present disclosure may be formulated for controlled release of the active agent. As non-limiting examples, formulations for controlled release may comprise biocompatible polymers. The choice of the polymer depending on the rate of drug release required in a particular treatment regimen. Biocompatible polymers suitable for sustained release include, but are not limited to, biodegradable polymers such as polyamides such as poly(amino acids) and poly(peptides); polyesters such as poly(lactic acid), poly(glycolic acid), poly(lactic-co-glycolic acid), and poly(caprolactone); poly (anhydrides); polyorthoesters; polycarbonates and chemical derivatives thereof; copolymers and mixtures thereof. Biocompatible polymers may include non-degradable polymers such as polysaccharides; polyethers (e.g., poly(ethylene oxide), poly(ethylene glycol), and poly(tetramethylene oxide)); vinyl polymers (e.g., polyacrylates, acrylic acids, poly(vinyl alcohol), poly(vinyl pyrolidone), and poly(vinyl acetate)); polyurethanes; cellulose-based polymers (e.g., cellulose, alkyl cellulose, hydroxyalkyl cellulose, cellulose ethers, cellulose esters, nitrocellulose, and cellulose acetates); polysiloxanes and other silicone derivatives. The sustained release of the agents may last for more than two months, for one month, for three weeks, for two weeks, for one week, for six days, for five days, for four days, for three days, for two days, or for one day. The amount of the agents in the compositions for sustained release may comprise about 0.1% to about 30%, or about 0.1% to about 10%, or about 1% to about 10%, or about 0.5% to about 5% (w/w) of the formulation, e.g., about 0.1% (w/w), about 0.2% (w/w), about 0.5% (w/w), about 1.0% (w/w), about 2.0% (w/w), about 5.0% (w/w), about 10% (w/w), about 12% (w/w), about 15% (w/w), about 20% (w/w), about 25% (w/w), or about 30% (w/w) of the formulation.

In some embodiments, the VWF targeting agents are formulated as injectable thermosensitive gel formulations. As used herein, the term "thermosensitive gel formulation" means a formulation that exists as a mobile viscous liquid at low temperatures but forms a rigid semisolid gel at higher temperatures. Specifically, the formulation is liquid at room temperature or at lower temperature, but gels once injected, thus producing a depot of drug at the injection site. The formulations may contain thermo-sensitive polymers. As used herein, the term "gel" refers to the semi-solid phase that spontaneously occurs as the temperature of the thermo-sensitive polymer solution is raised to or above the gelation temperature of the polymer. Exemplary thermo-sensitive polymers may include PLGA-PEG-PLGA triblock copolymer, poloxamer, Pluronic acid F127, and polyoxyethylene-polyoxypropylene (PEO-PPO) block copolymers. In some embodiments, the gelation temperature of the formulation is from about 30° C. to about 40° C.

In some embodiments, the VWF targeting agents may be encapsulated with liposomal formulations. As used herein, the term "liposome" means a formulation consisting of at least one lipid bilayer membrane enclosing an aqueous internal compartment. Liposomes may be small unilamellar vesicles (SUVs) having a single membrane and typically range between 0.02 and 0.05 μm in diameter, or large unilamellar vesicles (LUVs) that are typically larger than 0.05 μm, or oliglamellar large vesicles having multiple, usually concentric, membrane layers that are typically larger than 0.1 μm. Liposomes are formulated to carry the VWF agents contained within the aqueous interior space or partitioned into the lipid bilayer.

In some embodiments, the VWF targeting agents may be formulated as implantable solid formulations, or coated to the surface of implants (e.g., stent).

The concentrations of the VWF targeting agent in the pharmaceutical formulation vary depending on a variety of factors, including the dosage of the drug to be administered, and the route of administration.

Treatment, Administration and Dosage

In one aspect, the VWF targeting agents of the present disclosure may be used for treating a bleeding disorder, and more specifically for treating a hereditary bleeding disorder, e.g., hemophilia A (mild, moderate and severe hemophilia), and VWD (Type 1, Type 2b and Type 3).

In some embodiments, the VWF targeting agents of the present disclosure may be used in the therapy and prophylactic treatment of a bleeding disorder. As used herein, the term "prophylactic treatment" is commonly referred to as a preventive treatment to avoid bleeding, by regular infusion of blood coagulation factor concentrates to a patient with a bleeding disorder. Patients with a severe form of the bleeding disorder (e.g., severe hemophilia and VWD Type 3) who receive the prophylactic treatment may experience reduced risk of bleeding and less joint damages.

In some embodiments, the VWF targeting agents of the present disclosure may be used in combination with coagulation factor replacement therapy (also known as coagulation factor substitute). For example, the VWF targeting agents may be used in combination with FVIII replacement therapy for treating hemophilia A, such as mild hemophilia, moderate hemophilia and severe hemophilia, in a patient. In one preferred embodiment, the patient is diagnosed with severe hemophilia.

Regular treatment with FVIII prophylaxis can significantly protect against spontaneous bleeding symptoms in patients with hemophilia A, particularly with severe hemophilia. Plasma derived FVIII concentrates and recombinant FVIII preparations are currently available treatments of hemophilia A. As the short circulatory half-life of FVIII in the blood requires regular intravenous FVIII infusions to maintain therapeutic plasma FVIII levels, the dosing schedule clinically has important implications for patient compliance. Recent effort focuses on developing new approaches to extend half-lives of FVIII substitute, e.g., modification of recombinant FVIII. However, clinical studies with modified recombinant FVIII molecules have demonstrated more moderate increases in half-life (≈1.5-fold) than for wild-type recombinant FVIII (Pipe et al., *Blood,* 2016, 128:2007-2016).

It is recently reported that VWF peptide can effectively prolong endogenous FVIII survival in VWF-deficient mice and that extending the half-life of plasma VWF carrier fragment can result in a significant prolongation in FVIII half-life in VWF-deficient mice (Yee et al., *Blood,* 2014, 124:445-452). Agents that can elevate the VWF levels may be used for extending the half-life of FVIII in the blood, thereby elevating the FVIII levels in patients with low FVIII activity (e.g., hemophilia and VWD). The studies performed by the inventors demonstrated that administration of a VWF binding agent, BT200 can increase the VWF and FVIII levels in the blood, in a dose-dependent manner. BT200 binds to VWF and prevents VWF from clearance in the blood. Elevated VWF forms FVIII-VWF complexes, thereby increasing the FVIII levels in the blood.

In some embodiments, the VWF targeting agents of the present disclosure may be used in combination with a recombinant FVIII preparation, or plasma derived FVIII concentrates, to extend the half-life of FVIII in the blood of a hemophilia patient. The patient may have mild, moderate or severe hemophilia. In particular, the patient has severe hemophilia.

In some embodiments, the VWF targeting agents of the present disclosure may be used in combination with VWF replacement therapy for treating VWD, particularly VWD Type 3 and VWD Type 2 and VWD Type 1. In some examples, the VWF targeting agents may be used in combination with a VWF replacement preparation. The VWF replacement preparation may be a plasma-derived factor concentrate containing both FVIII and VWF (i.e., a FVIII/VWF concentrate), and a recombinant VWF preparation. As a non-limiting example, the recombinant VWF preparation may be Vonicog alfa, rVWF that is produced in genetically altered CHO cells expressing both VWF and FVIII (Turecek et al., *Hamostaseologie,* 2009, 29(Suppl.):S32-38).

In other examples, the present VWF targeting agents may be used in combination with DDAVP treatment. The VWF targeting agent may stabilize and increase the endogenous VWF and FVIII levels released by stimulation of DDAVP.

In some embodiments, the VWF targeting agents of the present disclosure may be used to maintain adequate VWF levels in the blood to protect FVIII from degradation. VWF may be endogenous, released by in vivo VWF producing cells, or exogenous, infused with in vitro VWF substitute. FVIII may be endogenous or exogenous.

In some embodiments, the VWF targeting agents may be used to increase platelet counts in a patient with VWD Type 2b, in particular, the VWD Type 2b patient with thrombocytopenia which is formed due to platelet aggregation. The present VWF targeting agent such as BT200 may raise platelet counts in the blood.

The present VWF targeting agent can increase platelet counts in the blood. Accordingly, a VWF targeting agent, can be used to treat thrombocytopenia, a condition in which a patient has a low platelet count in the blood. Thrombocytopenia may occur in various conditions, e.g., a bone marrow disorder, a side effect from medications, an enlarged spleen associated with cancer and severe liver disease, an autoimmune disease, a condition by exposing a toxic chemical, and an infection.

In particular, BT200 can maintain sustained elevation of VWF and FVIII levels in the blood.

In some embodiments, the present VWF targeting agents, compositions and methods may be used to treat other rare deficiencies in clotting components. Rare inherited bleeding disorders (RBDs) include, for example, deficiencies of coagulation factors fibrinogen, FII, FV, combined FV and FVIII, FVII, FX, FXI, FXIII, and congenital deficiency of vitamin K-dependent factors (VKCFDs).

In accordance with the present disclosure, the methods comprise administering to the subject a therapeutically effective amount of a pharmaceutical composition comprising at least one VWF targeting agent. In some examples, the targeting agent is a VWF binding agent. The VWF binding agent is an antibody, a nanobody, a peptide, an oligonucleotide, an RNA (e.g., siRNA, microRNA), a synthetic polynucleotide (e.g., an aptamer), or a small molecule. In some embodiments, The VWF binding agent is a synthetic polynucleotide selected from the group consisting of SEQ ID No.: 3, BT99 (SEQ ID No.: 4), BT100 (SEQ ID No.: 5), BT200 (SEQ ID No.: 6), ARC15105 (SEQ ID No.: 7), and ARC1779 (SEQ ID No.: 8) and variants thereof. In one preferred embodiment, the VWF binding agent is BT200 (SEQ ID No.: 6).

The VWF targeting agent may increase the levels of FVIII and VWF in the blood of the subject being treated with said agent. The VWF targeting agent may raise platelet counts in the subject as well.

As a non-limiting example, the VWF targeting agent is BT200 (SEQ ID No.: 6).

In accordance with the present disclosure, the treatment regimen such as doses, dose-response relationship, loading and maintenance doses and dosing schedules (such as intervals and timing), administration routes, formulations, etc. are discussed and determined.

In some embodiments, the VWF targeting agents may be administered to the subject in need in any administration routes. The agents and compositions may be formulated for administration by parental administration or enteral administration, or other appropriate routes. Parental administration may be performed by injection, or by the insertion of an indwelling catheter, including but not limited to intravenous (IV), intramuscular (IM), subcutaneous (SC), epicutaneous injection, peridural injection, intracerebral (into the cerebrum) administration, intracerebroventricular (into the cerebral ventricles) administration, extra-amniotic administration, nasal administration, intra-arterial, intracardiac, intraosseous infusion (IO), intraperitoneal infusion or injection, transdermal diffusion, enteral and gastrointestinal routes, topical administration and oral routes.

As a non-limiting example, the VWF targeting agent is administered by subcutaneous injection.

The therapeutically effective dosage of a medicine varies from patient to patient and depends upon factors such as the age and condition of the patient and the route of delivery. Such dosages can be determined in accordance with routine pharmacological procedures known to those skilled in the art. Factors that may influence the dosage required to effectively treat a subject, include but are not limited to the severity of the disease or disorder, previous treatments, the general health and/or age of the subject, and other diseases present. Moreover, treatment of a subject with a therapeutically effective amount of a therapeutic polynucleotide disclosed herein can include a single treatment or can include a series of treatments. The effective dosage of a therapeutic polynucleotide disclosed herein used for treatment may increase or decrease over the course of a particular treatment. Changes in dosage may result and become apparent from the results of diagnostic assays as described herein.

In some embodiments, a therapeutically effective amount or dosage of the VWF targeting agent may range from about 0.001 μg/kg or 0.01 μg/kg to about 250 mg/kg or 500 mg/kg body weight, with other ranges including but not limited to, about 0.01 μg/kg to 100 mg/kg body weight, about 0.01 μg/kg to 50 mg/kg body weight, about 0.1 μg/kg to 20 mg/kg body weight, about 0.1 μg/kg to 10 mg/kg body weight, about 1 μg/kg to 100 mg/kg body weight, about 1 μg/kg to 50 mg/kg body weight, about 10 μg/kg to 100 mg/kg body weight, about 10 μg/kg to 50 mg/kg body weight, about 20 μg/kg to 100 mg/kg body weight, about 20 μg/kg to 50 mg/kg body weight, about 1 mg/kg to 100 mg/kg body weight, about 1 mg/kg to 50 mg/kg body weight, or about 20 mg/kg to 50 mg/kg body weight. The skilled artisan will appreciate that certain factors may influence the dosage required to effectively treat a subject, including but not limited to the severity of the disease or disorder, previous treatments, the general health and/or age of the subject, and other diseases present.

In some embodiments, the pharmaceutical compositions may be administered to the subject in need in a single dose. A single dose of BT200 may be 0.1 mg, 0.2 mg, 0.5 mg, 1.0 mg, 1.5 mg, 2.0 mg, 2.5 mg, 3.0 mg, 3.5 mg, 4.0 mg, 4.5 mg, 5.0 mg, 5.5 mg, 6.0 mg, 6.5 g, 7.0 mg, 7.5 mg, 8.0 mg, 8.5 mg, 9.0 mg, 10.0 mg, 11.0 mg, 12.0 mg, 13.0 mg, 14.0 mg, 15.0 mg, 16.0 mg, 17.0 mg, 18.0 mg, 19.0 mg, 20.0 mg, 21.0 mg, 22.0 mg, 23.0 mg, 24.0 mg, 25.0 mg, 26.0 mg, 27.0 mg, 28.0 mg, 29.0 mg, 30.0 mg, 31.0 mg, 32.0 mg, 33.0 mg, 34.0 mg, 35.0 mg, 36.0 mg, 37.0 mg, 38.0 mg, 39.0 mg, 40.0 mg, 41.0 mg, 42.0 mg, 43.0 mg, 44.0 mg, 45.0 mg, 46.0 mg, 47.0 mg, 48.0 mg, 49.0 mg, 50.0 mg, 51.0 mg, 52.0 mg, 53.0 mg, 54.0 mg, 55.0 mg, 56.0 mg, 57.0 mg, 58.0 mg, 59.0 mg, 60.0 mg, 61.0 mg, 62.0 mg, 63.0 mg, 64.0 mg, 65.0 mg, 66.0 mg, 67.0 mg, 68.0 mg, 69.0 mg, 70.0 mg, 71.0 mg, 72.0 mg, 73.0 mg, 74.0 mg, 75.0 mg, 76.0 mg, 77.0 mg, 78.0 mg, 79.0 mg, 80.0 mg, 81.0 mg, 82.0 mg, 83.0 mg, 84.0 mg, 85.0 mg, 86.0 mg, 87.0 mg, 88.0 mg, 89.0 mg, 90.0 mg, 91.0 mg, 92.0 mg, 93.0 mg, 94.0 mg, 95.0 mg, 96.0 mg, 97.0 mg, 98.0 mg, 99.0 mg, or 100.0 mg.

In one preferred embodiment, the single dose of BT200 is about 1.0 mg to 10.0 mg, or about 1.0 mg to 6.0 mg.

In some embodiments, the pharmaceutical compositions may be administered to the subject in need in multiple doses. The dosing schedules provided herein are safe and effective to prevent bleeding. As a non-limiting example, a patient may be treated with the present VWF targeting agent one time per week. It will also be appreciated that the effective dosage of an agent used for treatment may increase or decrease over the course of a particular treatment. The agents of the present disclosure can be administered simultaneously or separately.

In one preferred embodiment, a multiple dosing regimen is provided, including a loading dose of BT200 and sequential maintenance doses of BT200. The loading dose and maintenance doses may range from, but are not limited to, 0.1 mg to 10.0 mg of BT200, or 1.0 mg to 6.0 mg of BT200.

As non-limiting examples, BT200 may be dosed at 0.1 mg, 0.2 mg, 0.5 mg, 1.0 mg, 1.5 mg, 2.0 mg, 2.5 mg, 3.0 mg, 3.5 mg, 4.0 mg, 4.5 mg, 5.0 mg, 5.5 mg, 6.0 mg, 6.5 mg, 7.0 mg, 8.0 mg, 9.0 mg, 10.0 mg, 15 mg, or 20 mg. In some embodiments, BT200 may be dosed at 3.0 mg. 6.0 mg, 9.0 mg or 10.0 mg.

In some embodiments, the VWF targeting agents or pharmaceutical formulations thereof may be administered to a patient about every day, about every other day, about every 3 days, about every 4 days, about every 5 days, about every 6 days, about every 7 days, about every 8 to 10 days, about every 11 to 14 days, or about every three weeks to the patient in need thereof. In one embodiment, the VWF agent or pharmaceutical formulations thereof can be administered about every 7 days.

In some examples, the VWF targeting agents or pharmaceutical formulations thereof can be administered as a single time administration. In other examples, administration of the VWF targeting agents or pharmaceutical formulations thereof can continue for about 1 week, about 2 weeks, about 3 weeks, about 4 weeks, about 5 weeks, about two months, about three to four months, about four to six months, or about one year. In some examples, administration of the VWF agents or pharmaceutical formulations thereof is about every 7 days for about 5 weeks. In certain embodiments, administration can be intermittent after, for example, about 4 weeks, or about 5 weeks. As a non-limiting example, a subject in need may be treated once a week for about 5 weeks and then treated about 3 to about 4 times over the following years. In some embodiments, the VWF agents or pharmaceutical formulations thereof may be administered to the subject intermittently to maintain the patency of a vessel, or to keep VWF at certain levels. Dosing schedules and use of methods in combination with other bleeding prevention therapies are included.

In accordance with the present disclosure, the VWF targeting agent may be administered once every other day, once every three days, once every five days, once a week, or once every other week. In one preferred embodiment, the VWF targeting agent may be administered at least one loading dose and at least one maintenance dose. The loading dose and maintenance dose may be the same or different. As a non-limiting example, the VWF targeting agents or pharmaceutical formulations thereof can be administered with 2 loading doses, and 3 maintenance doses every 7 days.

EQUIVALENTS AND SCOPE

Those skilled in the art will recognize or be able to ascertain using no more than routine experimentation, many equivalents to the specific embodiments in accordance with the disclosure described herein. The scope of the present disclosure is not intended to be limited to the above Description, but rather is as set forth in the appended claims.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The disclosure includes embodiments in which exactly one member of the group is present in, employed in, or otherwise relevant to a given product or process. The disclosure includes embodiments in which more than one, or the entire group members are present in, employed in, or otherwise relevant to a given product or process.

It is also noted that the term "comprising" is intended to be open and permits but does not require the inclusion of additional elements or steps. When the term "comprising" is used herein, the term "consisting of" is thus also encompassed and disclosed.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the disclosure, to the tenth of the unit of the lower limit of the range, unless the context clearly dictates otherwise.

In addition, it is to be understood that any particular embodiment of the present disclosure that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the disclosure (e.g., any antibiotic, therapeutic or active ingredient; any method of production; any method of use; etc.) can be excluded from any one or more claims, for any reason, whether or not related to the existence of prior art.

It is to be understood that the words which have been used are words of description rather than limitation, and that changes may be made within the purview of the appended claims without departing from the true scope and spirit of the disclosure in its broader aspects.

While the present disclosure has been described at some length and with some particularity with respect to the several described embodiments, it is not intended that it should be limited to any such particulars or embodiments or any particular embodiment, but it is to be construed with references to the appended claims so as to provide the broadest possible interpretation of such claims in view of the prior art and, therefore, to effectively encompass the intended scope of the disclosure.

EXAMPLES

Example 1: Dosing Window of BT200 for Treating a Bleeding Disorder

The blood levels of Factor VIII and VWF were measured after a single dose of BT200 at a dose ranging from 0.18 mg up to 48 mg in healthy volunteers. One week after dosing, the blood levels of Factor VIII and VWF antigen were increased in a dose- and time-dependent manner (as shown in Table 3 (Factor VIII) and Table 4 (VWF antigen). In the description column of Table 3 and Table 4, the description includes the cohort number, the therapeutic given and the patient identifier. For example, "1-BT200-A" means the patient A of cohort 1 which was given BT200 and "1-Control-A" means patient A of the control group.

TABLE 3

| Factor VIII Activity | | | | |
|---|---|---|---|---|
| Description | Visit | Result (%) | Absolute Change | Relative Change |
| 1-BT200-A | Day 0, 1 h prior IMP | 59 | — | — |
| 1-BT200-A | Day 2 | 138 | 79 | 1.34 |
| 1-BT200-A | Day 7 | 101 | 42 | 0.71 |
| 1-BT200-A | Day 14 | 93 | 34 | 0.58 |
| 1-BT200-A | Day 21 | 117 | 58 | 0.98 |
| 1-BT200-A | Day 28 | 69 | 10 | 0.17 |
| 1-BT200-B | Day 0, 1 h prior IMP | 92 | — | — |
| 1-BT200-B | Day 2 | 103 | 11 | 0.12 |
| 1-BT200-B | Day 7 | 79 | −13 | −0.14 |
| 1-BT200-B | Day 14 | 97 | 5 | 0.05 |
| 1-BT200-B | Day 21 | 130 | 38 | 0.41 |
| 1-BT200-B | Day 28 | 147 | 55 | 0.6 |
| 1-BT200-C | Day 0, 1 h prior IMP | 82 | — | — |
| 1-BT200-C | Day 2 | 58 | −24 | −0.29 |
| 1-BT200-C | Day 7 | 71 | −13 | −0.13 |
| 1-BT200-C | Day 14 | 99 | 17 | 0.21 |
| 1-BT200-C | Day 21 | 79 | −3 | −0.04 |

TABLE 3-continued

| Factor VIII Activity | | | | |
|---|---|---|---|---|
| Description | Visit | Result (%) | Absolute Change | Relative Change |
| 1-BT200-C | Day 28 | 72 | −10 | −0.12 |
| 1-BT200-D | Day 0, 1 h prior IMP | 89 | — | — |
| 1-BT200-D | Day 2 | 129 | 40 | 0.45 |
| 1-BT200-D | Day 7 | 62 | −27 | −0.3 |
| 1-BT200-D | Day 14 | 89 | 0 | 0 |
| 1-BT200-D | Day 21 | 123 | 34 | 0.38 |
| 1-BT200-D | Day 28 | 154 | 65 | 0.73 |
| 1-BT200-E | Day 0, 1 h prior IMP | 49 | — | — |
| 1-BT200-E | Day 2 | 63 | 14 | 0.29 |
| 1-BT200-E | Day 7 | 50 | 1 | 0.02 |
| 1-BT200-E | Day 14 | 65 | 16 | 0.33 |
| 1-BT200-E | Day 21 | 56 | 7 | 0.14 |
| 1-BT200-E | Day 28 | 52 | 3 | 0.06 |
| 1-BT200-F | Day 0, 1 h prior IMP | 44 | — | — |
| 1-BT200-F | Day 2 | 68 | 24 | 0.55 |
| 1-BT200-F | Day 7 | 43 | −1 | −0.02 |
| 1-BT200-F | Day 14 | 74 | 30 | 0.68 |
| 1-BT200-F | Day 21 | 101 | 57 | 1.3 |
| 1-BT200-F | Day 28 | 124 | 80 | 1.82 |
| 1-Control-A | Day 0, 1 h prior IMP | 66 | — | — |
| 1-Control-A | Day 2 | 67 | 1 | 0.02 |
| 1-Control-A | Day 7 | 47 | −19 | −0.29 |
| 1-Control-A | Day 14 | 115 | 49 | 0.74 |
| 1-Control-A | Day 21 | 132 | 66 | 1 |
| 1-Control-A | Day 28 | 87 | 21 | 0.32 |
| 1-Control-B | Day 0, 1 h prior IMP | 80 | — | — |
| 1-Control-B | Day 2 | 104 | 24 | 0.3 |
| 1-Control-B | Day 7 | 101 | 21 | 0.26 |
| 1-Control-B | Day 21 | 161 | 81 | 1.01 |
| 1-Control-B | Day 28 | 99 | 19 | 0.24 |
| 2-BT200-A | Day 0, 1 h prior IMP | 27 | — | — |
| 2-BT200-A | Day 2 | 49 | 22 | 0.81 |
| 2-BT200-A | Day 7 | 49 | 22 | 0.81 |
| 2-BT200-A | Day 14 | 64 | 37 | 1.37 |
| 2-BT200-A | Day 21 | 56 | 29 | 1.07 |
| 2-BT200-A | Day 28 | 40 | 13 | 0.48 |
| 2-BT200-B | Day 0, 1 h prior IMP | 68 | — | — |
| 2-BT200-B | Day 2 | 133 | 65 | 0.96 |
| 2-BT200-B | Day 7 | 185 | 117 | 1.72 |
| 2-BT200-B | Day 14 | 158 | 90 | 1.32 |
| 2-BT200-B | Day 21 | 176 | 108 | 1.59 |
| 2-BT200-B | Day 28 | 118 | 50 | 0.74 |
| 2-BT200-C | Day 0, 1 h prior IMP | 112 | — | — |
| 2-BT200-C | Day 2 | 137 | 25 | 0.22 |
| 2-BT200-C | Day 7 | 72 | −40 | −0.36 |
| 2-BT200-C | Day 14 | 132 | 20 | 0.18 |
| 2-BT200-C | Day 21 | 132 | 20 | 0.18 |
| 2-BT200-C | Day 28 | 150 | 38 | 0.34 |
| 2-BT200-D | Day 0, 1 h prior IMP | 70 | — | — |
| 2-BT200-D | Day 2 | 141 | 71 | 1.01 |
| 2-BT200-D | Day 7 | 134 | 64 | 0.91 |
| 2-BT200-D | Day 14 | 176 | 106 | 1.53 |
| 2-BT200-D | Day 21 | 137 | 67 | 0.96 |
| 2-BT200-D | Day 28 | 147 | 77 | 1.1 |
| 2-BT200-E | Day 0, 1 h prior IMP | 101 | — | — |
| 2-BT200-E | Day 2 | 111 | 10 | 0.1 |
| 2-BT200-E | Day 7 | 88 | −13 | −0.13 |
| 2-BT200-E | Day 14 | 107 | 6 | 0.06 |
| 2-BT200-E | Day 21 | 119 | 18 | 0.18 |
| 2-BT200-E | Day 28 | 101 | 0 | 0 |
| 2-BT200-F | Day 0, 1 h prior IMP | 74 | — | — |
| 2-BT200-F | Day 2 | 141 | 67 | 0.91 |
| 2-BT200-F | Day 7 | 116 | 42 | 0.57 |
| 2-BT200-F | Day 14 | 113 | 39 | 0.53 |
| 2-BT200-F | Day 21 | 86 | 12 | 0.16 |
| 2-BT200-F | Day 28 | 135 | 61 | 0.82 |
| 2-Control-A | Day 0, 1 h prior IMP | 31 | — | — |
| 2-Control-A | Day 2 | 28 | −3 | −0.1 |
| 2-Control-A | Day 7 | 86 | 55 | 1.77 |
| 2-Control-A | Day 14 | 42 | 11 | 0.35 |
| 2-Control-A | Day 21 | 42 | 11 | 0.35 |
| 2-Control-A | Day 28 | 44 | 13 | 0.42 |
| 2-Control-B | Day 0, 1 h prior IMP | 112 | — | — |
| 2-Control-B | Day 2 | 144 | 32 | 0.29 |
| 2-Control-B | Day 7 | 125 | 13 | 0.12 |

TABLE 3-continued

| Description | Visit | Result (%) | Absolute Change | Relative Change |
|---|---|---|---|---|
| | Factor VIII Activity | | | |
| 2-Control-B | Day 14 | 160 | 48 | 0.43 |
| 2-Control-B | Day 21 | 148 | 36 | 0.32 |
| 2-Control-B | Day 28 | 122 | 10 | 0.09 |
| 3-BT200-A | Day 0, 1 h prior IMP | 163 | — | — |
| 3-BT200-A | Day 2 | 144 | −19 | −0.12 |
| 3-BT200-A | Day 7 | 202 | 39 | 0.24 |
| 3-BT200-A | Day 14 | 144 | −19 | −0.12 |
| 3-BT200-A | Day 21 | 134 | −29 | −0.18 |
| 3-BT200-A | Day 28 | 117 | −46 | −0.28 |
| 3-BT200-B | Day 0, 1 h prior IMP | 75 | — | — |
| 3-BT200-B | Day 2 | 126 | 51 | 0.68 |
| 3-BT200-B | Day 7 | 130 | 55 | 0.73 |
| 3-BT200-B | Day 14 | 91 | 16 | 0.21 |
| 3-BT200-B | Day 21 | 94 | 19 | 0.25 |
| 3-BT200-B | Day 28 | 113 | 38 | 0.53 |
| 3-BT200-C | Day 0, 1 h prior IMP | 126 | — | — |
| 3-BT200-C | Day 2 | 197 | 71 | 0.56 |
| 3-BT200-C | Day 7 | 197 | 71 | 0.56 |
| 3-BT200-C | Day 14 | 189 | 63 | 0.5 |
| 3-BT200-C | Day 21 | 188 | 62 | 0.49 |
| 3-BT200-C | Day 28 | 167 | 41 | 0.33 |
| 3-BT200-D | Day 0, 1 h prior IMP | 70 | — | — |
| 3-BT200-D | Day 2 | 82 | 12 | 0.17 |
| 3-BT200-D | Day 7 | 158 | 88 | 1.26 |
| 3-BT200-D | Day 14 | 133 | 63 | 0.9 |
| 3-BT200-D | Day 21 | 106 | 36 | 0.51 |
| 3-BT200-D | Day 28 | 112 | 42 | 0.6 |
| 3-BT200-E | Day 0, 1 h prior IMP | 67 | — | — |
| 3-BT200-E | Day 2 | 95 | 28 | 0.42 |
| 3-BT200-E | Day 7 | 107 | 40 | 0.6 |
| 3-BT200-E | Day 14 | 100 | 33 | 0.49 |
| 3-BT200-E | Day 21 | 87 | 20 | 0.3 |
| 3-BT200-E | Day 28 | 81 | 14 | 0.21 |
| 3-BT200-F | Day 0, 1 h prior IMP | 68 | — | — |
| 3-BT200-F | Day 2 | 105 | 37 | 0.54 |
| 3-BT200-F | Day 7 | 120 | 52 | 0.76 |
| 3-BT200-F | Day 14 | 75 | 7 | 0.1 |
| 3-BT200-F | Day 21 | 110 | 42 | 0.62 |
| 3-BT200-F | Day 28 | 93 | 25 | 0.37 |
| 3-Control-A | Day 0, 1 h prior IMP | 100 | — | — |
| 3-Control-A | Day 2 | 98 | −2 | −0.02 |
| 3-Control-A | Day 7 | 117 | 17 | 0.17 |
| 3-Control-A | Day 14 | 98 | −2 | −0.02 |
| 3-Control-A | Day 21 | 114 | 14 | 0.14 |
| 3-Control-A | Day 28 | 101 | 1 | 0.01 |
| 3-Control-B | Day 0, 1 h prior IMP | 112 | — | — |
| 3-Control-B | Day 2 | 102 | −10 | −0.09 |
| 3-Control-B | Day 7 | 146 | 34 | 0.3 |
| 3-Control-B | Day 14 | 138 | 26 | 0.23 |
| 3-Control-B | Day 21 | 106 | −6 | −0.05 |
| 3-Control-B | Day 28 | 130 | 18 | 0.16 |
| 4-BT200-A | Day 0, 1 h prior IMP | 137 | — | — |
| 4-BT200-A | Day 2 | 151 | 14 | 0.1 |
| 4-BT200-A | Day 7 | 187 | 50 | 0.36 |
| 4-BT200-A | Day 14 | 211 | 74 | 0.54 |
| 4-BT200-A | Day 21 | 96 | −41 | −0.3 |
| 4-BT200-A | Day 28 | 88 | −49 | −0.36 |
| 4-BT200-B | Day 0, 1 h prior IMP | 101 | — | — |
| 4-BT200-B | Day 2 | 167 | 66 | 0.65 |
| 4-BT200-B | Day 7 | 207 | 106 | 1.05 |
| 4-BT200-B | Day 14 | 142 | 41 | 0.41 |
| 4-BT200-B | Day 21 | 93 | −8 | −0.08 |
| 4-BT200-B | Day 28 | 88 | −13 | −0.13 |
| 4-BT200-C | Day 0, 1 h prior IMP | 74 | — | — |
| 4-BT200-C | Day 2 | 175 | 101 | 1.36 |
| 4-BT200-C | Day 7 | 138 | 64 | 0.86 |
| 4-BT200-C | Day 14 | 90 | 16 | 0.22 |
| 4-BT200-C | Day 21 | 98 | 24 | 0.32 |
| 4-BT200-C | Day 28 | 50 | −24 | −0.32 |
| 4-BT200-D | Day 0, 1 h prior IMP | 97 | — | — |
| 4-BT200-D | Day 2 | 190 | 93 | 0.96 |
| 4-BT200-D | Day 7 | 165 | 68 | 0.7 |
| 4-BT200-D | Day 14 | 128 | 31 | 0.32 |
| 4-BT200-D | Day 21 | 116 | 19 | 0.2 |
| 4-BT200-D | Day 28 | 91 | −6 | 0.06 |

TABLE 3-continued

| Description | Visit | Result (%) | Absolute Change | Relative Change |
|---|---|---|---|---|
| | Factor VIII Activity | | | |
| 4-BT200-E | Day 0, 1 h prior IMP | 238 | — | — |
| 4-BT200-E | Day 2 | 143 | −95 | −0.4 |
| 4-BT200-E | Day 7 | 257 | 19 | 0.08 |
| 4-BT200-E | Day 14 | 271 | 33 | 0.14 |
| 4-BT200-E | Day 21 | 279 | 41 | 0.17 |
| 4-BT200-E | Day 28 | 238 | 0 | 0 |
| 4-BT200-F | Day 0, 1 h prior IMP | 201 | — | — |
| 4-BT200-F | Day 2 | 261 | 60 | 0.3 |
| 4-BT200-F | Day 7 | 254 | 53 | 0.26 |
| 4-BT200-F | Day 14 | 257 | 56 | 0.28 |
| 4-BT200-F | Day 21 | 203 | 2 | 0.01 |
| 4-BT200-F | Day 28 | 185 | −16 | 0.08 |
| 4-Control-A | Day 0, 1 h prior IMP | 59 | — | — |
| 4-Control-A | Day 2 | 83 | 24 | 0.41 |
| 4-Control-A | Day 7 | 68 | 9 | 0.15 |
| 4-Control-A | Day 14 | 73 | 14 | 0.24 |
| 4-Control-A | Day 21 | 76 | 17 | 0.29 |
| 4-Control-A | Day 28 | 77 | 18 | 0.31 |
| 4-Control-B | Day 0, 1 h prior IMP | 79 | — | — |
| 4-Control-B | Day 2 | 71 | −8 | −0.1 |
| 4-Control-B | Day 7 | 45 | −34 | −0.43 |
| 4-Control-B | Day 14 | 83 | 4 | 0.05 |
| 4-Control-B | Day 21 | 45 | −34 | −0.43 |
| 4-Control-B | Day 28 | 89 | 10 | 0.13 |
| 5-BT200-A | Day 0, 1 h prior IMP | 85 | — | — |
| 5-BT200-A | Day 2 | 221 | 136 | 1.6 |
| 5-BT200-A | Day 7 | 312 | 227 | 2.67 |
| 5-BT200-A | Day 14 | 218 | 133 | 1.56 |
| 5-BT200-A | Day 21 | 183 | 98 | 1.15 |
| 5-BT200-A | Day 28 | 132 | 47 | 0.55 |
| 5-BT200-B | Day 0, 1 h prior IMP | 80 | — | — |
| 5-BT200-B | Day 2 | 226 | 146 | 1.83 |
| 5-BT200-B | Day 7 | 396 | 316 | 3.95 |
| 5-BT200-B | Day 14 | 167 | 87 | 1.09 |
| 5-BT200-B | Day 28 | 124 | 44 | 0.55 |
| 5-BT200-C | Day 0, 1 h prior IMP | 90 | — | — |
| 5-BT200-C | Day 2 | 210 | 120 | 1.33 |
| 5-BT200-C | Day 7 | 306 | 216 | 2.4 |
| 5-BT200-C | Day 14 | 192 | 102 | 1.13 |
| 5-BT200-C | Day 21 | 169 | 79 | 0.88 |
| 5-BT200-C | Day 28 | 130 | 40 | 0.44 |
| 5-BT200-D | Day 0, 1 h prior IMP | 83 | — | — |
| 5-BT200-D | Day 2 | 185 | 102 | 1.23 |
| 5-BT200-D | Day 7 | 258 | 175 | 2.11 |
| S-BT200-I | Day 14 | 155 | 72 | 0.87 |
| 5-BT200-D | Day 21 | 133 | 50 | 0.6 |
| 5-BT200-D | Day 28 | 91 | 8 | 0.1 |
| 5-BT200-E | Day 0, 1 h prior IMP | 63 | — | — |
| 5-BT200-E | Day 2 | 170 | 107 | 1.7 |
| 5-BT200-E | Day 7 | 236 | 173 | 2.75 |
| 5-BT200-E | Day 14 | 156 | 93 | 1.48 |
| 5-BT200-E | Day 21 | 162 | 99 | 1.57 |
| 5-BT200-E | Day 28 | 90 | 27 | 0.43 |
| 5-BT200-F | Day 0, 1 h prior IMP | 79 | — | — |
| 5-BT200-F | Day 2 | 220 | 141 | 1.78 |
| 5-BT200-F | Day 7 | 278 | 199 | 2.52 |
| 5-BT200-F | Day 14 | 170 | 91 | 1.15 |
| 5-BT200-F | Day 21 | 114 | 35 | 0.44 |
| 5-BT200-F | Day 28 | 76 | −3 | −0.04 |
| 5-Control-A | Day 0, 1 h prior IMP | 67 | — | — |
| 5-Control-A | Day 2 | 77 | 10 | 0.15 |
| 5-Control-A | Day 7 | 65 | −2 | −0.03 |
| 5-Control-A | Day 14 | 50 | −17 | −0.25 |
| 5-Control-A | Day 21 | 78 | 11 | 0.16 |
| 5-Control-A | Day 28 | 69 | 2 | 0.03 |
| 5-Control-B | Day 0, 1 h prior IMP | 95 | — | — |
| 5-Control-B | Day 2 | 132 | 37 | 0.39 |
| 5-Control-B | Day 7 | 133 | 38 | 0.4 |
| 5-Control-B | Day 14 | 72 | −23 | −0.24 |
| 5-Control-B | Day 21 | 109 | 14 | 0.15 |
| 5-Control-B | Day 28 | 93 | 2 | −0.02 |
| 6-BT200-A | Day 0, 1 h prior IMP | 120 | — | — |
| 6-BT200-A | Day 2 | 164 | 44 | 0.37 |
| 6-BT200-A | Day 7 | 231 | 111 | 0.93 |
| 6-BT200-A | Day 14 | 238 | 118 | 0.98 |

TABLE 3-continued

| Description | Visit | Factor VIII Activity Result (%) | Absolute Change | Relative Change |
|---|---|---|---|---|
| 6-BT200-A | Day 21 | 171 | 51 | 0.43 |
| 6-BT200-A | Day 28 | 98 | −22 | −0.18 |
| 6-BT200-B | Day 0, 1 h prior IMP | 90 | — | — |
| 6-BT200-B | Day 2 | 151 | 61 | 0.68 |
| 6-BT200-B | Day 7 | 280 | 190 | 2.11 |
| 6-BT200-B | Day 14 | 241 | 151 | 1.68 |
| 6-BT200-B | Day 21 | 188 | 98 | 1.09 |
| 6-BT200-B | Day 28 | 119 | 29 | 0.32 |
| 6-BT200-C | Day 0, 1 h prior IMP | 104 | — | — |
| 6-BT200-C | Day 2 | 227 | 123 | 1.18 |
| 6-BT200-C | Day 7 | 254 | 150 | 1.44 |
| 6-BT200-C | Day 14 | 146 | 42 | 0.4 |
| 6-BT200-C | Day 21 | 143 | 39 | 0.38 |
| 6-BT200-C | Day 28 | 124 | 20 | 0.19 |
| 6-BT200-D | Day 0, 1 h prior IMP | 134 | — | — |
| 6-BT200-D | Day 2 | 171 | 37 | 0.28 |
| 5-BT200-D | Day 7 | 315 | 181 | 1.35 |
| 6-BT200-D | Day 14 | 297 | 163 | 1.22 |
| 6-BT200-D | Day 21 | 261 | 127 | 0.95 |
| 6-BT200-D | Day 28 | 178 | 44 | 0.33 |
| 6-BT200-E | Day 0, 1 h prior IMP | 57 | — | — |
| 6-BT200-E | Day 2 | — | — | — |
| 6-BT200-E | Day 7 | 142 | 85 | 1.49 |
| 6-BT200-E | Day 14 | 145 | 88 | 1.54 |
| 6-BT200-E | Day 21 | 125 | 68 | 1.19 |
| 6-BT200-E | Day 28 | 84 | 27 | 0.47 |
| 6-BT200-F | Day 0, 1 h prior IMP | 84 | — | — |
| 6-BT200-F | Day 2 | 166 | 82 | 0.98 |
| 6-BT200-F | Day 7 | 335 | 251 | 2.99 |
| 6-BT200-F | Day 14 | 202 | 118 | 1.4 |
| 6-BT200-F | Day 21 | 125 | 41 | 0.49 |
| 6-BT200-F | Day 28 | 71 | −13 | −0.15 |
| 6-Control-A | Day 0, 1 h prior IMP | 122 | — | — |
| 6-Control-A | Day 2 | 90 | −32 | −0.26 |
| 6-Control-A | Day 7 | 126 | 4 | 0.03 |
| 6-Control-A | Day 14 | 107 | −15 | −0.12 |
| 6-Control-A | Day 21 | 106 | −16 | −0.13 |
| 6-Control-A | Day 28 | 106 | −16 | −0.13 |
| 6-Control-B | Day 0, 1 h prior IMP | 59 | — | — |
| 6-Control-B | Day 2 | 103 | 44 | 0.75 |
| 6-Control-B | Day 7 | 94 | 35 | 0.59 |
| 6-Control-B | Day 14 | 144 | 85 | 1.44 |
| 6-Control-B | Day 21 | 105 | 46 | 0.78 |
| 6-Control-B | Day 28 | 54 | −5 | −0.08 |
| 7-BT200-A | Day 0, 1 h prior IMP | 104 | — | — |
| 7-BT200-A | Day 2 | 247 | 143 | 1.38 |
| 7-BT200-A | Day 7 | 295 | 191 | 1.84 |
| 7-BT200-A | Day 14 | 255 | 151 | 1.45 |
| 7-BT200-A | Day 21 | 160 | 56 | 0.54 |
| 7-BT200-A | Day 28 | 100 | −4 | −0.04 |
| 7-BT200-B | Day 0, 1 h prior IMP | 90 | — | — |
| 7-BT200-B | Day 2 | 240 | 150 | 1.67 |
| 7-BT200-B | Day 7 | 281 | 191 | 2.12 |
| 7-BT200-B | Day 14 | 205 | 115 | 1.28 |
| 7-BT200-B | Day 21 | 114 | 24 | 0.27 |
| 7-BT200-B | Day 28 | 95 | 5 | 0.06 |
| 7-BT200-C | Day 0, 1 h prior IMP | 74 | — | — |
| 7-BT200-C | Day 2 | 212 | 138 | 1.86 |
| 7-BT200-C | Day 7 | 312 | 238 | 3.22 |
| 7-BT200-C | Day 14 | 210 | 136 | 1.84 |
| 7-BT200-C | Day 21 | 165 | 91 | 1.23 |
| 7-BT200-C | Day 28 | 106 | 32 | 0.43 |
| 7-BT200-D | Day 0, 1 h prior IMP | 68 | — | — |
| 7-BT200-D | Day 2 | 125 | 57 | 0.84 |
| 7-BT200-D | Day 7 | 223 | 155 | 2.28 |
| 7-BT200-D | Day 14 | 139 | 71 | 1.04 |
| 7-BT200-D | Day 21 | 131 | 63 | 0.93 |
| 7-BT200-D | Day 28 | 116 | 48 | 0.71 |
| 7-BT200-E | Day 0, 1 h prior IMP | 101 | — | — |
| 7-BT200-E | Day 2 | 201 | 100 | 0.99 |
| 7-BT200-E | Day 7 | 249 | 148 | 1.47 |
| 7-BT200-E | Day 14 | 212 | 111 | 1.1 |
| 7-BT200-E | Day 21 | 144 | 43 | 0.43 |
| 7-BT200-E | Day 28 | 114 | 13 | 0.13 |
| 7-BT200-F | Day 0, 1 h prior IMP | 56 | — | — |

TABLE 3-continued

| Description | Visit | Factor VIII Activity Result (%) | Absolute Change | Relative Change |
|---|---|---|---|---|
| 7-BT200-F | Day 2 | 246 | 190 | 3.39 |
| 7-BT200-F | Day 7 | 399 | 343 | 6.13 |
| 7-BT200-F | Day 14 | 238 | 182 | 3.25 |
| 7-BT200-F | Day 21 | 132 | 76 | 1.36 |
| 7-BT200-F | Day 28 | 91 | 35 | 0.63 |
| 7-Control-A | Day 0, 1 h prior IMP | 102 | — | — |
| 7-Control-A | Day 2 | 145 | 43 | 0.42 |
| 7-Control-A | Day 7 | 123 | 21 | 0.21 |
| 7-Control-A | Day 14 | 91 | −11 | −0.11 |
| 7-Control-A | Day 21 | 102 | 0 | 0 |
| 7-Control-A | Day 28 | 119 | 17 | 0.17 |
| 7-Control-B | Day 0, 1 h prior IMP | 162 | — | — |
| 7-Control-B | Day 2 | 176 | 14 | 0.09 |
| 7-Control-B | Day 7 | 142 | −20 | −0.12 |
| 7-Control-B | Day 14 | 166 | 4 | 0.02 |
| 7-Control-B | Day 21 | 99 | −63 | −0.39 |
| 7-Control-B | Day 28 | — | — | — |
| 8-BT200-A | Day 0, 1 h prior IMP | 143 | — | — |
| 8-BT200-A | Day 2 | 288 | 145 | 1.01 |
| 8-BT200-A | Day 7 | 482 | 339 | 2.37 |
| 8-BT200-A | Day 14 | 444 | 301 | 2.1 |
| 8-BT200-A | Day 21 | 282 | 139 | 0.97 |
| 8-BT200-A | Day 28 | 245 | 102 | 0.71 |
| 8-BT200-B | Day 0, 1 h prior IMP | 74 | — | — |
| 8-BT200-B | Day 2 | 248 | 174 | 2.35 |
| 8-BT200-B | Day 7 | 406 | 332 | 4.49 |
| 8-BT200-B | Day 14 | 297 | 223 | 3.01 |
| 8-BT200-B | Day 21 | 216 | 142 | 1.92 |
| 8-BT200-B | Day 28 | 186 | 112 | 1.51 |
| 8-BT200-C | Day 0, 1 h prior IMP | 99 | — | — |
| 8-BT200-C | Day 2 | 295 | 196 | 1.98 |
| 8-BT200-C | Day 7 | 451 | 352 | 3.56 |
| 8-BT200-C | Day 14 | 389 | 290 | 2.93 |
| 8-BT200-C | Day 21 | 256 | 157 | 1.59 |
| 8-BT200-C | Day 28 | 226 | 127 | 1.28 |
| 8-BT200-D | Day 0, 1 h prior IMP | 87 | — | — |
| 8-BT200-D | Day 2 | 258 | 171 | 1.97 |
| 8-BT200-D | Day 7 | 406 | 319 | 3.67 |
| 8-BT200-D | Day 14 | 293 | 206 | 2.37 |
| 8-BT200-D | Day 21 | 193 | 106 | 1.22 |
| 8-BT200-D | Day 28 | 130 | 43 | 0.49 |
| 8-BT200-E | Day 0, 1 h prior IMP | 66 | — | — |
| 8-BT200-E | Day 2 | 335 | 269 | 4.08 |
| 8-BT200-E | Day 7 | 310 | 244 | 3.7 |
| 8-BT200-E | Day 14 | 323 | 257 | 3.89 |
| 8-BT200-E | Day 21 | 146 | 80 | 1.21 |
| 8-BT200-E | Day 28 | 249 | 183 | 2.77 |
| 8-BT200-F | Day 0, 1 h prior IMP | 154 | — | — |
| 8-BT200-F | Day 2 | 247 | 93 | 0.6 |
| 8-BT200-F | Day 7 | 359 | 205 | 1.33 |
| 8-BT200-F | Day 21 | 277 | 123 | 0.8 |
| 8-BT200-F | Day 28 | 242 | 88 | 0.57 |
| 8-Control-A | Day 0, 1 h prior IMP | 156 | — | — |
| 8-Control-A | Day 2 | 157 | 1 | 0.01 |
| 8-Control-A | Day 7 | 95 | −61 | −0.39 |
| 8-Control-A | Day 14 | 127 | −29 | −0.19 |
| 8-Control-A | Day 21 | 114 | −42 | −0.27 |
| 8-Control-A | Day 28 | 66 | −90 | −0.58 |
| 8-Control-B | Day 0, 1 h prior IMP | 176 | — | — |
| 8-Control-B | Day 2 | 149 | −27 | −0.15 |
| 8-Control-B | Day 7 | 197 | 21 | 0.12 |
| 8-Control-B | Day 14 | 192 | 16 | 0.09 |
| 8-Control-B | Day 21 | 229 | 53 | 0.3 |
| 8-Control-B | Day 28 | 195 | 19 | 0.11 |
| 9-BT200-A | Day 0, 1 h prior IMP | 143 | — | — |
| 9-BT200-A | Day 2 | 220 | 77 | 0.54 |
| 9-BT200-A | Day 7 | 298 | 155 | 1.08 |
| 9-BT200-A | Day 21 | 289 | 146 | 1.02 |
| 9-BT200-A | Day 28 | 247 | 104 | 0.73 |
| 9-BT200-B | Day 0, 1 h prior IMP | 153 | — | — |
| 9-BT200-B | Day 2 | 336 | 183 | 1.2 |
| 9-BT200-B | Day 7 | 463 | 310 | 2.03 |
| 9-BT200-B | Day 14 | 372 | 219 | 1.43 |
| 9-BT200-B | Day 21 | 287 | 134 | 0.88 |
| 9-BT200-B | Day 28 | 271 | 118 | 0.77 |

TABLE 3-continued

| Factor VIII Activity | | | | |
|---|---|---|---|---|
| Description | Visit | Result (%) | Absolute Change | Relative Change |
| 9-BT200-C | Day 0, 1 h prior IMP | 117 | — | — |
| 9-BT200-C | Day 2 | 263 | 146 | 1.25 |
| 9-BT200-C | Day 7 | 400 | 283 | 2.42 |
| 9-BT200-C | Day 14 | 300 | 183 | 1.56 |
| 9-BT200-C | Day 21 | 229 | 112 | 0.96 |
| 9-BT200-C | Day 28 | 196 | 79 | 0.68 |
| 9-BT200-D | Day 0, 1 h prior IMP | 87 | — | — |
| 9-BT200-D | Day 2 | 214 | 127 | 1.46 |
| 9-BT200-D | Day 7 | 336 | 249 | 2.86 |
| 9-BT200-D | Day 14 | 400 | 313 | 3.6 |
| 9-BT200-D | Day 21 | 282 | 195 | 2.24 |
| 9-BT200-D | Day 28 | 228 | 141 | 1.62 |
| 9-BT200-E | Day 0, 1 h prior IMP | 123 | — | — |
| 9-BT200-E | Day 2 | 295 | 172 | 1.4 |
| 9-BT200-E | Day 7 | 390 | 267 | 2.17 |
| 9-BT200-E | Day 14 | 325 | 202 | 1.64 |
| 9-BT200-E | Day 21 | 254 | 131 | 1.07 |
| 9-BT200-E | Day 28 | 204 | 81 | 0.66 |
| 9-BT200-F | Day 0, 1 h prior IMP | 113 | — | — |
| 9-BT200-F | Day 2 | 246 | 133 | 1.18 |
| 9-BT200-F | Day 7 | 392 | 279 | 2.47 |
| 9-BT200-F | Day 14 | 326 | 213 | 1.88 |
| 9-BT200-F | Day 21 | 185 | 72 | 0.64 |
| 9-BT200-F | Day 28 | 241 | 128 | 1.13 |
| 9-Control-A | Day 0, 1 h prior IMP | 104 | — | — |
| 9-Control-A | Day 2 | 117 | 13 | 0.13 |
| 9-Control-A | Day 7 | 69 | −35 | −0.34 |
| 9-Control-A | Day 14 | 89 | −15 | −0.14 |
| 9-Control-A | Day 21 | 60 | −44 | −0.42 |
| 9-Control-A | Day 28 | 92 | −12 | −0.12 |
| 9-Control-B | Day 0, 1 h prior IMP | 130 | — | — |
| 9-Control-B | Day 2 | 240 | 110 | 0.85 |
| 9-Control-B | Day 7 | 188 | 58 | 0.45 |
| 9-Control-B | Day 14 | 196 | 66 | 0.51 |
| 9-Control-B | Day 21 | 139 | 9 | 0.07 |
| 9-Control-B | Day 28 | 209 | 79 | 0.61 |
| 10-BT200-A | Day 0, 1 h prior IMP | 162 | — | — |
| 10-BT200-A | Day 2 | 337 | 175 | 1.08 |
| 10-BT200-A | Day 7 | 434 | 272 | 1.68 |
| 10-BT200-A | Day 14 | 290 | 128 | 0.79 |
| 10-BT200-A | Day 21 | 394 | 232 | 1.43 |
| 10-BT200-B | Day 0, 1 h prior IMP | 108 | — | — |
| 10-BT200-B | Day 2 | 224 | 116 | 1.07 |
| 10-BT200-B | Day 7 | 318 | 210 | 1.94 |
| 10-BT200-B | Day 14 | 305 | 197 | 1.82 |
| 10-BT200-B | Day 21 | 233 | 125 | 1.16 |
| 10-BT200-B | Day 28 | 92 | −16 | −0.15 |
| 10-BT200-C | Day 0, 1 h prior IMP | 69 | — | — |
| 10-BT200-C | Day 2 | 224 | 155 | 2.25 |
| 10-BT200-C | Day 7 | 245 | 176 | 2.55 |
| 10-BT200-C | Day 14 | 268 | 199 | 2.88 |
| 10-BT200-C | Day 21 | 241 | 172 | 2.49 |
| 10-BT200-C | Day 28 | 160 | 91 | 1.32 |
| 10-BT200-D | Day 0, 1 h prior IMP | 195 | — | — |
| 10-BT200-D | Day 2 | 389 | 194 | 0.99 |
| 10-BT200-D | Day 7 | 498 | 303 | 1.55 |
| 10-BT200-D | Day 14 | 400 | 205 | 1.05 |
| 10-BT200-D | Day 21 | 382 | 187 | 0.96 |
| 10-BT200-D | Day 28 | 267 | 72 | 0.37 |
| 10-BT200-E | Day 0, 1 h prior IMP | 90 | — | — |
| 10-BT200-E | Day 2 | 220 | 130 | 1.44 |
| 10-BT200-E | Day 7 | 303 | 213 | 2.37 |
| 10-BT200-E | Day 14 | 297 | 207 | 2.3 |
| 10-BT200-E | Day 21 | 238 | 148 | 1.64 |
| 10-BT200-E | Day 28 | 180 | 90 | 1 |
| 10-BT200-F | Day 0, 1 h prior IMP | 145 | — | — |
| 10-BT200-F | Day 2 | 304 | 159 | 1.1 |
| 10-BT200-F | Day 7 | 556 | 411 | 2.83 |
| 10-BT200-F | Day 14 | 452 | 307 | 2.12 |
| 10-BT200-F | Day 21 | 263 | 118 | 0.81 |
| 10-BT200-F | Day 28 | 151 | 6 | 0.04 |
| 10-Control-A | Day 0, 1 h prior IMP | 125 | — | — |
| 10-Control-A | Day 2 | 122 | −3 | −0.02 |
| 10-Control-A | Day 7 | 139 | 14 | 0.11 |
| 10-Control-A | Day 14 | 60 | −65 | −0.52 |
| 10-Control-A | Day 21 | 117 | −8 | −0.06 |
| 10-Control-A | Day 28 | 124 | − 1 | −0.01 |
| 10-Control-B | Day 0, 1 h prior IMP | 165 | — | — |
| 10-Control-B | Day 2 | 193 | 28 | 0.17 |
| 10-Control-B | Day 7 | 131 | −34 | −0.21 |
| 10-Control-B | Day 14 | 235 | 70 | 0.42 |
| 10-Control-B | Day 21 | 228 | 63 | 0.38 |
| 10-Control-B | Day 28 | 142 | −23 | −0.14 |

TABLE 4

| VWF Antigen | | | | |
|---|---|---|---|---|
| Description | Timing | Result (%) | Absolute Change | Relative Change |
| 1-BT200-A | Day 0, 1 h prior IMP | 79 | — | — |
| 1-BT200-A | Day 2 | 146 | 67 | 0.85 |
| 1-BT200-A | Day 7 | 91 | 12 | 0.15 |
| 1-BT200-A | Day 14 | 80 | 1 | 0.01 |
| 1-BT200-A | Day 21 | 78 | −1 | −0.01 |
| 1-BT200-A | Day 28 | 68 | −11 | −0.14 |
| 1-BT200-B | Day 0, 1 h prior IMP | 64 | — | — |
| 1-BT200-B | Day 2 | 64 | 0 | 0 |
| 1-BT200-B | Day 7 | 47 | −17 | −0.27 |
| 1-BT200-B | Day 14 | 51 | −13 | −0.2 |
| 1-BT200-B | Day 21 | 69 | 5 | 0.08 |
| 1-BT200-B | Day 28 | 70 | 6 | 0.09 |
| 1-BT200-C | Day 0, 1 h prior IMP | 58 | — | — |
| 1-BT200-C | Day 2 | 67 | 9 | 0.16 |
| 1-BT200-C | Day 7 | 63 | 5 | 0.09 |
| 1-BT200-C | Day 14 | 57 | −1 | −0.02 |
| 1-BT200-C | Day 21 | 54 | −4 | −0.07 |
| 1-BT200-C | Day 28 | 49 | −9 | −0.16 |
| 1-BT200-D | Day 0, 1 h prior IMP | 111 | — | — |
| 1-BT200-D | Day 2 | 131 | 20 | 0.18 |
| 1-BT200-D | Day 7 | 89 | −22 | −0.2 |
| 1-BT200-D | Day 14 | 97 | −14 | −0.13 |
| L-BT200-D | Day 21 | 105 | −6 | −0.05 |
| 1-BT200-D | Day 28 | 128 | 17 | 0.15 |
| 1-BT200-E | Day 0, 1 h prior IMP | 52 | — | — |
| 1-BT200-E | Day 2 | 75 | 23 | 0.44 |
| 1-BT200-E | Day 7 | 42 | −10 | −0.19 |
| 1-BT200-E | Day 14 | 61 | 9 | 0.17 |
| 1-BT200-E | Day 21 | 34 | −18 | −0.35 |
| 1-BT200-E | Day 28 | 45 | −7 | −0.13 |
| 1-BT200-F | Day 0, 1 h prior IMP | 76 | — | — |
| 1-BT200-F | Day 2 | 80 | 4 | 0.05 |
| 1-BT200-F | Day 7 | — | — | — |
| 1-BT200-F | Day 14 | 77 | 1 | 0.01 |
| 1-BT200-F | Day 21 | 87 | 11 | 0.14 |
| 1-BT200-F | Day 28 | 104 | 28 | 0.37 |
| 1-Control-A | Day 0, 1 h prior IMP | 73 | — | — |
| 1-Control-A | Day 2 | 88 | 15 | 0.21 |
| 1-Control-A | Day 7 | 56 | −17 | −0.23 |
| 1-Control-A | Day 14 | 97 | 24 | 0.33 |
| 1-Control-A | Day 21 | 112 | 39 | 0.53 |
| 1-Control-A | Day 28 | 76 | 3 | 0.04 |
| 1-Control-B | Day 0, 1 h prior IMP | 89 | — | — |
| 1-Control-B | Day 2 | 122 | 33 | 0.37 |
| 1-Control-B | Day 7 | 105 | 16 | 0.18 |
| 1-Control-B | Day 21 | 135 | 46 | 0.52 |
| 1-Control-B | Day 28 | 103 | 14 | 0.16 |
| 2-BT200-A | Day 0, 1 h prior IMP | 29 | — | — |
| 2-BT200-A | Day 2 | 58 | 29 | 1 |
| 2-BT200-A | Day 7 | 57 | 28 | 0.97 |
| 2-BT200-A | Day 14 | 55 | 26 | 0.9 |
| 2-BT200-A | Day 21 | 47 | 18 | 0.62 |
| 2-BT200-A | Day 28 | 55 | 26 | 0.9 |
| 2-BT200-B | Day 0, 1 h prior IMP | 79 | — | — |
| 2-BT200-B | Day 2 | 167 | 88 | 1.11 |
| 2-BT200-B | Day 7 | 154 | 75 | 0.95 |

TABLE 4-continued

| VWF Antigen | | | | |
|---|---|---|---|---|
| Description | Timing | Result (%) | Absolute Change | Relative Change |
| 2-BT200-B | Day 14 | 146 | 67 | 0.85 |
| 2-BT200-B | Day 21 | 194 | 115 | 1.46 |
| 2-BT200-B | Day 28 | 145 | 66 | 0.84 |
| 2-BT200-C | Day 0, 1 h prior IMP | 133 | — | — |
| 2-BT200-C | Day 2 | 119 | −14 | −0.11 |
| 2-BT200-C | Day 7 | 66 | −67 | −0.5 |
| 2-BT200-C | Day 14 | 101 | −32 | −0.24 |
| 2-BT200-C | Day 21 | 125 | −8 | −0.06 |
| 2-BT200-C | Day 28 | 113 | −20 | −0.15 |
| 2-BT200-D | Day 0, 1 h prior IMP | 87 | — | — |
| 2-BT200-D | Day 2 | 114 | 27 | 0.31 |
| 2-BT200-D | Day 7 | 99 | 12 | 0.14 |
| 2-BT200-D | Day 14 | 107 | 20 | 0.23 |
| 2-BT200-D | Day 21 | 121 | 34 | 0.39 |
| 2-BT200-D | Day 28 | 94 | 7 | 0.08 |
| 2-BT200-E | Day 0, 1 h prior IMP | 134 | — | — |
| 2-BT200-E | Day 2 | 116 | −18 | −0.13 |
| 2-BT200-E | Day 7 | 91 | −43 | −0.32 |
| 2-BT200-E | Day 14 | 96 | −38 | −0.28 |
| 2-BT200-E | Day 21 | 123 | −11 | −0.08 |
| 2-BT200-E | Day 28 | 121 | −13 | −0.1 |
| 2-BT200-F | Day 0, 1 h prior IMP | 81 | — | — |
| 2-BT200-F | Day 2 | 105 | 24 | 0.3 |
| 2-BT200-F | Day 7 | 93 | 12 | 0.15 |
| 2-BT200-F | Day 14 | 85 | 4 | 0.05 |
| 2-BT200-F | Day 21 | 59 | −22 | −0.27 |
| 2-BT200-F | Day 28 | 85 | 4 | 0.05 |
| 2-Control-A | Day 0, 1 h prior IMP | 42 | — | — |
| 2-Control-A | Day 2 | 41 | −1 | −0.02 |
| 2-Control-A | Day 7 | 74 | 32 | 0.76 |
| 2-Control-A | Day 14 | 54 | 12 | 0.29 |
| 2-Control-A | Day 21 | 47 | 5 | 0.12 |
| 2-Control-A | Day 28 | 53 | 11 | 0.26 |
| 2-Control-B | Day 0, 1 h prior IMP | 123 | — | — |
| 2-Control-B | Day 2 | 129 | 6 | 0.05 |
| 2-Control-B | Day 7 | 317 | −6 | −0.05 |
| 2-Control-B | Day 14 | 142 | 19 | 0.15 |
| 2-Control-B | Day 21 | 103 | −20 | −0.16 |
| 2-Control-B | Day 28 | 131 | 8 | 0.07 |
| 3-BT200-A | Day 0, 1 h prior IMP | 106 | — | — |
| 3-BT200-A | Day 2 | 135 | 29 | 0.27 |
| 3-BT200-A | Day 7 | 147 | 41 | 0.39 |
| 3-BT200-A | Day 14 | 114 | 8 | 0.08 |
| 3-BT200-A | Day 21 | 96 | −10 | −0.09 |
| 3-BT200-A | Day 28 | 107 | 1 | 0.01 |
| 3-BT200-B | Day 0, 1 h prior IMP | 64 | — | — |
| 3-BT200-B | Day 2 | 92 | 28 | 0.44 |
| 3-BT200-B | Day 7 | 95 | 31 | 0.48 |
| 3-BT200-B | Day 14 | 93 | 29 | 0.45 |
| 3-BT200-B | Day 21 | 74 | 10 | 0.16 |
| 3-BT200-B | Day 28 | 80 | 16 | 0.25 |
| 3-BT200-C | Day 0, 1 h prior IMP | 141 | — | — |
| 3-BT200-C | Day 2 | 217 | 76 | 0.54 |
| 3-BT200-C | Day 7 | 193 | 52 | 0.37 |
| 3-BT200-C | Day 14 | 227 | 86 | 0.61 |
| 3-BT200-C | Day 21 | 175 | 34 | 0.24 |
| 3-BT200-C | Day 28 | 180 | 39 | 0.28 |
| 3-BT200-D | Day 0, 1 h prior IMP | 96 | — | — |
| 3-BT200-D | Day 2 | 35 | −61 | −0.64 |
| 3-BT200-D | Day 7 | 127 | 31 | 0.32 |
| 3-BT200-D | Day 14 | 96 | 0 | 0 |
| 3-BT200-D | Day 21 | 101 | 5 | 0.05 |
| 3-BT200-D | Day 28 | 100 | 4 | 0.04 |
| 3-BT200-E | Day 0, 1 h prior IMP | 70 | — | — |
| 3-BT200-E | Day 2 | 91 | 21 | 0.3 |
| 3-BT200-E | Day 7 | 98 | 28 | 0.4 |
| 3-BT200-E | Day 14 | 94 | 24 | 0.34 |
| 3-BT200-E | Day 21 | 109 | 39 | 0.56 |
| 3-BT200-E | Day 28 | 80 | 10 | 0.14 |
| 3-BT200-F | Day 0, 1 h prior IMP | 49 | — | — |
| 3-BT200-F | Day 2 | 80 | 31 | 0.63 |
| 3-BT200-F | Day 7 | 73 | 24 | 0.49 |
| 3-BT200-F | Day 14 | 71 | 22 | 0.45 |
| 3-BT200-F | Day 21 | 66 | 17 | 0.35 |
| 3-BT200-F | Day 28 | 63 | 14 | 0.29 |

TABLE 4-continued

| VWF Antigen | | | | |
|---|---|---|---|---|
| Description | Timing | Result (%) | Absolute Change | Relative Change |
| 3-Control-A | Day 0, 1 h prior IMP | 78 | — | — |
| 3-Control-A | Day 2 | 77 | −1 | −0.01 |
| 3-Control-A | Day 7 | 100 | 22 | 0.28 |
| 3-Control-A | Day 14 | 83 | 5 | 0.06 |
| 3-Control-A | Day 21 | 88 | 10 | 0.13 |
| 3-Control-A | Day 28 | 97 | 19 | 0.24 |
| 3-Control-B | Day 0, 1 h prior IMP | 101 | — | — |
| 3-Control-B | Day 2 | 84 | −17 | −0.17 |
| 3-Control-B | Day 7 | 117 | 16 | 0.16 |
| 3-Control-B | Day 14 | 113 | 12 | 0.12 |
| 3-Control-B | Day 21 | 112 | 11 | 0.11 |
| 3-Control-B | Day 28 | 102 | 1 | 0.01 |
| 4-BT200-A | Day 0, 1 h prior IMP | 104 | — | — |
| 4-BT200-A | Day 2 | 184 | 80 | 0.77 |
| 4-BT200-A | Day 7 | 243 | 139 | 1.34 |
| 4-BT200-A | Day 14 | 195 | 91 | 0.88 |
| 4-BT200-A | Day 21 | 106 | 2 | 0.02 |
| 4-BT200-A | Day 28 | 105 | 1 | 0.01 |
| 4-BT200-B | Day 0, 1 h prior IMP | 95 | — | — |
| 4-BT200-B | Day 2 | 146 | 51 | 0.54 |
| 4-BT200-B | Day 7 | 214 | 119 | 1.25 |
| 4-BT200-B | Day 14 | 181 | 86 | 0.91 |
| 4-BT200-B | Day 21 | 102 | 7 | 0.07 |
| 4-BT200-B | Day 28 | 76 | −19 | −0.2 |
| 4-BT200-C | Day 0, 1 h prior IMP | 68 | — | — |
| 4-BT200-C | Day 2 | 176 | 108 | 1.59 |
| 4-BT200-C | Day 7 | 148 | 80 | 1.18 |
| 4-BT200-C | Day 14 | 105 | 37 | 0.54 |
| 4-BT200-C | Day 21 | 89 | 21 | 0.31 |
| 4-BT200-C | Day 28 | 55 | −13 | −0.19 |
| 4-BT200-D | Day 0, 1 h prior IMP | 103 | — | — |
| 4-BT200-D | Day 2 | 156 | 53 | 0.51 |
| 4-BT200-D | Day 7 | 172 | 69 | 0.67 |
| 4-BT200-D | Day 14 | 140 | 37 | 0.36 |
| 4-BT200-D | Day 21 | 119 | 16 | 0.16 |
| 4-BT200-D | Day 28 | 76 | −27 | −0.26 |
| 4-BT200-E | Day 0, 1 h prior IMP | 198 | — | — |
| 4-BT200-E | Day 2 | 212 | 14 | 0.07 |
| 4-BT200-E | Day 7 | 328 | 130 | 0.66 |
| 4-BT200-E | Day 14 | 271 | 73 | 0.37 |
| 4-BT200-E | Day 21 | 265 | 67 | 0.34 |
| 4-BT200-E | Day 28 | 275 | 77 | 0.39 |
| 4-BT200-F | Day 0, 1 h prior IMP | 150 | — | — |
| 4-BT200-F | Day 2 | 258 | 108 | 0.72 |
| 4-BT200-F | Day 7 | 325 | 175 | 1.17 |
| 4-BT200-F | Day 14 | 208 | 58 | 0.39 |
| 4-BT200-F | Day 21 | 193 | 43 | 0.29 |
| 4-BT200-F | Day 28 | 151 | 1 | 0.01 |
| 4-Control-A | Day 0, 1 h prior IMP | 61 | — | — |
| 4-Control-A | Day 2 | 67 | 6 | 0.1 |
| 4-Control-A | Day 7 | 69 | 8 | 0.13 |
| 4-Control-A | Day 14 | 57 | −4 | −0.07 |
| 4-Control-A | Day 21 | 72 | 11 | 0.18 |
| 4-Control-A | Day 28 | 67 | 6 | 0.1 |
| 4-Control-B | Day 0, 1 h prior IMP | 67 | — | — |
| 4-Control-B | Day 2 | 69 | 2 | 0.03 |
| 4-Control-B | Day 7 | 22 | −45 | −0.67 |
| 4-Control-B | Day 14 | 67 | 0 | 0 |
| 4-Control-B | Day 21 | 47 | −20 | −0.3 |
| 4-Control-B | Day 28 | 68 | 1 | 0.01 |
| 5-BT200-A | Day 0, 1 h prior IMP | 100 | — | — |
| 5-BT200-A | Day 2 | 198 | 98 | 0.98 |
| 5-BT200-A | Day 7 | 311 | 211 | 2.11 |
| 5-BT200-A | Day 14 | 303 | 203 | 2.03 |
| 5-BT200-A | Day 21 | 165 | 65 | 0.65 |
| 5-BT200-A | Day 28 | 125 | 25 | 0.25 |
| 5-BT200-B | Day 0, 1 h prior IMP | 99 | — | — |
| 5-BT200-B | Day 2 | 218 | 119 | 1.2 |
| 5-BT200-B | Day 7 | 408 | 309 | 3.12 |
| 5-BT200-B | Day 14 | 247 | 148 | 1.49 |
| 5-BT200-B | Day 28 | 117 | 18 | 0.18 |
| 5-BT200-C | Day 0, 1 h prior IMP | 107 | — | — |
| 5-BT200-C | Day 2 | 193 | 86 | 0.8 |
| 5-BT200-C | Day 7 | 323 | 216 | 2.02 |
| 5-BT200-C | Day 14 | 230 | 123 | 1.15 |

TABLE 4-continued

| VWF Antigen | | | | |
|---|---|---|---|---|
| Description | Timing | Result (%) | Absolute Change | Relative Change |
| 5-BT200-C | Day 21 | 159 | 52 | 0.49 |
| 5-BT200-C | Day 28 | 134 | 27 | 0.25 |
| 5-BT200-D | Day 0, 1 h prior IMP | 104 | — | — |
| 5-BT200-D | Day 2 | 203 | 99 | 0.95 |
| 5-BT200-D | Day 7 | 399 | 295 | 2.84 |
| 5-BT200-D | Day 14 | 215 | 111 | 1.07 |
| 5-BT200-D | Day 21 | 108 | 4 | 0.04 |
| 5-BT200-D | Day 28 | 110 | 6 | 0.06 |
| 5-BT200-E | Day 0, 1 h prior IMP | 96 | — | — |
| 5-BT200-E | Day 2 | 183 | 87 | 0.91 |
| 5-BT200-E | Day 7 | 304 | 208 | 2.17 |
| 5-BT200-E | Day 14 | 275 | 179 | 1.86 |
| 5-BT200-E | Day 21 | 171 | 75 | 0.78 |
| 5-BT200-E | Day 28 | 112 | 16 | 0.17 |
| 5-BT200-F | Day 0, 1 h prior IMP | 66 | — | — |
| 5-BT200-F | Day 2 | 192 | 126 | 1.91 |
| 5-BT200-F | Day 7 | 314 | 248 | 3.76 |
| 5-BT200-F | Day 14 | 172 | 106 | 1.61 |
| 5-BT200-F | Day 21 | 102 | 36 | 0.55 |
| 5-BT200-F | Day 28 | 66 | 0 | 0 |
| 5-Control-A | Day 0, 1 h prior IMP | 69 | — | — |
| 5-Control-A | Day 2 | 72 | 3 | 0.04 |
| 5-Control-A | Day 7 | 75 | 6 | 0.09 |
| 5-Control-A | Day 14 | 77 | 8 | 0.12 |
| 5-Control-A | Day 21 | 70 | 1 | 0.01 |
| 5-Control-A | Day 28 | 71 | 2 | 0.03 |
| 5-Control-B | Day 0, 1 h prior IMP | 107 | — | — |
| 5-Control-B | Day 2 | 109 | 2 | 0.02 |
| 5-Control-B | Day 7 | 98 | −9 | −0.08 |
| 5-Control-B | Day 14 | 88 | −19 | −0.18 |
| 5-Control-B | Day 21 | 97 | −10 | −0.09 |
| 5-Control-B | Day 28 | 90 | −17 | −0.16 |
| 6-BT200-A | Day 0, 1 h prior IMP | 129 | — | — |
| 6-BT200-A | Day 2 | 220 | 91 | 0.71 |
| 6-BT200-A | Day 7 | 441 | 312 | 2.42 |
| 6-BT200-A | Day 14 | 309 | 180 | 1.4 |
| 6-BT200-A | Day 21 | 248 | 119 | 0.92 |
| 6-BT200-A | Day 28 | 124 | −5 | −0.04 |
| 6-BT200-B | Day 0, 1 h prior IMP | 115 | — | — |
| 6-BT200-B | Day 2 | 184 | 69 | 0.6 |
| 6-BT200-B | Day 7 | 362 | 247 | 2.15 |
| 6-BT200-B | Day 14 | 358 | 243 | 2.11 |
| 6-BT200-B | Day 21 | 233 | 118 | 1.03 |
| 6-BT200-B | Day 28 | 140 | 25 | 0.22 |
| 6-BT200-C | Day 0, 1 h prior IMP | 149 | — | — |
| 6-BT200-C | Day 2 | 248 | 99 | 0.66 |
| 6-BT200-C | Day 7 | 288 | 139 | 0.93 |
| 6-BT200-C | Day 14 | 201 | 52 | 0.35 |
| 6-BT200-C | Day 21 | 152 | 3 | 0.02 |
| 6-BT200-C | Day 28 | 118 | −31 | −0.21 |
| 6-BT200-D | Day 0, 1 h prior IMP | 216 | — | — |
| 6-BT200-D | Day 2 | 202 | −14 | −0.06 |
| 6-BT200-D | Day 7 | 420 | 204 | 0.94 |
| 6-BT200-D | Day 14 | 420 | 204 | 0.94 |
| 6-BT200-D | Day 21 | 374 | 158 | 0.73 |
| 6-BT200-D | Day 28 | 250 | 34 | 0.16 |
| 6-BT200-E | Day 0, 1 h prior IMP | 80 | — | — |
| 6-BT200-E | Day 2 | 5 | — | — |
| 6-BT200-E | Day 7 | 148 | 68 | 0.85 |
| 6-BT200-E | Day 14 | 121 | 41 | 0.51 |
| 6-BT200-E | Day 21 | 109 | 29 | 0.36 |
| 6-BT200-E | Day 28 | 100 | 20 | 0.25 |
| 6-BT200-F | Day 0, 1 h prior IMP | 73 | — | — |
| 6-BT200-F | Day 2 | 166 | 93 | 1.27 |
| 6-BT200-F | Day 7 | 402 | 329 | 4.51 |
| 6-BT200-F | Day 14 | 296 | 223 | 3.05 |
| 6-BT200-F | Day 21 | 132 | 59 | 0.81 |
| 6-BT200-F | Day 28 | 87 | 14 | 0.19 |
| 6-Control-A | Day 0, 1 h prior IMP | 95 | — | — |
| 6-Control-A | Day 2 | 97 | 2 | 0.02 |
| 6-Control-A | Day 7 | 101 | 6 | 0.06 |
| 6-Control-A | Day 14 | 86 | −9 | −0.09 |
| 6-Control-A | Day 21 | 95 | 0 | 0 |
| 6-Control-A | Day 28 | 87 | −8 | −0.08 |
| 6-Control-B | Day 0, 1 h prior IMP | 93 | — | — |

TABLE 4-continued

| VWF Antigen | | | | |
|---|---|---|---|---|
| Description | Timing | Result (%) | Absolute Change | Relative Change |
| 6-Control-B | Day 2 | 107 | 14 | 0.15 |
| 6-Control-B | Day 7 | 110 | 17 | 0.18 |
| 6-Control-B | Day 14 | 130 | 37 | 0.4 |
| 6-Control-B | Day 21 | 119 | 26 | 0.28 |
| 6-Control-B | Day 28 | 80 | −13 | −0.14 |
| 7-BT200-A | Day 0, 1 h prior IMP | 101 | — | — |
| 7-BT200-A | Day 2 | 192 | 91 | 0.9 |
| 7-BT200-A | Day 7 | 420 | 319 | 3.16 |
| 7-BT200-A | Day 14 | 299 | 198 | 1.96 |
| 7-BT200-A | Day 21 | 182 | 81 | 0.8 |
| 7-BT200-A | Day 28 | 97 | −4 | −0.04 |
| 7-BT200-B | Day 0, 1 h prior IMP | 86 | — | — |
| 7-BT200-B | Day 2 | 188 | 102 | 1.19 |
| 7-BT200-B | Day 7 | 357 | 271 | 3.15 |
| 7-BT200-B | Day 14 | 284 | 198 | 2.3 |
| 7-BT200-B | Day 21 | 141 | 55 | 0.64 |
| 7-BT200-B | Day 28 | 104 | 18 | 0.21 |
| 7-BT200-C | Day 0, 1 h prior IMP | 83 | — | — |
| 7-BT200-C | Day 2 | 207 | 124 | 1.49 |
| 7-BT200-C | Day 7 | 420 | 337 | 4.06 |
| 7-BT200-C | Day 14 | 351 | 268 | 3.23 |
| 7-BT200-C | Day 21 | 217 | 134 | 1.61 |
| 7-BT200-C | Day 28 | 115 | 32 | 0.39 |
| 7-BT200-D | Day 0, 1 h prior IMP | 92 | — | — |
| 7-BT200-D | Day 2 | 106 | 14 | 0.15 |
| 7-BT200-D | Day 7 | 221 | 129 | 1.4 |
| 7-BT200-D | Day 14 | 153 | 61 | 0.66 |
| 7-BT200-D | Day 21 | 131 | 39 | 0.42 |
| 7-BT200-D | Day 28 | 118 | 26 | 0.28 |
| 7-BT200-E | Day 0, 1 h prior IMP | 89 | — | — |
| 7-BT200-E | Day 2 | 165 | 76 | 0.85 |
| 7-BT200-E | Day 7 | 213 | 124 | 1.39 |
| 7-BT200-E | Day 14 | 222 | 133 | 1.49 |
| 7-BT200-E | Day 21 | 136 | 47 | 0.53 |
| 7-BT200-E | Day 28 | 112 | 23 | 0.26 |
| 7-BT200-F | Day 0, 1 h prior IMP | 66 | — | — |
| 7-BT200-F | Day 2 | 207 | 141 | 2.14 |
| 7-BT200-F | Day 7 | 366 | 300 | 4.55 |
| 7-BT200-F | Day 14 | 297 | 231 | 3.5 |
| 7-BT200-F | Day 21 | 139 | 73 | 1.11 |
| 7-BT200-F | Day 28 | 93 | 27 | 0.41 |
| 7-Control-A | Day 0, 1 h prior IMP | 124 | — | — |
| 7-Control-A | Day 2 | 123 | −1 | −0.01 |
| 7-Control-A | Day 7 | 104 | −20 | −0.16 |
| 7-Control-A | Day 14 | 98 | −26 | −0.21 |
| 7-Control-A | Day 21 | 112 | −12 | −0.1 |
| 7-Control-A | Day 28 | 129 | 5 | 0.04 |
| 7-Control-B | Day 0, 1 h prior IMP | 151 | — | — |
| 7-Control-B | Day 2 | 142 | −9 | −0.06 |
| 7-Control-B | Day 7 | 107 | −44 | −0.29 |
| 7-Control-B | Day 14 | 165 | 14 | 0.09 |
| 7-Control-B | Day 21 | 116 | −35 | −0.23 |
| 7-Control-B | Day 28 | — | — | — |
| 8-BT200-A | Day 0, 1 h prior IMP | 120 | — | — |
| 8-BT200-A | Day 2 | 300 | 180 | 1.5 |
| 8-BT200-A | Day 7 | 420 | 300 | 2.5 |
| 8-BT200-A | Day 14 | 420 | 300 | 2.5 |
| 8-BT200-A | Day 21 | 234 | 114 | 0.95 |
| 8-BT200-A | Day 28 | 204 | 84 | 0.7 |
| 8-BT200-B | Day 0, 1 h prior IMP | 84 | — | — |
| 8-BT200-B | Day 2 | 292 | 208 | 2.48 |
| 8-BT200-B | Day 7 | 408 | 324 | 3.86 |
| 8-BT200-B | Day 14 | 408 | 324 | 3.86 |
| 8-BT200-B | Day 21 | 294 | 210 | 2.5 |
| 8-BT200-B | Day 28 | 164 | 80 | 0.95 |
| 8-BT200-C | Day 0, 1 h prior IMP | 136 | — | — |
| 8-BT200-C | Day 2 | 327 | 191 | 1.4 |
| 8-BT200-C | Day 7 | 563 | 427 | 3.14 |
| 8-BT200-C | Day 14 | 420 | 284 | 2.09 |
| 8-BT200-C | Day 21 | 367 | 231 | 1.7 |
| 8-BT200-C | Day 28 | 264 | 128 | 0.94 |
| 8-BT200-D | Day 0, 1 h prior IMP | 91 | — | — |
| 8-BT200-D | Day 2 | 253 | 162 | 1.78 |
| 8-BT200-D | Day 7 | 485 | 394 | 4.33 |
| 8-BT200-D | Day 14 | 345 | 254 | 2.79 |

TABLE 4-continued

| VWF Antigen | | | | |
|---|---|---|---|---|
| Description | Timing | Result (%) | Absolute Change | Relative Change |
| 8-BT200-D | Day 21 | 125 | 34 | 0.37 |
| 8-BT200-D | Day 28 | 119 | 28 | 0.31 |
| 8-BT200-E | Day 0, 1 h prior IMP | 68 | — | — |
| 8-BT200-E | Day 2 | 281 | 213 | 3.13 |
| 8-BT200-E | Day 7 | 293 | 225 | 3.31 |
| 8-BT200-E | Day 14 | 324 | 256 | 3.76 |
| 8-BT200-E | Day 21 | 145 | 77 | 1.13 |
| 8-BT200-E | Day 28 | 137 | 69 | 1.01 |
| 8-BT200-F | Day 0, 1 h prior IMP | 111 | — | — |
| 8-BT200-F | Day 2 | 202 | 91 | 0.82 |
| 8-BT200-F | Day 7 | 307 | 196 | 1.77 |
| 8-BT200-F | Day 21 | 240 | 129 | 1.16 |
| 8-BT200-F | Day 28 | 177 | 66 | 0.59 |
| 8-Control-A | Day 0, 1 h prior IMP | 124 | — | — |
| 8-Control-A | Day 2 | 93 | −31 | −0.25 |
| 8-Control-A | Day 7 | 82 | −42 | −0.34 |
| 8-Control-A | Day 14 | 98 | −26 | −0.21 |
| 8-Control-A | Day 21 | 96 | −28 | −0.23 |
| 8-Control-A | Day 28 | 44 | −80 | −0.65 |
| 8-Control-B | Day 0, 1 h prior IMP | 156 | — | — |
| 8-Control-B | Day 2 | 163 | 7 | 0.04 |
| 8-Control-B | Day 7 | 175 | 19 | 0.12 |
| 8-Control-B | Day 14 | 159 | 3 | 0.02 |
| 8-Control-B | Day 21 | 182 | 26 | 0.17 |
| 8-Control-B | Day 28 | 194 | 38 | 0.24 |
| 9-BT200-A | Day 0, 1 h prior IMP | 148 | — | — |
| 9-BT200-A | Day 2 | 261 | 113 | 0.76 |
| 9-BT200-A | Day 7 | 468 | 320 | 2.16 |
| 9-BT200-A | Day 21 | 420 | 272 | 1.84 |
| 9-BT200-A | Day 28 | 337 | 189 | 1.28 |
| 9-BT200-B | Day 0, 1 h prior IMP | 132 | — | — |
| 9-BT200-B | Day 2 | 247 | 115 | 0.87 |
| 9-BT200-B | Day 7 | 420 | 288 | 2.18 |
| 9-BT200-B | Day 14 | 420 | 288 | 2.18 |
| 9-BT200-B | Day 21 | 368 | 236 | 1.79 |
| 9-BT200-B | Day 28 | 270 | 138 | 1.05 |
| 9-BT200-C | Day 0, 1 h prior IMP | 93 | — | — |
| 9-BT200-C | Day 2 | 183 | 90 | 0.97 |
| 9-BT200-C | Day 7 | 420 | 327 | 3.52 |
| 9-BT200-C | Day 14 | 326 | 233 | 2.51 |
| 9-BT200-C | Day 21 | 230 | 137 | 1.47 |
| 9-BT200-C | Day 28 | 142 | 49 | 0.53 |
| 9-BT200-D | Day 0, 1 h prior IMP | 101 | — | — |
| 9-BT200-D | Day 2 | 231 | 130 | 1.29 |
| 9-BT200-D | Day 7 | 468 | 367 | 3.63 |
| 9-BT200-D | Day 14 | 420 | 319 | 3.16 |
| 9-BT200-D | Day 21 | 360 | 259 | 2.56 |
| 9-BT200-D | Day 28 | 221 | 120 | 1.19 |
| 9-BT200-E | Day 0, 1 h prior IMP | 82 | — | — |
| 9-BT200-E | Day 2 | 223 | 141 | 1.72 |
| 9-BT200-E | Day 7 | 374 | 292 | 3.56 |
| 9-BT200-E | Day 14 | 355 | 273 | 3.33 |
| 9-BT200-E | Day 21 | 222 | 140 | 1.71 |
| 9-BT200-E | Day 28 | 133 | 51 | 0.62 |
| 9-BT200-F | Day 0, 1 h prior IMP | 95 | — | — |
| 9-BT200-F | Day 2 | 231 | 136 | 1.43 |
| 9-BT200-F | Day 7 | 418 | 323 | 3.4 |
| 9-BT200-F | Day 14 | 416 | 321 | 3.38 |
| 9-BT200-F | Day 21 | 268 | 173 | 1.82 |
| 9-BT200-F | Day 28 | 263 | 168 | 1.77 |
| 9-Control-A | Day 0, 1 h prior IMP | 98 | — | — |
| 9-Control-A | Day 2 | 88 | −10 | −0.3 |
| 9-Control-A | Day 7 | 88 | −10 | −0.1 |
| 9-Control-A | Day 14 | 110 | 12 | 0.12 |
| 9-Control-A | Day 21 | 89 | −9 | −0.09 |
| 9-Control-A | Day 28 | 103 | 5 | 0.05 |
| 9-Control-B | Day 0, 1 h prior IMP | 137 | — | — |
| 9-Control-B | Day 2 | 242 | 105 | 0.77 |
| 9-Control-B | Day 7 | 184 | 47 | 0.34 |
| 9-Control-B | Day 14 | 169 | 32 | 0.23 |
| 9-Control-B | Day 21 | 136 | −1 | −0.01 |
| 9-Control-B | Day 28 | 172 | 35 | 0.26 |
| 10-BT200-A | Day 0, 1 h prior IMP | 118 | — | — |
| 10-BT200-A | Day 2 | 260 | 142 | 1.2 |
| 10-BT200-A | Day 7 | 420 | 302 | 2.56 |

TABLE 4-continued

| VWF Antigen | | | | |
|---|---|---|---|---|
| Description | Timing | Result (%) | Absolute Change | Relative Change |
| 10-BT200-A | Day 14 | 420 | 302 | 2.56 |
| 10-BT200-A | Day 21 | 420 | 302 | 2.56 |
| 10-BT200-B | Day 0, 1 h prior IMP | 93 | — | — |
| 10-BT200-B | Day 2 | 218 | 125 | 1.34 |
| 10-BT200-B | Day 7 | 395 | 302 | 3.25 |
| 10-BT200-B | Day 14 | 387 | 294 | 3.16 |
| 10-BT200-B | Day 21 | 234 | 141 | 1.52 |
| 10-BT200-B | Day 28 | 73 | −20 | −0.22 |
| 10-BT200-C | Day 0, 1 h prior IMP | 76 | — | — |
| 10-BT200-C | Day 2 | 171 | 95 | 1.25 |
| 10-BT200-C | Day 7 | 329 | 253 | 3.33 |
| 10-BT200-C | Day 14 | 417 | 341 | 4.49 |
| 10-BT200-C | Day 21 | 274 | 198 | 2.61 |
| 10-BT200-C | Day 28 | 156 | 80 | 1.05 |
| 10-BT200-D | Day 0, 1 h prior IMP | 127 | — | — |
| 10-BT200-D | Day 2 | 311 | 184 | 1.45 |
| 10-BT200-D | Day 7 | 420 | 293 | 2.31 |
| 10-BT200-D | Day 14 | 420 | 293 | 2.31 |
| 10-BT200-D | Day 21 | 420 | 293 | 2.31 |
| 10-BT200-D | Day 28 | 322 | 195 | 1.54 |
| 10-BT200-E | Day 0, 1 h prior IMP | 59 | — | — |
| 10-BT200-E | Day 2 | 119 | 60 | 1.02 |
| 10-BT200-E | Day 7 | 240 | 181 | 3.07 |
| 10-BT200-E | Day 14 | 263 | 204 | 3.46 |
| 10-BT200-E | Day 21 | 186 | 127 | 2.15 |
| 10-BT200-E | Day 28 | 129 | 70 | 1.19 |
| 10-BT200-F | Day 0, 1 h prior IMP | 142 | — | — |
| 10-BT200-F | Day 2 | 255 | 113 | 0.8 |
| 10-BT200-F | Day 7 | 420 | 278 | 1.96 |
| 10-BT200-F | Day 14 | 420 | 278 | 1.96 |
| 10-BT200-F | Day 21 | 269 | 127 | 0.89 |
| 10-BT200-F | Day 28 | 104 | −38 | −0.27 |
| 10-Control-A | Day 0, 1 h prior IMP | 129 | — | — |
| 10-Control-A | Day 2 | 152 | 23 | 0.18 |
| 10-Control-A | Day 7 | 146 | 17 | 0.13 |
| 10-Control-A | Day 14 | 47 | −82 | −0.64 |
| 10-Control-A | Day 21 | 96 | −33 | −0.26 |
| 10-Control-A | Day 28 | 123 | −6 | −0.05 |
| 10-Control-B | Day 0, 1 h prior IMP | 137 | — | — |
| 10-Control-B | Day 2 | 130 | −7 | −0.05 |
| 10-Control-B | Day 7 | 138 | 1 | 0.01 |
| 10-Control-B | Day 14 | 231 | 94 | 0.69 |
| 10-Control-B | Day 21 | 172 | 35 | 0.26 |
| 10-Control-B | Day 28 | 104 | −33 | −0.24 |

The functions of VWF were also tested in the treated individuals. In three different activity tests: Multiplate aggregometer, Platelet Function Analyzer and ELISA for free A1 domains of VWF, no effect is observed as compared to non-treated individuals. The function of Factor VIII is also increased in BT200 treated volunteers.

The results in healthy volunteers show that a lower dose, 0.6 mg BT200, approximately doubles the baseline FVIII activity at 48 hours post-dose and maintains nearly half of that increase for 1 week post-dose. However, in the same time period, no effect on the function of VWF is observed using PFA-100® assay, a highly sensitive functional assay which uses undiluted whole blood.

The results also indicate that a 10-fold higher dose of BT200, 6 mg, maintains the doubling of baseline FVIII for 2 weeks after a single dose, without any evidence of VWF functional inhibition seen with the PFA-100® assay.

These observations indicate that BT200 can dose-dependently enhance the VWF/FVIII levels.

After single dose administration, the elimination half-life of BT200 in healthy volunteers are approximately 5-12 days, indicating a long half-life and good tolerability of BT200 after subcutaneous injection. No off-target adverse effects were observed upon BT200 administration.

Co-administration of BT200 and desmopressin demonstrated an additive effect on the levels of VWF and FVIII (as shown in FIG. 1) in the blood.

Example 2: Individual Dose-Titration to Dose-Response in Patients

A diverse set of up to 25 patients with severe congenital hemophilia A without inhibitors, mild-moderate hemophilia A, heterozygous carriers of hemophilia A with subnormal FVIII levels, VWD Type 1, "Vicenza" type, or VWD Type 2b are enrolled to a study to evaluate dose titration and dose-response.

Patients are dosed via subcutaneous (SC) injection, with 3 mg BT200 on Days 1, Day 4 and Day 7 (±2 days). BT200 doses were then titrated thereafter between 3 and 9 mg on Days 14, 21, and 28 depending on the bleeding disorder patients have. FVIII activity is measured in patients with Hemophilia A or VWD Type 1. Platelet counts and/or FVIII activity are measured in patients with VWD Type 2b.

Five patients with VWD Type 2b (3 males: 2 females) (Table 5), were dosed with 3 mg BT200 on Days 1 and 4 and followed by doses of 6-9 mg BT200 every week (Days 7, 14, 21 and 28). The patients have a median age of 61 years (ranging from 24-72 years). Four of five patients presented with thrombocytopenia and two patients were on regular recombinant VWF substitution therapy because of recurrent severe bleedings. Efficacy was measured by VWF parameters, FVIII activity, and platelet counts, and other clinical outcome parameters before, during and after therapy. Statistical analysis was performed by Friedman ANOVA.

TABLE 5

Patients with VWF Type 2b

| Patients | Age: gender | Mutations |
|---|---|---|
| #1 | 54; female | 3922 C > T het |
| #2 | 61; male | C3916C > T |
| #3 | 24; male | C3916C > T |
| #9 | 72; male | 3946G > A het |
| #10 | 61; female | C3939G > C |

Figure 2:
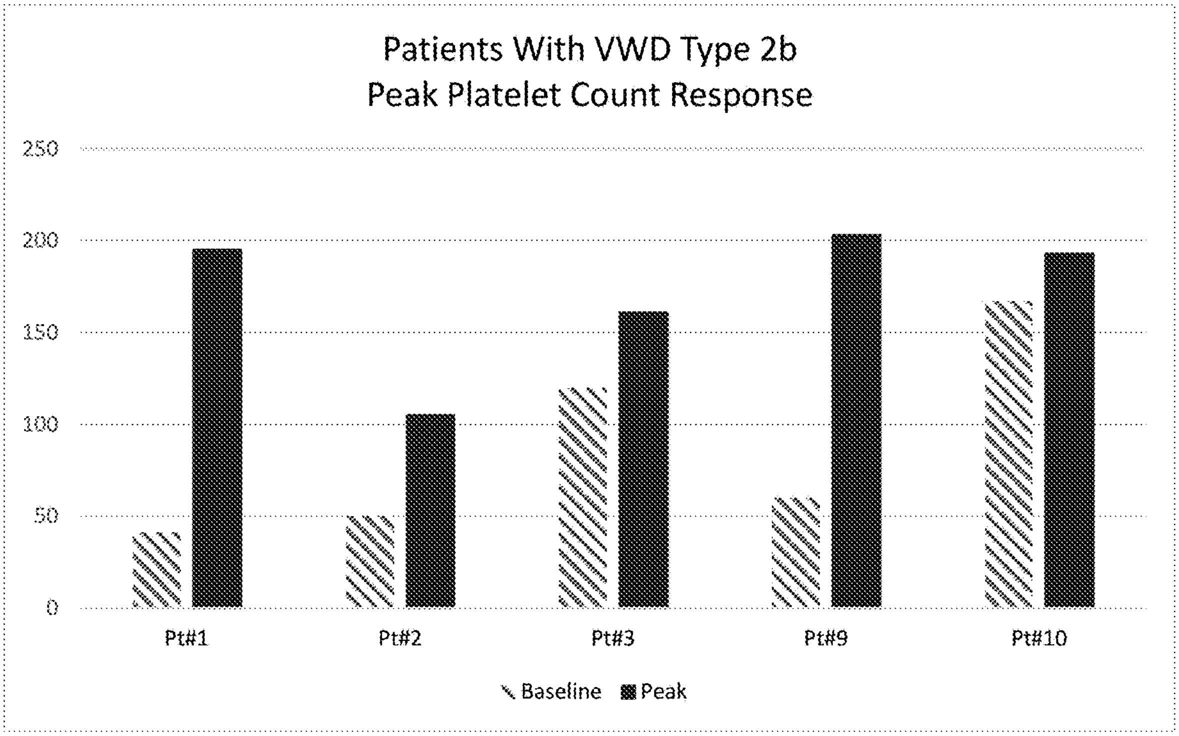
FIG. 2 is a histogram demonstrating platelet counts in patients with VWD Type 2b, after subcutaneous injection of BT200.
Figure 3:
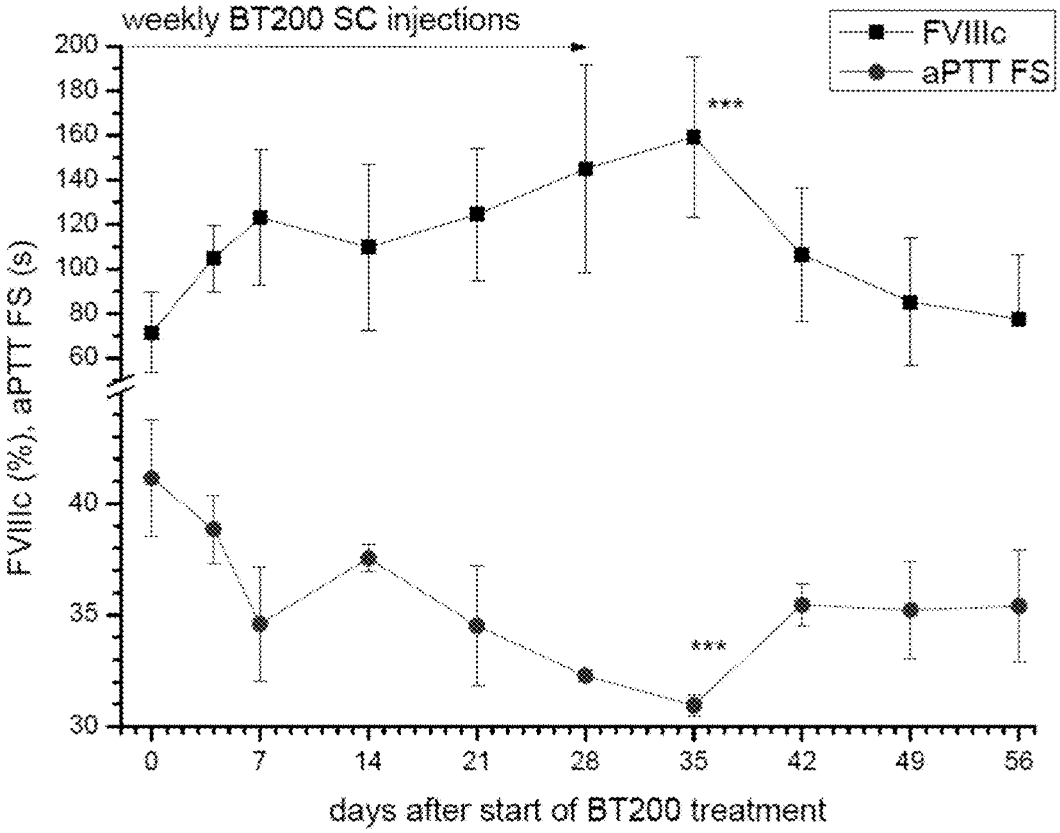
FIG. 3 displays increased FVIII levels and activity (aPTT FS) in patients with VWD Type2b after subcutaneous injection of BT200.
Figure 4A:
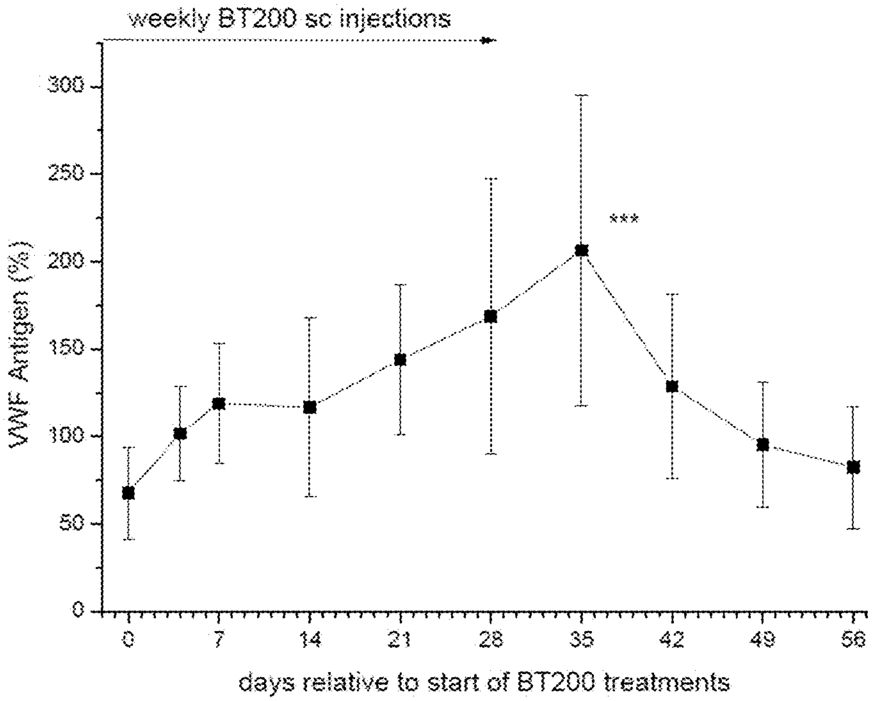
FIG. 4A shows increased VWF levels after subcutaneous injection of BT200.
Figure 4B:
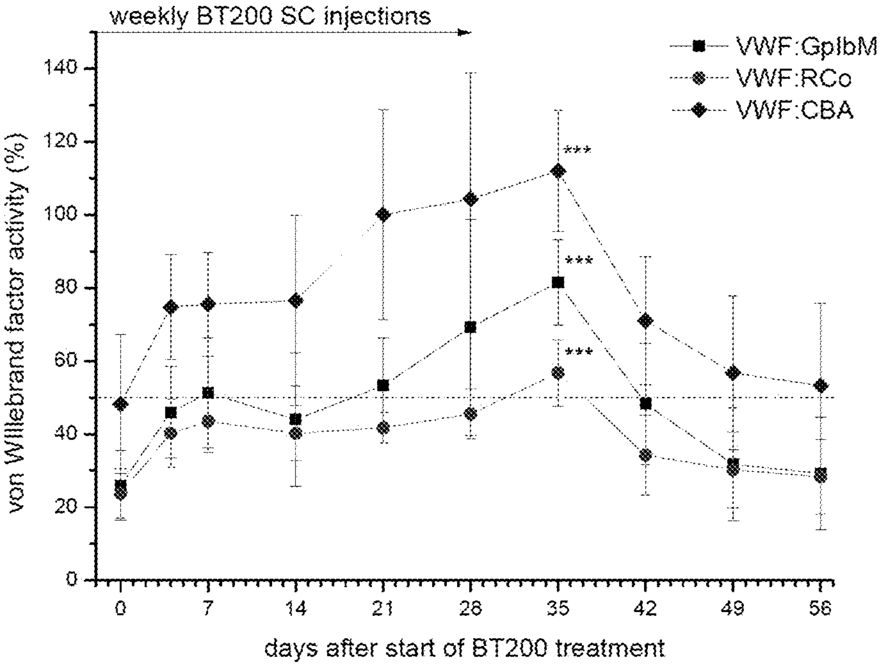
FIG. 4B shows increased VWF activity after subcutaneous injection of BT200 in patients with VWD Type 2b.

The results indicate clinically meaningful responses occurred in patients within 4 days after the first subcutaneous injection of BT200 (first dose 3 mg BT200). Platelet counts rose from a median of 60 at baseline to 159/nL at 28 days (p=0.012), i.e., up to 4-fold in all patients with thrombocytopenia, and normalized in ¾ of these patients (FIG. 2). All thrombocytopeni patients responded with an increase in platelet counts after 96 hours after first dose of BT200. Plasma levels of FVIIIc doubled from 67% (44-91%) to 134% (114-200%) (p<0.001), and normalized in the patient with subnormal FVIIIc activity (from 44% at baseline to 135% 1 week after the last dose). This was mirrored by a shortening of the uniformly prolonged activated partial thromboplastin time (aPTT-FS) from 43 s to 32 s (p=0.002) (FIG. 3) and increased thrombin generation. BT200 administrations increased circulating VWF antigen levels from 64% (32-106%) to 143% (103-351%, p<0.001) (FIG. 4A). VWF collagen binding activity (VWF:CBA) increased 2-4 fold in all patients, VWF ristocetin cofactor (VWF:RCo) activity and VWF:GpIbM activity increased 2-3 fold in all thrombocytopeniatients, but only by a small amount in the one patient without thrombocytopenia (all p-values<0.05 for n=5) (FIG. 4B). The increased ristocetin BT200 was very well tolerated without any relevant adverse effect.

These clinical observations indicate that BT200 specifically corrects the underlying pathophysiology of VWD Type 2b, rapidly and strongly increasing platelet counts in patients with thrombocytopenia, and elevating VWF and FVIIIc in all patients. It is hypothesized that BT200 may be of potential benefit for VWD Type 2b patients by increasing circulating VWF and FVIII levels in all patients, as well as platelet counts in thrombocytopeniatients.

Figure 5:
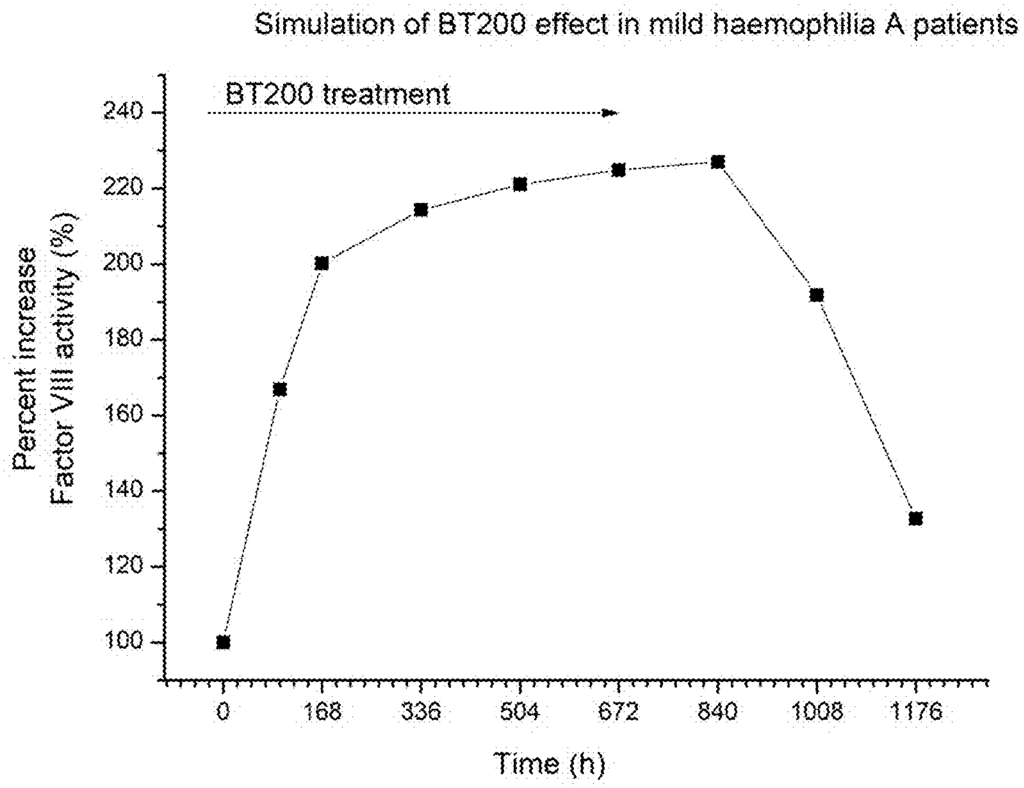
FIG. 5 shows increased Factor VIII activity (%) after BT200 prophylactic treatment in patients with mild hemophilia A.

Patients with haemophilia A were treated with BT200 with the same dosing schedule demonstrated increased FVIII activity (FIG. 5).

These results indicate that BT200 has a prolong half-life of 7 to 12 days. BT200 can induce sustained increases in VWF levels and activity, as well as increases in FVIII levels and activity measured by increased aPTT shortening and increased thrombin generation.

Example 3: BT200 Increases the Half-Life of FVIII Therapy

Patients were treated with a FVIII therapy (Refacto AF/three patients; Elocta/one patient; Afstyla/two patients; Kovaltry/one patient; and Advate/one patient). FVIII therapy's half-life before BT200 treatment was based on historical values known in the art. Patients were dosed with splitting loading doses and weekly doses followed with the loading doses (Table 6). The half-life of each FVIII therapy in each patient post BT200 treatment was measured one month after the BT200 treatment. All the FVIII values were generated through Chromogenic assay (Patients #014, 017, 020-024), or by one-stage clotting assay (Patient #027). The average increase is 3.1 folder (Median=2.8 folder) (Table 6). These observations suggest that BT200 can increase the half-life of almost all the FVIII product on the market.

TABLE 6

BT200 increases the half-life of FVIII therapy

| Patient ID | FVIII therapy | BT200 dosing | Pre-BT200 FVIII half-life(hr) | Post-BT200 FVIII half-life(hr) | Fold Increase |
|---|---|---|---|---|---|
| 014 | Refacto AF | 3 mg on Days 1, 4 and 7; 4 mg on Day 14; 5 mg on day 21; and 6 mg on Day 28 | 19 | 42.5 | 2.24 |
| 017 | Refacto AF | 3 mg on Days 1, 4 and 7; 5 mg on Day 14; 5 mg on day 21; and 7 mg on Day 28 | 11 | 36.5 | 3.34 |
| 020 | Elocta | 3 mg on Days 1, 4 and 7; 5 mg on Day 14; 6 mg on Day 21; and 7 mg on Day 28 | 24.2 | 62 | 2.56 |

TABLE 6-continued

BT200 increases the half-life of FVIII therapy

| Patient ID | FVIII therapy | BT200 dosing | Pre-BT200 FVIII half-life(hr) | Post-BT200 FVIII half-life(hr) | Fold Increase |
|---|---|---|---|---|---|
| 021 | Afstyla | 3 mg on Days 1, 4 and 7; 5 mg on Day 14; 6 mg on Day 21; and 7 mg on Day 28 | 14.5 | 29 | 2.00 |
| 022 | Kovaltry | 3 mg on Days 1, 4 and 7; 4 mg on Day 14; 5 mg on Day 21; and 7 mg on Day 28 | 7.7 | 26.7 | 3.47 |
| 023 | Afstyla | 3 mg on Days 1, 4 and 7; 6 mg on Day 14; 7 mg on Day 21; and 9 mg on Day 28 | 7.5 | 22.8 | 3.04 |
| 024 | Advate | 3 mg on Days 1, 4 and 7; 5 mg on Day 14; 6 mg on Day 21; and 7 mg on Day 28 | 13.5 | 34.5 | 2.56 |
| 027 | Refacto AF | 3 mg on Days 1, 4 and 7; 5 mg on Day 14; 6 mg on day 21; and 8 mg on Day 28 | 10 | 57 | 5.70 |

The invention claimed is:

1. A method for treating bleeding associated with von Willebrand's disease (VWD) in a subject comprising administering to the subject a Von Willebrand factor (VWF) targeting agent which comprises a sequence presented by SEQ ID NO: 6, wherein the VWF targeting agent is administered to the subject at a dose ranging from 0.6 mg to 9.0 mg.

2. The method of claim 1, wherein the VWD is VWD Type 1, VWD Type 1 Vicenza subtype, VWD Type 2a, VWD Type 2b, VWD Type 2b with thrombocytopenia, VWD Type 2m, VWD Type 2n, or VWD Type 3.

3. The method of claim 2, wherein the VWD is VWD Type 2b.

4. The method of claim 1, wherein the treatment of bleeding is a therapeutic treatment.

5. The method of claim 1, wherein the treatment of bleeding is a prophylactic treatment.

6. The method of claim 1, wherein the VWF targeting agent is administered to the subject at a dose ranging from 0.6 mg to 6.0 mg.

7. The method of claim 6, wherein the VWF targeting agent is administered to the subject at a dose of 0.6 mg.

8. The method of claim 6, wherein the VWF targeting agent is administered to the subject at a dose of 6.0 mg.

9. The method of claim 1, wherein the VWF targeting agent is administered to the subject with multiple doses, and wherein each dose is administered once every other day, or once every three days, or once every five days, or once a week, or once every other week.

10. The method of claim 9, wherein the VWF targeting agent is administered to the subject once a week.

11. The method of claim 9, wherein the VWF targeting agent is administered to the subject once every other week.

12. The method of claim 1, wherein the VWF targeting agent is administered to the subject via subcutaneous injection.

13. The method of claim 1, wherein the VWF targeting agent increases the levels and/or activity of VWF in the blood.

14. The method of claim 1, wherein the VWF targeting agent increases the levels and/or activity of FVIII in the blood.

15. The method of claim 1, wherein the VWF targeting agent increases the platelet counts in the blood.

16. The method of claim 1, wherein the VWF targeting agent is administered in combination with a coagulation factor substitute treatment.

17. The method of claim 16, wherein the coagulation factor substitute is a plasma derived FVIII concentrate, a VWF concentrate, a recombinant FVIII preparation, or—a recombinant VWF preparation.

18. The method of claim 17, wherein the coagulation factor substitute is a recombinant FVIII preparation.

19. The method of claim 18, wherein the VWF targeting agent increases half-life of the recombinant FVIII preparation at least 3 fold.

20. A method for treating bleeding in a patient diagnosed with von Willebrand's disease (VWD) with a pharmaceutical composition comprising a VWF binding agent, BT200, comprising:

a) assessing the baseline coagulation function in said patient;

b) determining the optimal dose of BT200 with the assessment of step a) for initial treatment; and c) providing a weekly dose of BT200 after one-week treatment with the initial dose of BT200 in said patient, wherein the initial dose of BT200 is from 0.6 mg to 9.0 mg.

21. The method of claim 20, wherein the VWD is VWD Type 1, VWD Type 1 Vicenza subtype, VWD Type 2a, VWD Type 2b, VWD Type 2b with thrombocytopenia, VWD Type 2m, VWD Type 2n, or VWD Type 3.

22. The method of claim 21, wherein the VWD is VWD Type 2b.

23. The method of claim 20, wherein the assessment includes FVIII activity, VWF antigen levels and/or platelet counts in the blood.

24. A method of increasing the half-life of a FVIII therapy in a patient who receives the FVIII therapy comprising administering to the patient an VWF targeting agent which comprises a sequence presented by SEQ ID NO: 6, and wherein the VWF targeting agent is administered at a dose ranging from 0.6 mg to 9.0 mg.

25. The method of claim 24, wherein the FVIII therapy is a plasma derived FVIII concentrate or a recombinant FVIII preparation.

26. The method of claim 24, wherein the VWF targeting agent is administered at a dose ranging from 1.0 mg to 9.0 mg.

27. The method of claim 26, wherein the half-life of the FVIII therapy increases at least 3 fold.

28. The method of claim 24, wherein the patient is diagnosed with von Willebrand's disease (VWD).

* * * * *